(12) United States Patent
Reisner et al.

(10) Patent No.: US 11,324,777 B2
(45) Date of Patent: May 10, 2022

(54) ANTI THIRD PARTY CENTRAL MEMORY T CELLS, METHODS OF PRODUCING SAME AND USE OF SAME IN TRANSPLANTATION AND DISEASE TREATMENT

(71) Applicant: Yeda Research and Development Co. Ltd., Rehovot (IL)

(72) Inventors: Yair Reisner, Old Jaffa (IL); Yaki Eidelstein, Rehovot (IL); Eran Ophir, Rehovot (IL); Assaf Lask, Rehovot (IL); Ran Afik, Rehovot (IL); Noga Or-Geva, Rehovot (IL); Esther Bachar-Lustig, Rehovot (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 49 days.

(21) Appl. No.: 15/825,275

(22) Filed: Nov. 29, 2017

(65) Prior Publication Data
US 2018/0193384 A1 Jul. 12, 2018

Related U.S. Application Data

(62) Division of application No. 14/343,053, filed as application No. PCT/IL2012/050354 on Sep. 6, 2012, now abandoned.

(60) Provisional application No. 61/532,172, filed on Sep. 8, 2011.

(51) Int. Cl.
| | |
|---|---|
| A61K 35/17 | (2015.01) |
| A61K 39/00 | (2006.01) |
| C12N 5/0783 | (2010.01) |
| A61K 35/22 | (2015.01) |
| A61K 35/26 | (2015.01) |
| A61K 35/28 | (2015.01) |
| A61K 35/34 | (2015.01) |
| A61K 35/36 | (2015.01) |
| A61K 35/38 | (2015.01) |
| A61K 35/39 | (2015.01) |
| A61K 35/407 | (2015.01) |
| A61K 35/42 | (2015.01) |
| A61K 35/12 | (2015.01) |

(52) U.S. Cl.
CPC .............. *A61K 35/17* (2013.01); *A61K 35/22* (2013.01); *A61K 35/26* (2013.01); *A61K 35/28* (2013.01); *A61K 35/34* (2013.01); *A61K 35/36* (2013.01); *A61K 35/38* (2013.01); *A61K 35/39* (2013.01); *A61K 35/407* (2013.01); *A61K 35/42* (2013.01); *A61K 39/001* (2013.01); *C12N 5/0636* (2013.01); *C12N 5/0637* (2013.01); *A61K 2035/122* (2013.01); *A61K 2035/124* (2013.01); *A61K 2039/5158* (2013.01); *C12N 2501/2307* (2013.01); *C12N 2501/2315* (2013.01); *C12N 2501/2321* (2013.01); *C12N 2502/1121* (2013.01)

(58) Field of Classification Search
None
See application file for complete search history.

(56) References Cited

U.S. PATENT DOCUMENTS

| | | | |
|---|---|---|---|
| 6,447,765 | B1 | 9/2002 | Horwitz |
| 6,759,035 | B2 | 7/2004 | Horwitz |
| 6,803,036 | B1 | 10/2004 | Horwitz |
| 7,270,810 | B2 | 9/2007 | Reisner et al. |
| 8,974,779 | B2 | 3/2015 | Reisner et al. |
| 9,421,228 | B2 | 8/2016 | Reisner et al. |
| 9,738,872 | B2 | 8/2017 | Reisner et al. |
| 9,833,482 | B2 | 12/2017 | Reisner et al. |
| 9,987,354 | B2 | 6/2018 | Fraser et al. |
| 9,993,548 | B2 | 6/2018 | Maldonado |
| 10,039,822 | B2 | 8/2018 | Altreuter et al. |
| 10,155,818 | B2 | 12/2018 | Seibert et al. |
| 10,280,226 | B2 | 5/2019 | Seibert et al. |
| 10,369,172 | B2 | 8/2019 | Reisner et al. |
| 10,751,368 | B2 | 8/2020 | Reisner et al. |
| 2002/0182211 | A1 | 12/2002 | Peach et al. |
| 2003/0003083 | A1 | 1/2003 | Reisner et al. |
| 2003/0022836 | A1 | 1/2003 | Larsen et al. |
| 2003/0049235 | A1 | 3/2003 | Reisner |
| 2003/0083246 | A1 | 5/2003 | Cohen et al. |
| 2004/0022787 | A1 | 2/2004 | Cohen et al. |
| 2004/0136972 | A1 | 7/2004 | Reisner et al. |

(Continued)

FOREIGN PATENT DOCUMENTS

| | | |
|---|---|---|
| CN | 103930130 | 7/2014 |
| CN | 104470542 | 3/2015 |

(Continued)

OTHER PUBLICATIONS

Stanciu et al., 2000, Isolation of T-Cell Subsets by Magnetic Cell Sorting (MACS). pp. 133-141.*

(Continued)

*Primary Examiner* — Amy E Juedes

(57) ABSTRACT

A method of generating an isolated population of cells comprising anti-third party cells having a central memory T-lymphocyte (Tcm) phenotype, the cells being tolerance-inducing cells and/or endowed with anti-disease activity, and capable of homing to the lymph nodes following transplantation is disclosed. The method comprising: (a) contacting peripheral blood mononuclear cells (PBMC) with a third party antigen or antigens in the presence of IL-21 so as to allow enrichment of antigen reactive cells; and (b) culturing the cells resulting from step (a) in the presence of IL-21, IL-15 and IL-7 in an antigen free environment so as to allow proliferation of cells comprising the central memory T-lymphocyte (Tcm) phenotype.

18 Claims, 37 Drawing Sheets
(37 of 37 Drawing Sheet(s) Filed in Color)

(56) References Cited

U.S. PATENT DOCUMENTS

| | | |
|---|---|---|
| 2005/0123539 A1 | 6/2005 | Rusnak |
| 2005/0214313 A1 | 9/2005 | Peach et al. |
| 2006/0269973 A1 | 11/2006 | Yee |
| 2007/0009511 A1 | 1/2007 | Hagerty et al. |
| 2007/0264274 A1 | 11/2007 | Reisner et al. |
| 2008/0131415 A1 | 6/2008 | Riddell et al. |
| 2008/0160022 A1 | 7/2008 | Larsen et al. |
| 2008/0279817 A1 | 11/2008 | Skak |
| 2009/0022730 A1 | 1/2009 | Raulf et al. |
| 2009/0041769 A1 | 2/2009 | Peach et al. |
| 2009/0041790 A1 | 2/2009 | Rusnak |
| 2009/0068203 A1 | 3/2009 | Rusnak |
| 2009/0232774 A1 | 9/2009 | Reisner |
| 2010/0022627 A1 | 1/2010 | Scherer |
| 2010/0041602 A1 | 2/2010 | Hagerty et al. |
| 2010/0049935 A1 | 2/2010 | Pichumani et al. |
| 2010/0166756 A1 | 7/2010 | Cohen et al. |
| 2010/0183612 A1 | 7/2010 | Peach et al. |
| 2010/0255009 A1 | 10/2010 | Siemionov |
| 2011/0212071 A1 | 9/2011 | Reisner et al. |
| 2013/0171108 A1 | 7/2013 | Reisner et al. |
| 2013/0183322 A1 | 7/2013 | Reisner et al. |
| 2014/0120622 A1 | 5/2014 | Gregory et al. |
| 2014/0212398 A1 | 7/2014 | Reisner et al. |
| 2014/0271581 A1 | 9/2014 | Hyde et al. |
| 2014/0314795 A1 | 10/2014 | Riddell et al. |
| 2016/0354410 A1 | 12/2016 | Reisner et al. |
| 2017/0216356 A1 | 8/2017 | Eshhar et al. |
| 2018/0200300 A1 | 7/2018 | Reisner et al. |
| 2018/0207247 A1 | 7/2018 | Reisner et al. |
| 2018/0207272 A1 | 7/2018 | Reisner et al. |
| 2019/0091266 A1 | 3/2019 | Reisner et al. |
| 2019/0316087 A1 | 10/2019 | Reisner et al. |
| 2019/0338247 A1 | 11/2019 | Reisner et al. |

FOREIGN PATENT DOCUMENTS

| | | |
|---|---|---|
| EP | 2753351 | 3/2013 |
| JP | 2008-521406 | 6/2008 |
| JP | 2013-537187 | 9/2013 |
| JP | 2014-526244 | 7/2014 |
| JP | 2014-510108 | 10/2014 |
| WO | WO 01/49243 | 7/2001 |
| WO | WO 02/43651 | 6/2002 |
| WO | WO 02/102971 | 12/2002 |
| WO | WO 2005/067956 | 7/2005 |
| WO | WO 2005/092380 | 10/2005 |
| WO | WO 2006/041763 | 4/2006 |
| WO | WO 2006/065495 | 6/2006 |
| WO | WO 2007/023491 | 3/2007 |
| WO | WO 2009/053109 | 4/2009 |
| WO | WO 2010/049935 | 5/2010 |
| WO | WO 2011/053223 | 5/2011 |
| WO | WO 2011/140170 | 11/2011 |
| WO | WO 2012/032525 | 3/2012 |
| WO | WO 2012/032526 | 3/2012 |
| WO | WO 2012/129514 | 9/2012 |
| WO | WO 2013/035099 | 3/2013 |
| WO | WO 2014/031687 | 2/2014 |
| WO | WO 2014/039044 | 3/2014 |
| WO | WO 2014/059173 | 4/2014 |
| WO | WO 2014/152177 | 9/2014 |
| WO | WO 2017/009852 | 1/2017 |
| WO | WO 2017/009853 | 1/2017 |
| WO | WO 2017/203520 | 11/2017 |
| WO | WO 2018/134824 | 7/2018 |

OTHER PUBLICATIONS

Miltenyi Biotech product information for CD8+ T cell isolation kit, 2016, pp. 1-2.*
Hacque et al., 2007, BLood. vol. 110: 1123-1131.*
Current Protocols in Immunology (2002), Yssel et al., 7.19.1-7.19.12.*
Notice of Grounds for Rejection dated Nov. 29, 2018 From the Korea Intellectual Property Office Re. Application No. 10-2014-7009267 and Its Translation Into English. (11 Pages).
Official Action dated Jun. 19, 2018 From the US Patent and Trademark Office Re. U.S. Appl. No. 15/242,666. (54 pages).
Carrio et al. "Initial Antigen Encounter Programs CD8+ TCells Competent to Develop into Memory Cells That Are Activated in an Antigen-Free, IL-7- and IL-15-Rich Environment", The Journal of Immunology, 172: 7315-7323, 2004.
Doiron et al. "The Role of T Cells in Peripheral Blood Mononuclear Cells", Human Tissue Sample Blog, pp. 1-4, 2016.
Klinger et al. "Cyclical Expression of L-Selectin (CD62L) by Recirculating T Cells", International Immunology, 21(4): 443-455, Apr. 1, 2009.
van Leeuwen et al. "Proliferation Requirements of Cytomegalovirus-Specific, Effector-Type Human CD8+ T Cells", The Journal of Immunology, 169: 5838-5843, 2002.
Requisition by the Examiner dated Jul. 30, 2018 From the Innovation, Science and Economic Development Canada, Canadian Intellectual Property Office Re. Application No. 2,848,121. (5 Pages).
Official Action dated Jul. 17, 2019 From the US Patent and Trademark Office Re. U.S. Appl. No. 15/744,905. (43 pages).
Neeson et al. "Ex vivo culture of chimeric antigen receptor T cells generates functional COB+ T cells with effector and central memory-like phenotype", Gene Therapy, 17: 1105-1116, 2010.
Restriction Official Action dated Jan. 7, 2018 From the US Patent and Trademark Office Re. U.S. Appl. No. 15/744,881. (8 pages).
Restriction Official Action dated Feb. 21, 2019 From the US Patent and Trademark Office Re. U.S. Appl. No. 15/744,905. (7 pages).
Examination Report Under Sections 12 & 13 of the Patents Act, 1970 and the Patents Rules, 2003 dated Jan. 10, 2019 From the Government of India, Intellectual Property India, Patents, Designs, Trade Marks, Geographical Indications Re. Application No. 577/MUMNP/2014. (7 Pages).
Official Action dated Sep. 19, 2019 From the US Patent and Trademark Office Re. U.S. Appl. No. 15/744,881. (46 Pages).
Lask et al. "A New Approach For Eradication of Residual Lymphoma Cells By Host Nonreactive Anti-Third-Party Central Memory CD8 T Cells", Blood, 121(15): 3033-3040, Published Online Feb. 27, 2013.
Ophir et al. "Induction of Transplantation Tolerance in Haploidenical Transplantation Under Reduced Intensity Conditioning: The Role of Ex-Vivo Generated Donor Cos+ T Cells with Central Memory Phenotype", Best Practice & Research Clinical Haematology 24(3): 393--401, Jul. 13, 2011.
Ophir et al. "Murine Anti-Third-Party Central-Memory CD8+ T Cells Promote Hematopoietic Chimerism Under Mild Conditioning: Lymph-Node Sequestration and Deletion of Anti-Donor T Cells", Blood. 121(7): 1220-1228, Prepublished online Dec. 5, 2012.
Or-Geva et al. "Towards 'Off-The-Shelf Genetically Modified T Cells: Prolonging Functional Engraftment in Mice by CD8 Veto T Cells", Leukemia, 32(4):1039-1041, Published Online Nov. 20, 2017.
International Preliminary Report on Patentability dated Jan. 25, 2018 From the International Bureau of WIPO Re. Application No. PCT/IL2016/050775. (7 Pages).
Notification of Office Action and Search Report dated Feb. 26, 2019 From the National Intellectual Property Administration of the People's Republic of China Re. Application No. 201610307275.9 and Its Translation Into English. (20 Pages).
International Preliminary Report on Patentability dated Aug. 1, 2019 From the International Bureau of WIPO Re. Application No. PCT/IL2018/050071. (10 Pages).
Restriction Official Action dated Dec. 22, 2017 From Trademark Office Re. U.S. Appl. No. 15/242,666. (8 page).
Applicant-Initiated Interview Summary dated May 4, 2015 From the US Patent and Trademark Office Re. U.S. Appl. No. 13/821,255.
Communication Pursuant to Article 94(3) EPC dated Jun. 4, 2014 From the European Patent Office Re. Application No. 09764302.7.
Communication Pursuant to Article 94(3) EPC dated Dec. 14, 2012 From the European Patent Office Re. Application No. 09764302.7.
Communication Pursuant to Article 94(3) EPC dated Oct. 21, 2015 From the European Patent Office Re. Application No. 12769743.1.

(56) References Cited

OTHER PUBLICATIONS

Communication Pursuant to Article 94(3) EPC dated Jan. 24, 2014 From the European Patent Office Re. Application No. 11773345.6.
Communication Pursuant to Article 94(3) EPC dated Jan. 26, 2015 From the European Patent Office Re. Application No. 12769743.1.
Communication Pursuant to Article 94(3) EPC dated Jan. 27, 2014 From the European Patent Office Re. Application No. 11773325.3.
Communication Pursuant to Rule 114(2) EPC (Third Party Observation) dated Sep. 26, 2014 From the European Patent Office Re. Application No. 12769743.1.
Decision on Rejection dated Dec. 2, 2015 From The State Intellectual Property Office of the People's Republic of China Re. Application No. 201180053858.9 and Its Translation Into English.
Examination Report dated Feb. 1, 2017 From the Instituto Mexicano de la Propiedad Industrial, IMPI, Direccion Divisional de Patentes Re. Application No. MX/a/2013/002668 and Its Translation Into English. (8 Pages).
Examination Report dated Feb. 2, 2016 From the Intellectual Property Office of Singapore Re. Application No. 11201400513P.
Examination Report dated Oct. 15, 2015 From the Intellectual Property Office of Singapore Issued by the Austrian Patent Office Re. Application No. 201301743-9.
Examination Report dated Sep. 25, 2017 From the Institute Mexicano de la Propiedad Industrial, IMPI, Direccion Divisional de Patentes Re. Application No. MX/a/2013/002668 and Its Translation Into English. (16 Pages).
Examination Report dated Jul. 28, 2017 From the Australian Government, IP Australia Re. Application No. 2012305931. (3 Pages).
Examination Report dated Mar. 28, 2016 From the Government of India, Patent Office, Intellectual Property Building Re. Application No. 905/MUMNP/2011.
Examination Report dated Jul. 29, 2016 From the Institute Mexicano de la Propiedad industrial, IMPI, Direccion Divisional de Patentes Re. Application No. MX/a/2013/002668 and Its Translation Into English.
International Preliminary Report on Patentability dated May 12, 2011 From the International Bureau of WIPO Re. Application No. PCT/IL2009/001014.
International Preliminary Report on Patentability dated Mar. 20, 2014 From the International Bureau of WIPO Re. Application No. PCT/IL2012/050354.
International Preliminary Report on Patentability dated Mar. 21, 2013 From the International Bureau of WIPO Re. Application No. PCT/IL2011/000726.
International Preliminary Report on Patentability dated Mar. 21, 2013 From the International Bureau of WIPO Re. Application No. PCT/IL2011/000727.
International Search Report and the Written Opinion dated Mar. 7, 2012 From the International Searching Authority Re. Application No. PCT/IL2011/000727.
International Search Report and the Written Opinion dated Feb. 16, 2010 From the International Searching Authority Re. Application No. PCT/IL2009/001014.
International Search Report and the Written Opinion dated Oct. 19, 2016 From the International Searching Authority Re. Application No. PCT/IL2016/050774.
International Search Report and the Written Opinion dated Oct. 19, 2016 From the International Searching Authority Re. Application No. PCT/IL2016/050775.
International Search Report and the Written Opinion dated Jun. 27, 2012 From the International Searching Authority Re. Application No. PCT/IL2011/000726.
International Search Report and the Written Opinion dated Jan. 28, 2013 From the International Searching Authority Re. Application No. PCT/IL2012/050354.
Notice Of Allowance dated Apr. 11, 2017 From the US Patent and Trademark Office Re. U.S. Appl. No. 13/126,472. (34 pages).
Notice of Reason for Rejection dated Jul. 1, 2016 From the Japanese Patent Office Re. Application No. 2014-529143 and Its Translation Into English.
Notice of Reason for Rejection dated Aug. 4, 2015 From the Japanese Patent Office Re. Application No. 2013-527738 and Its Translation Into English.
Notification of Lack of Unity dated Feb. 21, 2017 From the Federal Service for Intellectual Property, Rospatent, Federal State Budgetary Institution, Federal Institute of industrial Property, Patents and Trademarks of the Russion Federation Re. Application No. 2014110897 and Its Translation Into English. (8 Pages).
Notification of Office Action and Search Report dated Jan. 23, 2015 From the State Intellectual Property Office of the People's Republic of China Re. Application No. 201280054739.X.
Office Action dated Nov. 3, 2016 From the Israel Patent Office Re. Application No. 231397 and Its Translation Into English. (7 Pages).
Office Action dated Oct. 12, 2015 From the Israel Patent Office Re. Application No. 225102 and Its Translation Into English.
Office Action dated May 14, 2014 From the Israel Patent Office Re. Application No. 212587 and Its Translation Into English.
Office Action dated Apr. 15, 2013 From the Israel Patent Office Re. Application No. 212587 and Its Translation Into English.
Office Action dated Mar. 18, 2015 From The State Intellectual Property Office of the People's Republic of China Re. Application No. 201180053858.9 and Its Translation Into English.
Office Action dated Sep. 23, 2015 From the State Intellectual Property Office of the People's Republic of China Re. Application No. 201280054739.X and Its Translation Into English.
Office Action dated Apr. 29, 2014 From The State Intellectual Property Office of the People's Republic of China Re. Application No. 201180053858.9 and Its Translation Into English.
Official Action dated Aug. 1, 2013 From the US Patent and Trademark Office Re. U.S. Appl. No. 13/126,472.
Official Action dated Jun. 1, 2017 From the US Patent and Trademark Office Re. U.S. Appl. No. 14/343,053. (27 pages).
Official Action dated Oct. 3, 2016 From the US Patent and Trademark Office Re. U.S. Appl. No. 13/126,472.
Official Action dated Oct. 7, 2016 From the US Patent and Trademark Office Re. U.S. Appl. No. 14/343,053.
Official Action dated May 8, 2014 From the US Patent and Trademark Office Re. U.S. Appl. No. 13/126,472.
Official Action dated Feb. 12, 2016 From the US Patent and Trademark Office Re. U.S. Appl. No. 14/343,053.
Official Action dated Nov. 19, 2015 From the US Patent and Trademark Office Re. U.S. Appl. No. 13/126,472.
Official Action dated Dec. 23, 2016 From the US Patent and Trademark Office Re. U.S. Appl. No. 14/343,053. (17 pages).
Official Action dated Mar. 23, 2015 From the US Patent and Trademark Office Re. U.S. Appl. No. 13/821,255.
Official Action dated Jul. 24, 2014 From the US Patent and Trademark Office Re. U.S. Appl. No. 13/821,255.
Patent Examination Report dated Aug. 23, 2016 From the Australian Government, IP Australia Re. Application No. 2012305931.
Restriction Official Action dated Nov. 5, 2013 From the US Patent and Trademark Office Re. U.S. Appl. No. 13/821,255.
Restriction Official Action dated Aug. 14, 2014 From the US Patent and Trademark Office Re. U.S. Appl. No. 13/821,269.
Restriction Official Action dated Oct. 20, 2015 From the US Patent and Trademark Office Re. U.S. Appl. No. 14/343,053.
Search Report and Written Opinion dated Oct. 10, 2014 From the Intellectual Property Office of Singapore Re. Application No. 11201400513P.
Search Report dated Apr. 29, 2014 From The State Intellectual Property Office of the People's Republic of China Re. Application No. 201180053858.9 and Its Translation Into English.
Translation dated Feb. 8, 2015 of Notification of Office Action and Search Report Dated Jan. 23, 2015 From the State Intellectual Property Office of the People's Republic of China Re. Application No. 201280054739.X.
Translation of Office Action dated Dec. 27, 2012 From the State Intellectual Property Office of the People's Republic of China Re. Application No. 200980153053.4.
Translation of Search Report dated Dec. 27, 2012 From the State Intellectual Property Office of the People's Republic of China Re. Application No. 200980153053.4.

(56) References Cited

OTHER PUBLICATIONS

Written Opinion and Search Report dated Feb. 28, 2014 From the Intellectual Property Office of Singapore Issued by the Austrian Patent Office Re. Application No. 201301743-9.

Written Opinion dated Jun. 11, 2015 From the Intellectual Property Office of Singapore Re. Application No. 11201400513P.

Written Opinion dated Feb. 17, 2015 From the Intellectual Property Office of Singapore Issued by the Austrian Patent Office Re. Application No. 201301743-9.

Albrecht et al. "IL-21-Treated Naive CD45RA+ CD8+ T Cells Repressant A Reliable Source for Producing Leukemia-Reactive Cytotoxic T Lymphocytes With High Proliferative Potential and Early Differentiation Phenotype", Cancer Immunology, Immunotherapy: CII, XP002689103, 60(2): 235-248, Feb. 2011. Abstract.

Arditti et al. "Eradication of B-CLL by Autologous and Allogeneic Host Nonreactive Anti-Third-Party CTLs", Blood, 105(8): 3365-3371, Apr. 15, 2005.

Aversa et al. "Full Haplotype-Mismatched Hematopoietic Stem-Cell Transplantation: A Phase II Study in Patients With Acute Leukemia at High Risk of Relapse", Journal of Clinical Oncology, 23(15): 3447-3454, May 20, 2005.

Aversa et al. "Successful Engraftment of T-Cell-Depleted Haploidentical 'Three-Loci' Incompatible Transplants in Leukemia Patients by Addition of Recombinant Human Granulocyte Colony-Stimulating Factor-Mobilized Peripheral Blood Progenitor Cells to Bone Marrow Inoculum", Blood, 84(4): 3948-3955, Dec. 1, 1994.

Aversa et al. "Treatment of High-Risk Acute Leukemia With T-Cell-Depleted Stem Cells From Related Donors With One Fully Mismatched HLA Haplotype", The New England Journal of Medicine, 339(17): 1186-1193, Oct. 22, 1998.

Aviner et al. "Large-Scale Preparation of Human Anti-Third-Party Veto Cytotoxic T Lymphocytes Depleted of Graft-Versus-Host Reactivity: A New Source for Graft Facilitating Cells in Bone Marrow Transplantation", Human Immunology, 66(6): 644-652, Jun. 30, 2005.

Bachar-Lustig et al. "Anti-Third-Party Veto CTLs Overcome Rejection of Hematopoietic Allografts: Synergism With Rapamycin and BM Cell Dose", Blood, 102(6): 1943-1950, Sep. 15, 2003.

Bachar-Lustig et al. "Megadose of T Cell-Depleted Bone Marrow Overcomes MHC Barriers in Sublethally Irradiated Mice", Nature Medicine, 1(12): 1268-1273, Dec. 1995.

Berger et al. "Adoptive Transfer of Effector CD8+ T Cells Derived from Central Memory Cells Establishes Persistent T cell Memory in Primates", The Journal of Clinical Investigation. 118(1): 294-305, Jan. 2008.

Biocompare "Human CD8+ T Cell Isolation Kit II From Miltenyi Biotec", Biocompare, pp. 1-5, Oct. 30, 2006.

Dutton et al. "T Cell Memory", Annual Review of Immunology, 16: 201-223, 1998. p. 203, 2nd Para.

Fujiwara "Adoptive Immunotherapy for Hematological Malignancies Using T Cells Gene-Modified to Express Tumor Antigen-Specific Receptors", Pharmaceuticals, 7(12): 1049-1068, Dec. 15, 2014.

Gilham et al. "Adoptive T-Cell Therapy for Cancer in the United Kingdom: A Review of Activity for the British Society of Gene and Cell Therapy Annual Meeting 2015", Human Gene Therapy, 26(5): 276-285, Published Online Apr. 10, 2015.

Gouble et al. "In Vivo Proof of Concept of Activity and Safety of UCART19, an Allogeneic 'Off-the-Shelf 'Adoptive T-Cell Immunotherapy Against CD19+ B-Cell Leukemias", Blood, 124(21): 4689, Dec. 6, 2014.

Grigg et al. "Graft-Versus-Lymphoma Effects: Clinical Review, Policy Proposal, and Immunobiology", Biology of Blood and Marrow Transplantation, 10: 579-590, 2004.

Gur et al. "Immune Regulatory Activity of CD34+ Progenitor Cells: Evidence for a Deletion-Based Mechanism Mediated by TNF-{Alpha}", Blood, 105(6): 2585-2593, Mar. 15, 2005.

Gur et al. "Tolerance Induction by Megadose Hematopoietic Progenitor Cells: Expansion of Veto Cells by Short-Term Culture of Purified Human CD34+ Cells", Blood, 99(11): 4174-4181, Jun. 1, 2002.

Handgretinger et al. "Megadose Transplantation of Purified Peripheral Blood CD34+ Progenitor Cells From HLA-Mismatched Parental Donors in Children", Bone Marrow Transplantation, 27: 777-783, 2001.

Harwerth et al. "Monoclonal Antibodies Directed to the ErbB-2 Receptor Inhibit In Vivo Tumour Cell Growth", British Journal of Cancer, 68(6): 1140-1145, Dec. 1993.

Hecht et al. "Embryonic Pig Pancreatic Tissue for the Treatment of Diabetes in a Nonhuman Primate Model", Proc. Natl. Acad. Sci. USA, PNAS, XP009122169, 106(21): 8659-8664, May 26, 2009. p. 8663, col. l, Para 2.

Ho et al. "Adoptive Therapy With CD8+ T Cells: It May Get by With A Little Help From Its Friends", the Journal of Clinical Investigation, 110(10): 1415-1417, Nov. 2002.

Huarte et al. "Ex Vivo Expansion of Tumor Specific Lymphocytes With IL-15 and IL-21 for Adoptive Immunotherapv in Melanoma", Cancer Letters, 285: 80-88, 2009. Abstract, p. 80, Left Right col. 2nd Para, Section 2.4.

Kawai et al. "HLA-Mismatched Renal Transplantation Without Maintenance Immunosuppression", The New England Journal of Medicine, XP002562461, 358(4): 353-361, Jan. 24, 2008. Abstract, p. 353-354, col. 1, Para 2, Table 1.

Lapidot et al. "Enhancement by Dimethyl Myleran of Donor Type Chimerism in Murine Recipients of Bone Marrow Allografts", Blood, 73(7): 2025-2032, May 15, 1989.

Lapidot et al. "Enhancement bv Dimethyl Myleran of Donor type Chimerism in Murine Resipients of Bone Marrow Allografts", Blood, 73(7): 2025-2032, May 15, 1989.

Lask et al. "TCR Independent Killing of B Cell Malignancies by Anti-3rd Party CTLs: Rapid Conjugate Formation Via ICAM1-LFA1 Leads to Slow Induction of Apoptosis Upon MHC-CD8 Engagement", Journal of Immunology, XP009156306, 187(4): 2006-2014, Aug. 15, 2011.

Li et al. "IL-21 Influences the Frequency, Phenotype, and Affinity of the Antigen-Specific CD8 T Cell Response", The Journal of Immunology, 175: 2261-2269. 2005. Abstract, Materials and Methods: Induction of Human Ag-Specific CD8+ T Cells.

Markley et al. "IL-7 and IL-21 Are Superior to IL-2 and IL-15 in Promoting Human T Cell-Mediated Rejection of Systematic Lymphoma in Immunodeficient Mice", Blood, XP009165652, 115(17): 3508-3519, Apr. 29, 2010. p. 3509, col. 2, Par 2.

Ophir et al. "Induction of Tolerance in Organ Recipients by Hematopoietic Stem Cell Transplantation", International Immunopharmacology, XP026088865, 9(6): 694-700, Jun. 1, 2009. Figs. 3, 6.

Ophir et al. "Induction of Tolerance to Bone Marrow Allografts by Donor-Derived Host Nonreactive Ex Vivo Induced Central Memory CD8 T Cells", Blood, XP009165643, 115(10): 2095-2104, Mar. 11, 2010. Abstract, p. 2096, col. 1, Para 2.

Ophir et al. "Induction of Transplantation Tolerance in Haploidenical Transplantation Under Reduced Intensity Conditioning: The Role of Ex-Vivo Generated Donor CD8+ T Cells With Central Memory Phenotype", Best Practice & Research Clinical Haematology. XP002829486, 24(3): 393-401, Jul. 13, 2011. p. 396, Fig. 3.

Pilat et al. "Treg-Therapy Allows Mixed Chimerism and Transplantation Tolerance Without Cytoreductive Conditioning", American Journal of Transplantation, 10: 751-762, 2010.

Rachamim et al. "Tolerance Induction by 'Megadose' Hematopoietic Transplants. Donor-Type CD34 Stem Cells Induce Potent Specific Reduction of Host anti-Donor Cytotoxic T Lymphocyte Precursors in Mixed Lymphocyte Culture", Transplantation, 65(10): 1386-1393, May 27, 1998.

Reich-Zeliger et al. "Anti-Third Party CD8+ CTLs as Potent Veto Cells: Coexpression of CD8 and FasL Is A Prerequisite", Immunity, 13: 507-515, Oct. 2000.

Reich-Zeliger et al. "Tolerance Induction by Veto CTLs in the TCR Transgenic 2C Mouse Model. I. Relative Reactivity of Different Veto Cells", The Journal of Immunology, 173(11): 6654-6659, Dec. 2004.

(56) References Cited

OTHER PUBLICATIONS

Reisner et al. "Bone Marrow Transplantation Across HLA Barriers by Increasing the Number of Transplanted Cells", Immunology Today, 16(9): 437-440, 1995.
Reisner et al. "Demonstration of Clonable Alloreactive Host T Cells in a Primate Model for Bone Marrow Transplantation", Proc. Natl. Acad. Sci. USA, 83: 4012-4015, Jun. 1986.
Reisner et al. "Stem Cell Escalation Enables HLA-Disparate Haematopoietic Transplants in Leukaemia Patients", Immunology Today, 20(8): 343-347, Aug. 1999.
Roncarolo et al. "Regulatory T-Cell Immunotherapy for Tolerance To Self Antigens and Alloantigens in Humans", Nature Reviews Immunology, 7(8): 585-598, Aug. 2007.
Santegoets et al. "In Vitro Priming of Tumor-Specific Cytotoxic T Lymphocytes Using Allogeneic Dendritic Cells Derived From the Human MUTZ-3 Cell Line", Cancer Immunol Immunother. 55(12): 1480-1490, Published Online Feb. 9, 2006.
Scandling et al. "Tolerance and Chimerism After Renal and Hematopoietic-Cell Tranplantation", The New England Journal of Medicine, XP002562462, 358(4): 362-368, Jan. 24, 2008. Abstract, p. 363-365, Fig.3, Abstract, p. 362, Para 1, 3-p. 363, Left col. Para 2, Right col. Para 2, 4, p. 365, Left col. Para 2, p. 367, Discussion, Figs.2, 3.
Sharpe et al. "Genetically Modified T Cells in Cancer Therapy: Opportunities and Challenges", Disease Models and Mechanisms, 8(4): 337-350, Apr. 2015.
Tchorsh-Yutsis et al. "Pig Embryonic Pancreatic Tissue as a Source for Transplantation in Diabetes. Transient Treatment With Anit-LFA1, Anit-CD48, and FTY720 Enables Long-Term Graft Maintenance in Mice With Only Mild Ongoing Immunosuppression", Diabetes, XP009122170, 58(7): 1585-1594, Jul. 1, 2009. Figs. 5, 7, Table 1.
Uharek et al. "Influence of Cell Dose and Graft-Versus-Host Reactivity on Rejection Rates After Allogeneic Bone Marrow Transplantation", Blood, 79(6): 1612-1621, Mar. 15, 1992.
Weninger et al. "Migratory Properties of Naive, Effector, and Memory CD8+ T Cells", Journal of Experimental Medicine, 12(6): 953-966, Oct. 1, 2001.
Wherry et al. "Lineage Relationship and Protective Immunity of Memory CD8 T Cell Subsets". Nature Immunology, XP002562463, 4(3): 225-234, Mar. 2003. p. 232-233, Figs. 1-4.
Woelfl et al. "Primed Tumor-Reactive Multifunctional CD62L+ Human CD8+ T Cells for Immunotherapy", Cancer Immunology. Immunotherapy, 60(2): 173-186, Feb. 2011.
Xie "The Development of the PBSC Transplantation", Railway Medical Journal, 29(5): 281-283, Jan. 31, 2001. & English Translation.
Yang et al. "In Vitro Generated Anti-Tumor T Lymphocytes Exhibit Distinct Subsets Mimicking In Vivo Antigen-Experienced Cells", Cancer Immunology, Immunotherapy: CII. XP009165653, 60(5): 739-749, May 2011.
Zeng et al. "Synergy of IL-21 and IL-15 in Regulating CD8+ T Cell Expansion and Function", The Journal of Experimental Medicine, 201(1): 139-148, Jan. 3, 2005.
International Search Report and the Written Opinion dated Apr. 17, 2018 From the International Searching Authority Re. Application No. PCT/IL2018/050071. (17 Pages).
Ersek et al. "Unique Patterns of CD8+ T-Cell-Mediated Organ Damage in the Act-mOVA/OT-I Model of Acute Graft-Versus-Host Disease", Cellular and Molecular Life Sciences, CMLS, XP036053921, 73(20): 3935-3947, Published Online Apr. 30, 2016.
Geva et al. "The Role of Donor-Derived Veto Cells in Nonmyeloablative Haploidentical HSCT" Bone Marrow Transplantation, XP055461528, 50(S2): S14-S20, Jun. 1, 2015. p. 16-17.
Rajawat et al. "Development of an Enhanced VETO Cells for the Generation of Alloantigen-Specific Tolerance", The Journal of Immunology, XP055462318, 196(1 Suppl.): 140.24, May 1, 2016. Abstract.
Rajawat et al. "Induction of Antigen Specific Transplantation Tolerance Using Chimeric Antigen Receptor Type T Cells Engineered to Kill Allospecific T Cells by a Gene Therapy Immunotherapeutic Approach (TRAN2P.968)", Tire Journal of Immunology, XP055462376, 194(1 Suppl.): 209.8, May 1, 2015. Abstract.
International Preliminary Report on Patentability dated Jan. 25, 2018 International Bureau of WIPO Re. Application No. PCT/IL2016/050774. (7 pages).
Official Action dated May 21, 2019 From the US Patent and Trademark Office Re. U.S. Appl. No. 15/242,666. (34 pages).
Notice of Reasons for Refusal dated Jun. 9, 2020 From the Japan Patent Office Re. Application No. 2018-501339 and Its Translation Into English. (18 Pages).
Communication Pursuant to Article 94(3) EPC dated Mar. 27, 2020 From the European Patent Office Re. Application No. 16745186.3. (7 Pages).
Official Action dated Apr. 21, 2020 from the US Patent and Trademark Office Re. U.S. Appl. No. 15/242,666. (20 pages).
Notification of Office Action dated Jun. 12, 2020 From the National Intellectual Property Administration of the People's Republic of China Re. Application No. 201610307275.9 and Its Translation Into English. (21 Pages).
Final Official Action dated May 4, 2020 from the US Patent and Trademark Office Re. U.S. Appl. No. 15/744,881. (10 pages).
Advisory Action dated Jun. 2, 2020 from the US Patent and Trademark Office Re. U.S. Appl. No. 15/744,905. (3 pages).
Communication Pursuant to Article 94(3) EPC dated Apr. 24, 2020 From the European Patent Office Re. Application No. 16750269.9. (4 Pages).
Notice of Allowance dated May 14, 2020 from the US Patent and Trademark Office Re. U.S. Appl. No. 15/873,943. (74 pages).
Bachar-Lustig et al. "Next Generation Veto Cells for Non-Myeloablative Haploidentical HSCT: Combining Anti-Viral and Graft Facilitating Activity", Experimental Transplantation: Basic Biology, Pre-Clinical Models: Poster 2. Dec. 2, 2016.
"Generation of CD 19-Chimeric Antigen Receptor Modified CDS+ T Cells Derived from Virus-Specific Central Memory T Cells", Blood, The Journal of the American Society of Hematology, 119(1): 72-82, Jan. 5, 2012.
Official Action dated Jan. 29, 2020 From the US Patent and Trademark Office Re. U.S. Appl. No. 15/744,905. (20 pages).
Figueroa et al. "Chimeric Antigen Receptor Engineering: A Right Step in the Evolution of Adoptive Cellular Immunotherapy", International Reviews of Immunology, 34:154-187, 2015.
Marcus et al. "Redirected Tumor-Specific Allogeneic T cells for Universal Treatment of Cancer", Blood, The Journal of the American Society of Hematology 118(4): 975-983, Jul. 28, 2011.
Notification of Office Action dated Apr. 12, 2021 From the National Intellectual Property Administration of the People's Republic of China Re. Application No. 201680053579.5 and Its Translation Into English. (19 Pages).
Advisory Action dated Sep. 17, 2020 from the US Patent and Trademark Office Re. U.S. Appl. No. 15/744,881. (8 pages).
Notification of Office Action and Search Report dated Aug. 21, 2020 From the State Intellectual Property Office of the People's Republic of China Re. Application No. 201680053579.5. (12 Pages).
Office Action dated Oct. 21, 2020 From the Israel Patent Office Re. Application No. 256916 and Its Translation Into English.
Official Action dated Sep. 1, 2020 from the US Patent and Trademark Office Re. U.S. Appl. No. 15/744,905. (23 pages).
Search Report and Opinion dated Sep. 14, 2020 From the Servico Publico Federal, Ministerio da Economia, Institute Nacion da Propriedade Industrial do Brasil Re. Application No. BR112013005756-4 and Its Translaton of Opinion Into English. (6 Pages).
Translation Dated Sep. 24, 2020 of Notification of Office Action and Search Report dated Aug. 21, 2020 From the State Intellectual Property Office of the People's Republic of China Re. Application No. 201680053579.5. (11 Pages).
Masopust et al. "The Role of Programming in Memory T-Cell Development", Current Opinion in Immunology, 16(2): 217-225, Apr. 2004.
Zimring "Location, Location, Location: Advancing Veto Cell Therapies" Blood 121 (7): 1069-1070, Feb. 14, 2013.

(56) References Cited

OTHER PUBLICATIONS

Notification of Office Action and Search Report dated Oct. 28, 2020 From the National Intellectual Property Office of the People's Republic of China Re. Application No. 201680053580.8 and Its Translation Into English. (41 Pages).

Search Report and Written Opinion dated Oct. 30, 2020 From the Servico Publico Federal, Ministerio da Economia, Instituto Nacional da Propriedade Industrial do Brasil Re. Application No. BR112014005355-3 and Its Translation of Written Opinion Into English. (6 Pages).

Zhao "Innovation and Prospects of Chimeric Antigen Receptor (CAR) Technique in Hematological Malignancies Immunotherapy", Chinese Master's Thesis Full-Text Database, Medical and Hygiene Technology, 11: E072-E090, May 30, 2014. & English Abstract.

Final Official Action dated Feb. 2, 2021 From the US Patent and Trademark Office Re. U.S. Appl. No. 15/242,666. (41 Pages).

Rosenberg "Adoptive Cell Transfer: A Clinical Path to Effective Cancer Immunotherapy", Nature Reviews Cancer, 8(4):299-308, Published: Apr. 2008.

Hearing Notice dated Mar. 11, 2021 From the Government of India, Intellectual Property India, Patent Office, Intellectual Property Building Re. Application No. 577/MUMNP/2014. (2 Pages).

Notification of Office Action dated Mar. 3, 2021 From the National Intellectual Property Administration of the People's Republic of China Re. Application No. 201610307275.9 and Its Translation Into English. (14 Pages).

Final Official Action dated May 6, 2021 From the US Patent and Trademark Office Re. U.S. Appl. No. 15/744,905. (28 Pages).

Notification of Office Action and Search Report dated Apr. 30, 2021 From the State Intellectual Property Office of the People's Republic of China Re. Application No. 201680053580.8 and their Translations Into English. (23 Pages).

Gattinoni et al. "A Human Memory T Cell Subset with Stem Cell-like Properties", Nature Medicine (17): 1290-1297, Sep. 18, 2011.

Wu et al. "Human Effector T cells Derived from Central Memory Cells Rather than CD8+T Cells Modified by Tumor-specific TCR Gene Transfer Possess Superior Traits for Adoptive Immunotherapy", Cancer Letters, (339):2, 195-207, Oct. 10, 2013.

Translation Dated Jun. 15, 2021 of Notice of Reasons for Refusal dated May 25, 2021 From the Japan Patent Office Re. Application No. 2018-501339. (9 Pages).

Yessel et al. "Generation and Maintenance of Cloned Human T Cell Lines"; Current Protocol in Immunology, 7.19.1-7.19.12, 2002.

Communication Pursuant to Article 94(3) EPC dated Oct. 14, 2021 From the European Patent Office Re. Application No. 16745186.3. (5 Pages).

\* cited by examiner

FIG. 4A
| Day of Culture | | 0 | 7.5 | 10.5 | 12.5 |
|---|---|---|---|---|---|
| CD8+CD3+ | AVG | 94.1 | 94.3 | 93.0 | 94.8 |
| | SE | 0.5 | 1.1 | 1.6 | 1.2 |
| | n | 8 | 5 | 4 | 2 |
| CD56+ CD3- | AVG | 0.2 | 1.1 | 1.4 | 1.2 |
| | SE | 0.0 | 0.6 | 0.5 | * |
| | n | 2 | 6 | 3 | 1 |
| CD56+CD3+ | AVG | * | 3.4 | 4.7 | 2.6 |
| | SE | * | 1.5 | 3.6 | * |
| | n | * | 3.0 | 2.0 | 1.0 |
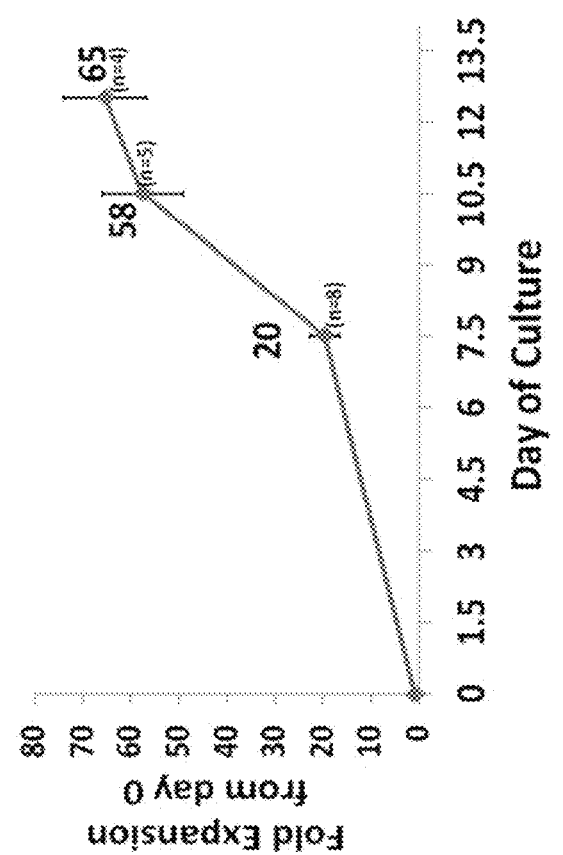
FIG. 4C
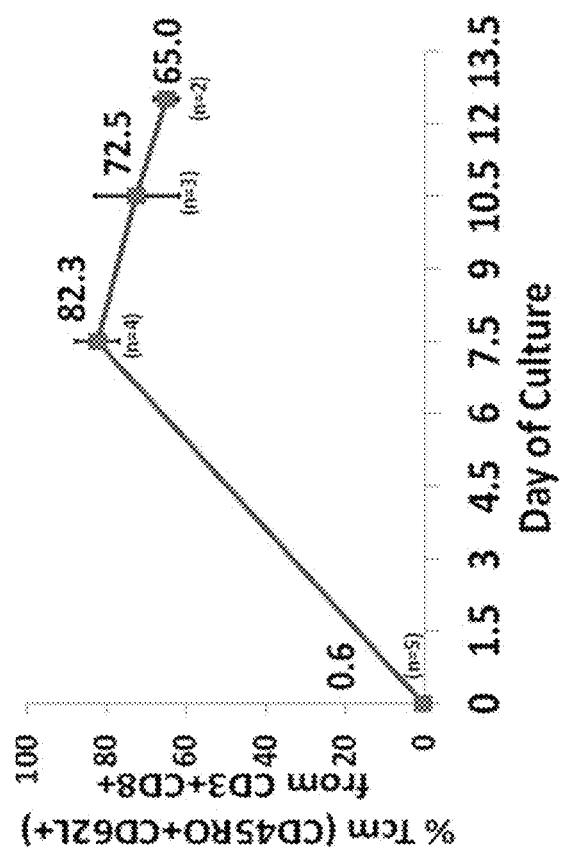
FIG. 4B

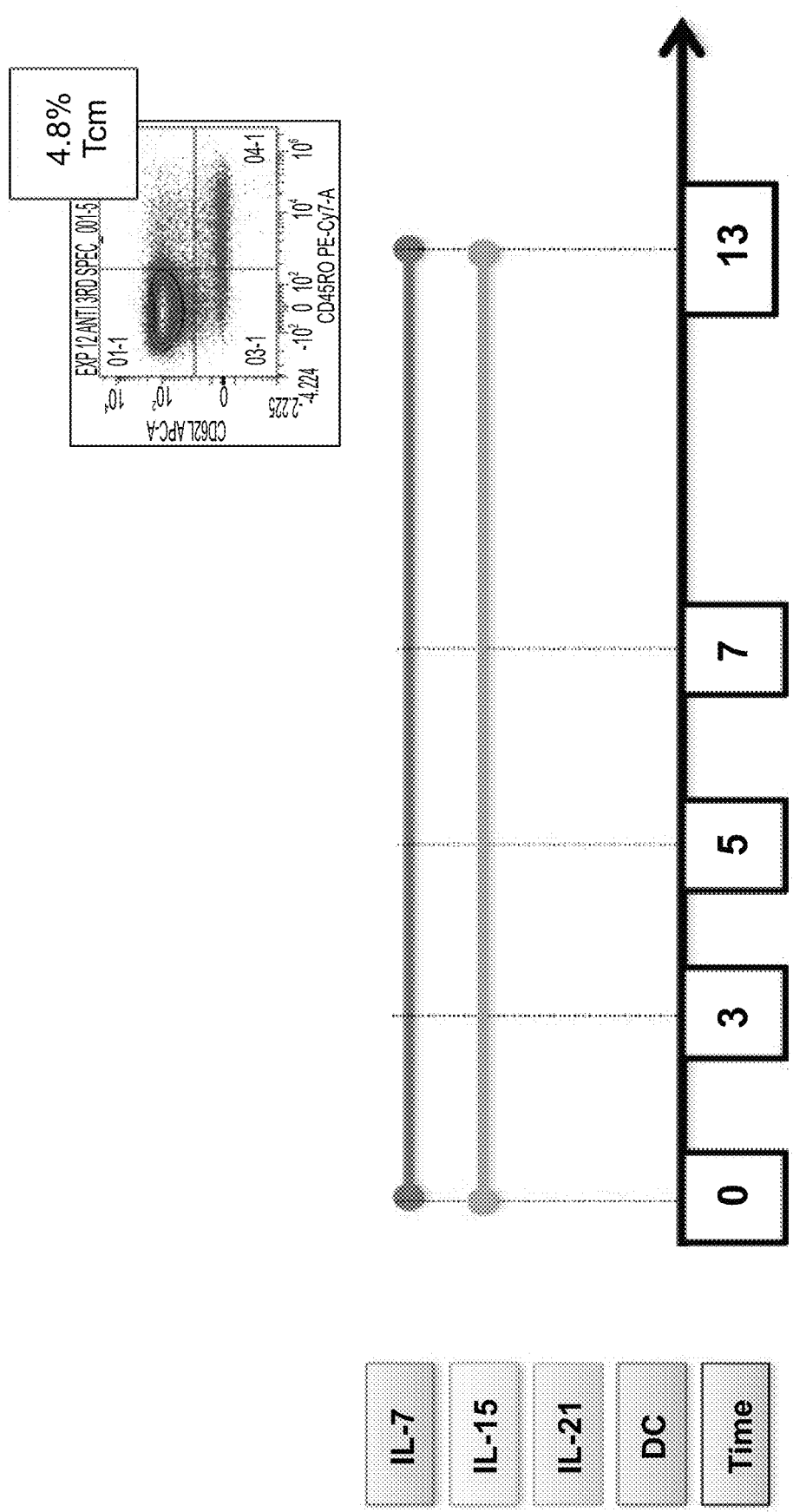

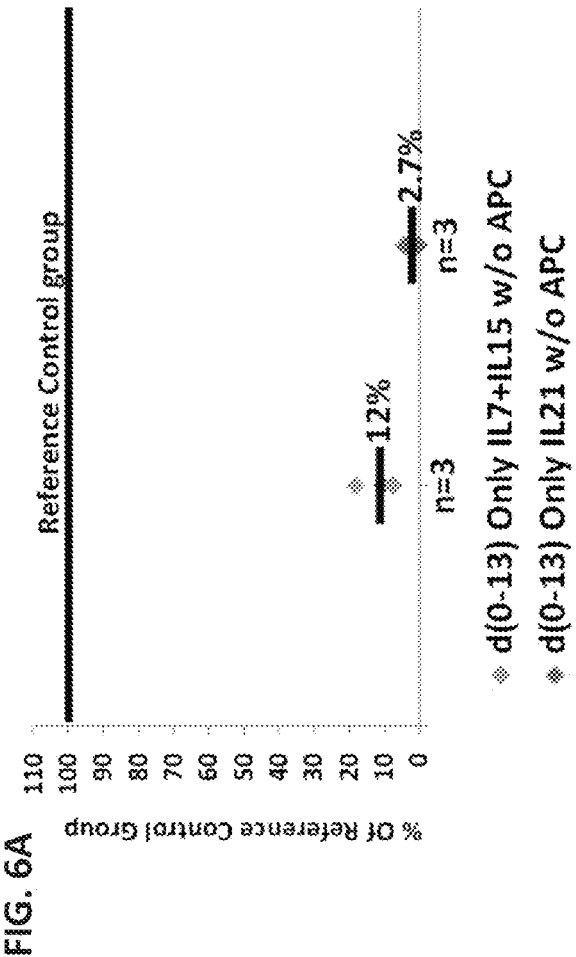
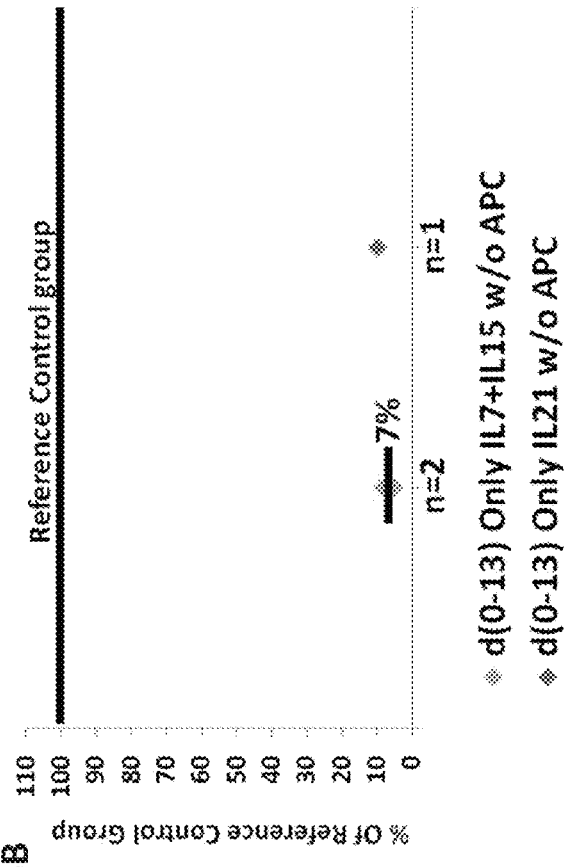
FIG. 6A
FIG. 6B

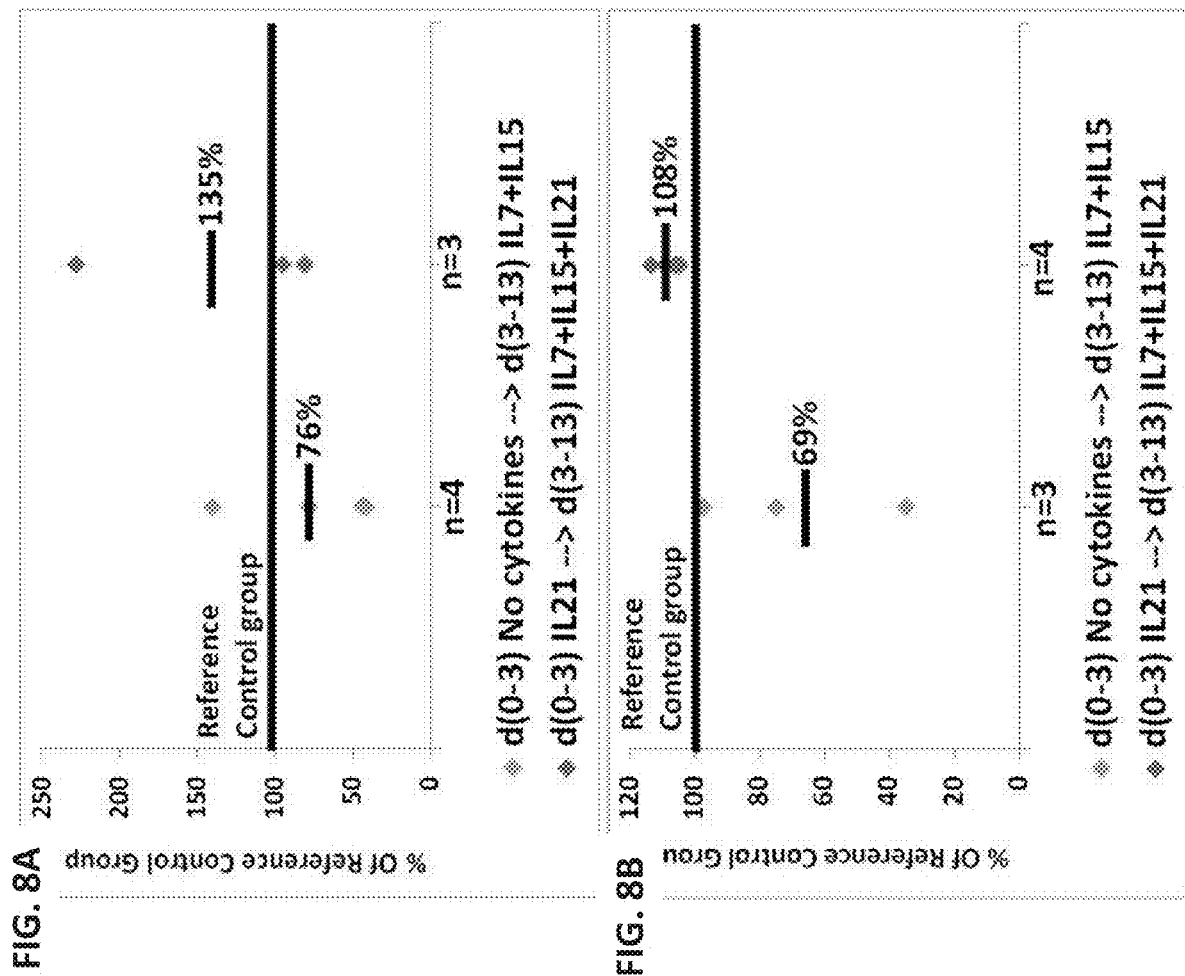

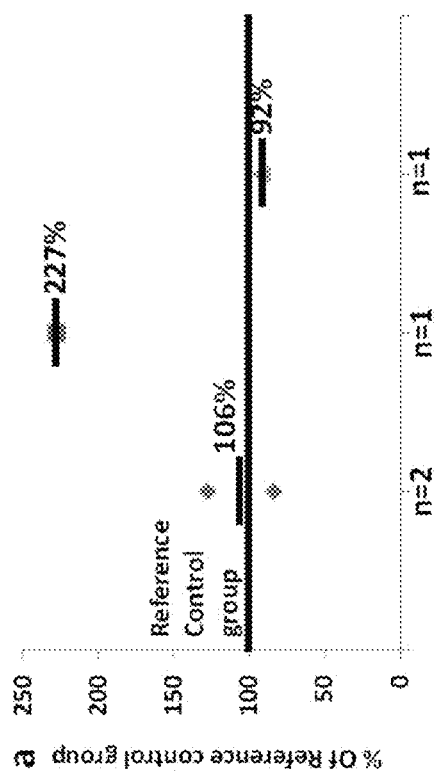
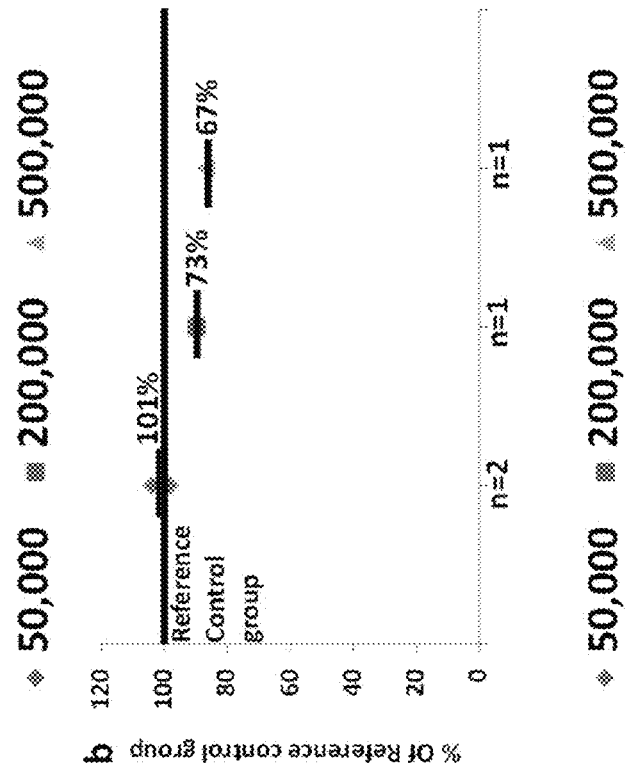
FIG. 9A
FIG. 9B

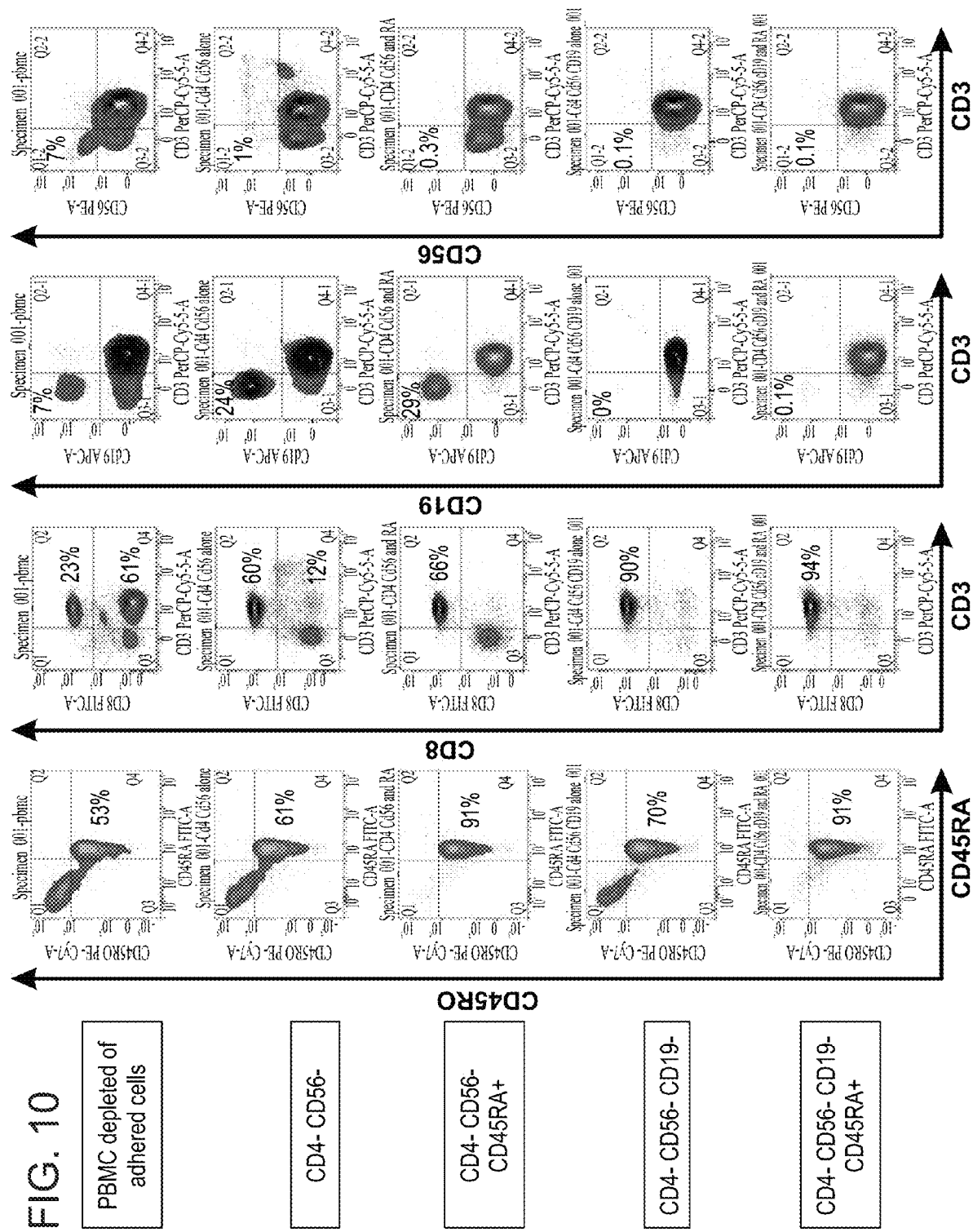

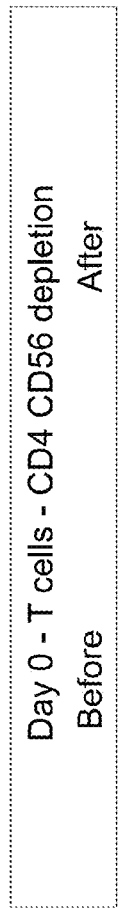
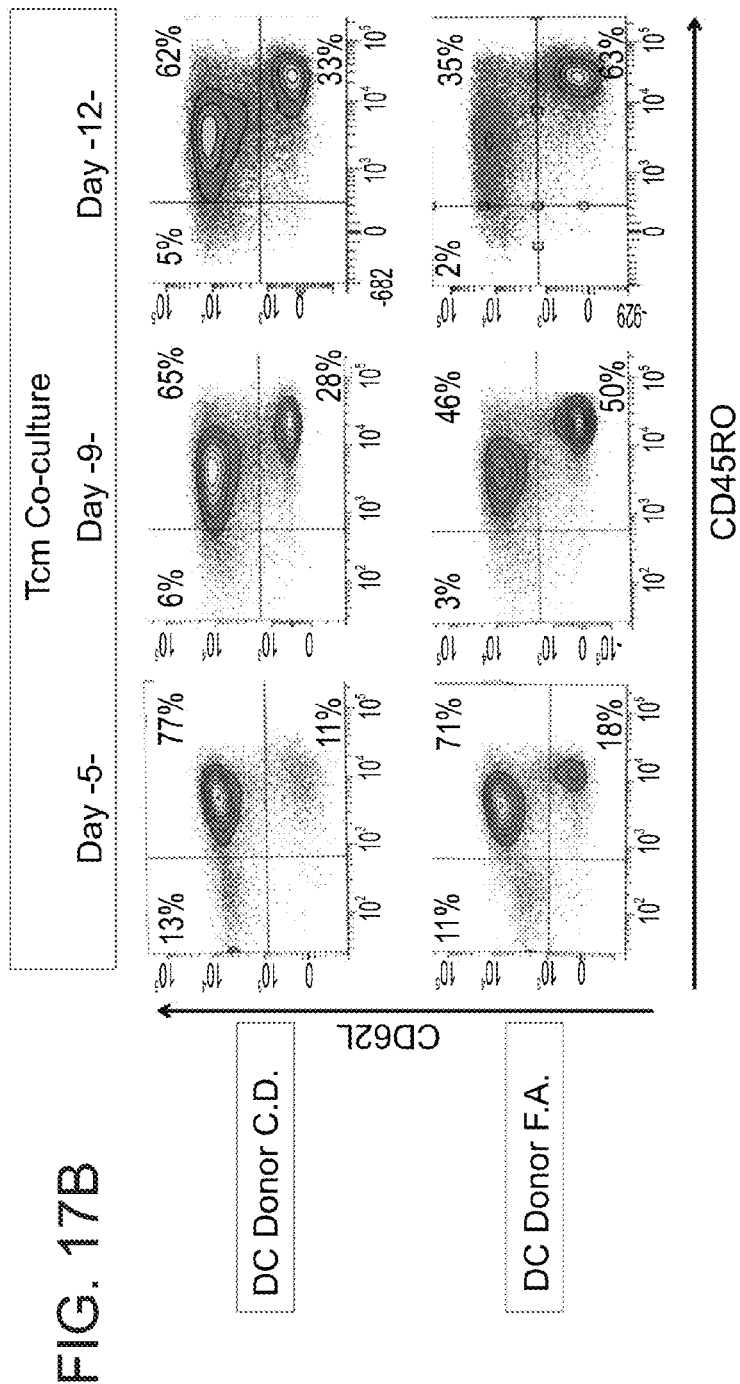
FIG. 17A
FIG. 17B

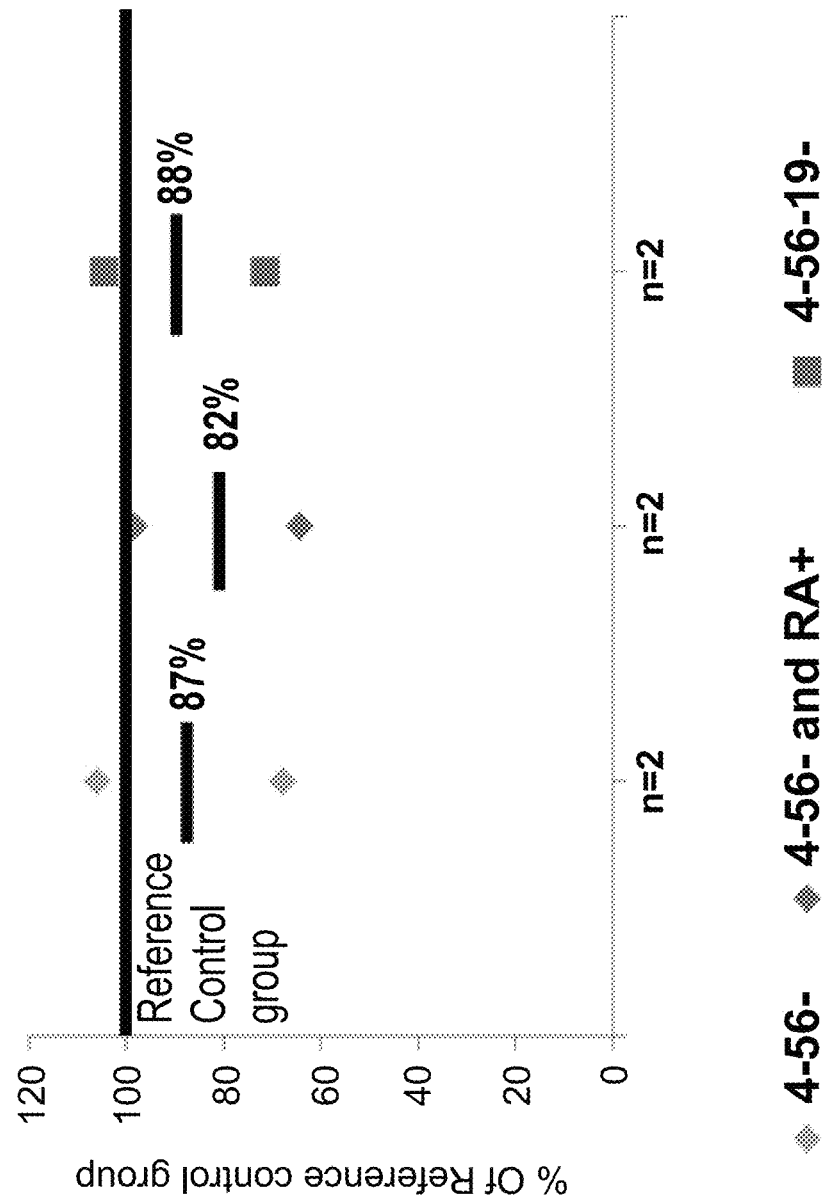

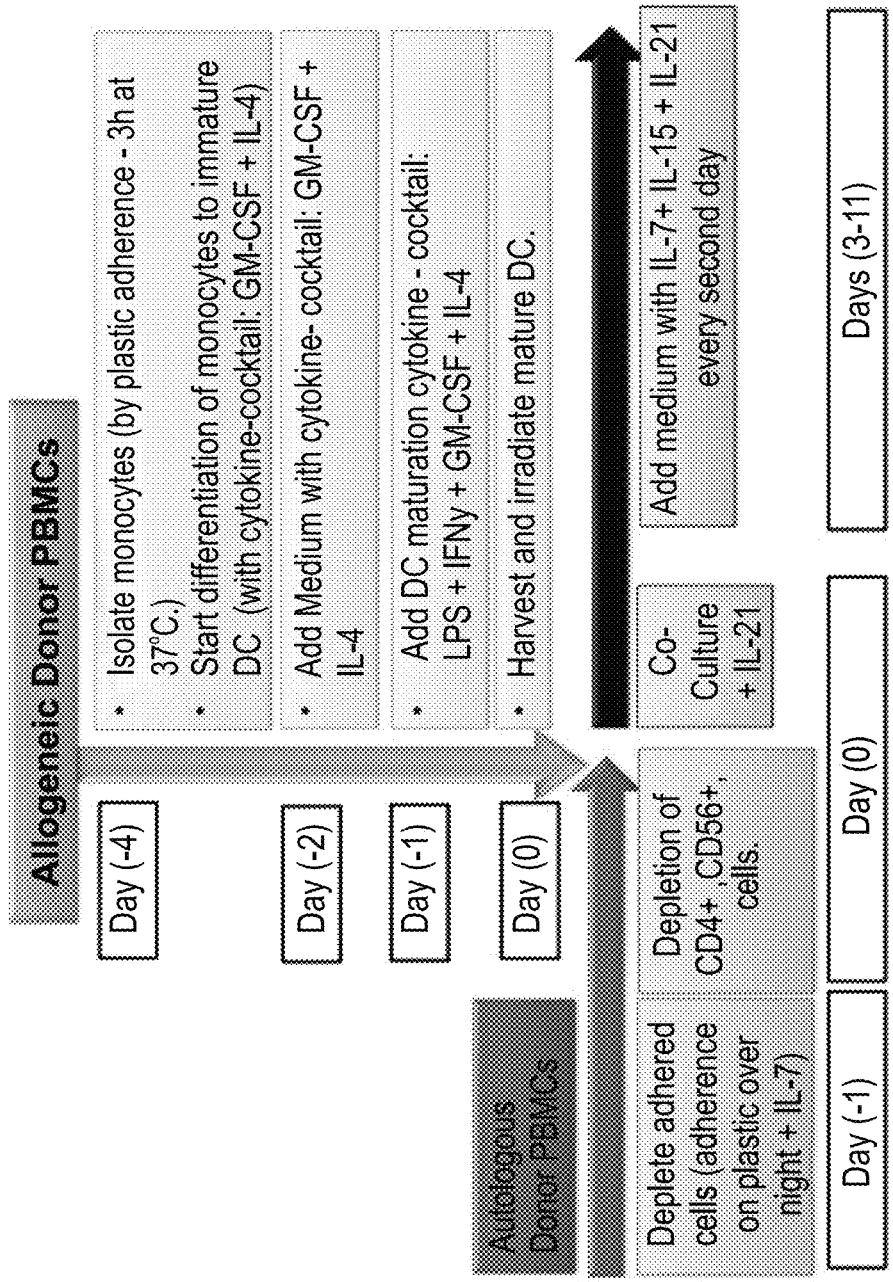

ANTI THIRD PARTY CENTRAL MEMORY T CELLS, METHODS OF PRODUCING SAME AND USE OF SAME IN TRANSPLANTATION AND DISEASE TREATMENT

RELATED APPLICATIONS

This application is a division of U.S. patent application Ser. No. 14/343,053 filed on Mar. 6, 2017, which is a National Phase of PCT Patent Application No. PCT/IL2012/050354 having International Filing Date of Sep. 6, 2012, which claims the benefit of priority under 35 USC § 119(e) of U.S. Provisional Patent Application No. 61/532,172 filed on Sep. 8, 2011. The contents of the above applications are all incorporated by reference as if fully set forth herein in their entirety.

FIELD AND BACKGROUND OF THE INVENTION

The present invention, in some embodiments thereof, relates to tolerance inducing and/or graft versus leukemia reactive anti-third party cells comprising central memory T-lymphocyte phenotype and, more particularly, but not exclusively, to methods of generating same and to the use of same in transplantation and in disease treatment.

Bone marrow (BM) transplantation offers a curative treatment for many patients with hematological malignancies and other hematological disorders. However, the BM graft contains donor T cells which respond to the host antigens (Ags) and cause multi-system graft-versus-host disease (GVHD). In the early 80's bone marrow transplant (BMT), without the deleterious effect of GVHD, was demonstrated in the haploidentical (three HLA loci mismatched) settings, in severe combined immunodeficiency (SCID) patients. The problem of GVHD, which is almost uniformly lethal in such settings, was completely prevented by T cell depletion.

However, in leukemia patients, the clinical outcome of T cell depleted BM was disappointing, as the benefit of GVHD prevention was offset by a markedly increased rate of graft rejection. The rejection was shown to be mediated by radiochemotherapy resistant host derived T cells [Reisner et al., Proc Natl Acad Sci USA. (1986) 83:4012-4015]. One way to overcome this problem is to perform BMT following supra-lethal conditioning and functional inactivation of host T cells using immunosuppressive drugs. Nevertheless, this strategy is hampered by opportunistic infections due to slow immune reconstitution and considerable toxicities of the immunosuppressants.

While in high risk leukemia patients such transplant-related mortality can be acceptable, it would be intolerable if applied to patients with a long life expectancy. Therefore, the use of reduced intensity conditioning, with less severe immune ablation, to enable engraftment of T-depleted BM (TDBM) graft, which is associated with reduced risk for GVHD, is warranted. The establishment of donor type chimerism under such reduced conditioning represents a most desirable goal in transplantation biology, as it is generally associated with durable tolerance towards cells or tissues from the original donor. Yet, the marked levels of host immune cells surviving the mild preparatory regimens, represents a difficult barrier for the engraftment of donor cells.

One approach to overcome rejection of allogeneic TDBM made use of large cell doses. It was first demonstrated in rodent models that a "megadose" of TDBM transplant can overcome T cell mediated graft rejection [Lapidot et al., Blood (1989) 73:2025-2032; Bachar-Lustig et al., Nat Med. (1995) 1:1268-1273; Uharek et al., Blood (1992) 79:1612-1621]. However, a significant increase in the BM inoculum has been difficult to achieve in humans. To overcome this problem granulocytes colony stimulating factor (G-CSF), which facilitates mobilization of hematopoietic stem cells (HSCs, CD34+ cells in humans) from the BM, has been used to increase the yield of HSCs collected from the blood and T cell depleted HSCs were supplemented to the conventional TDBM [Aversa et al., N Engl J Med. (1998) 339:1186-1193; Aversa et al., J Clin Oncol. (2005) 23:3447-3454; Reisner and Martelli, Immunol Today (1999) 20:343-347; Handgretinger et al., Bone Marrow Transplant. (2001) 27:777-783].

The CD34 "megadose" transplants raised interesting questions as to how these cells overcome the barrier presented by host cytotoxic T-lymphocyte precursors (CTL-p). This question was answered, in part, by the finding that cells within the CD34 fraction are endowed with potent veto activity [Gur et al., Blood (2005) 105:2585-2593; Gur et al., Blood (2002) 99:4174-4181; Rachamim et al., Transplantation (1998) 65:1386-1393]. Other cell types have also been shown to mediate veto activity including T lymphocytes (e.g. CD8$^+$ CTLs), natural killer cells and dendritic cells. Direct comparison of the veto reactivity of various cell types revealed that CTLs comprise the strongest veto effect [Reich-Zeliger et al., J Immunol. (2004) 173:6654-6659].

One approach developed to generate veto CTLs without GVH reactivity was described by Reisner and co-workers, in which CTLs were stimulated against 3$^{rd}$-party stimulators in the absence of exogenous IL-2. This approach was based on the observation that only activated CTLp were capable of surviving the IL-2 deprivation in the primary culture. This method was shown in vitro and in vivo to deplete GVH reactivity from the anti-3$^{rd}$ party veto CTLs [PCT Publication No. WO 2001/049243, Bachar-Lustig et al., Blood. 2003; 102:1943-1950; Aviner et al., Hum Immunol. (2005) 66:644-652]. Introduction of these anti-3$^{rd}$ party veto CTLs into a recipient (along with a transplant) prevented graft rejection without inducing GVHD (PCT Publication No. WO 2001/049243).

Various approaches have been contemplated for graft transplantation without graft rejection and/or graft versus host disease, some are summarized infra.

PCT Publication No. WO 2007/023491 discloses the use of tolerogenic cells for reducing or preventing graft rejection of a non-syngeneic graft in a subject. The tolerogenic cells disclosed (e.g. CD4$^+$CD25$^+$ cells) may be derived from any donor who is non-syngeneic with both the subject and the graft ("third-party" tolerogenic cells). The graft (e.g. bone marrow) may be derived from any graft donor who is allogeneic or xenogeneic with the subject.

PCT Publication No. WO 2002/102971 discloses the use of cultured hematopoietic progenitor cells (HPC) comprising enhanced veto activity for inducing tolerance to a transplant transplanted from a donor to a recipient. The tolerogenic cells disclosed preferably express CD33 and are administered prior to, concomitantly with or following transplantation of the transplant (e.g. cell or organ transplant).

PCT Publication No. WO 2002/043651 discloses the use of a non-GVHD inducing population of immune effector cells for disease treatment. In order to arrive at the non-GVHD inducing population of immune effector cells, a first cell population (e.g. T-lymphocytes) are co-cultured with a second cell population being non-syngeneic with the subject and non-syngeneic with the first cell population (e.g.

EBV-infected B-lymphocytes) under conditions which include IL-2 starvation followed by IL-2 supplementation. The resultant immune effector cells may be used to treat diseases such as malignant diseases, viral diseases and autoimmune diseases.

U.S. Pat. No. 6,759,035 discloses methods of inhibiting graft rejection and inducing T cell tolerance in a solid organ transplant recipient. The methods disclosed comprise removing peripheral blood mononuclear cells (PBMC) from a donor and recipient, culturing the donor and recipient cells together in the presence of a compound that induces T cell suppressor activity (e.g. TGF-β, IL-15 and IL-2), and administering the recipient suppressor T cells to the recipient along with the transplant to prevent the recipient's T cells from killing donor cells, thereby inducing tolerance and long term survival of the transplant.

U.S. Pat. No. 6,803,036 discloses methods for treating donor cells to ameliorate graft versus host disease in a recipient patient. The methods disclosed comprise removing PBMCs from a donor and treating the cells with a suppressive composition (e.g. IL-10, IL-2, IL-4, IL-15 and TGF-β) for a time sufficient to induce T cell tolerance. The cells are then introduced to a recipient patient. The treated cells may be added to donor stem cells prior to introduction into the patient.

PCT Publication No. WO 2010/049935 disclosed an isolated population of cells comprising non-GVHD inducing anti-third party cells having a central memory T-lymphocyte (Tcm) phenotype, the cells being tolerance-inducing cells and capable of homing to the lymph nodes following transplantation.

SUMMARY OF THE INVENTION

According to an aspect of some embodiments of the present invention there is provided a method of generating an isolated population of cells comprising anti-third party cells having a central memory T-lymphocyte (Tcm) phenotype, the cells being tolerance-inducing cells and/or endowed with anti-disease activity, and capable of homing to the lymph nodes following transplantation, the method comprising: (a) contacting peripheral blood mononuclear cells (PBMC) with a third party antigen or antigens in the presence of IL-21 so as to allow enrichment of antigen reactive cells; and (b) culturing the cells resulting from step (a) in the presence of IL-21, IL-15 and IL-7 in an antigen free environment so as to allow proliferation of cells comprising the central memory T-lymphocyte (Tcm) phenotype, thereby generating the isolated population of cells.

According to an aspect of some embodiments of the present invention there is provided a method of generating an isolated population of cells comprising anti-third party cells having a central memory T-lymphocyte (Tcm) phenotype, the cells being tolerance-inducing cells and/or endowed with graft-versus-leukemia (GVL) activity, and capable of homing to the lymph nodes following transplantation, the method comprising: (a) treating non-adherent peripheral blood mononuclear cells (PBMC) with an agent capable of depleting CD4+ and/or CD56+ cells so as to obtain CD8+ T cells; (b) contacting the CD8+ T cells with third party dendritic cells in the presence of IL-21 for 12 hours to 5 days so as to allow enrichment of antigen reactive cells; (c) culturing the cells resulting from step (b) with the third party dendritic cells in the presence of IL-21, IL-15 and IL-7 for 12 hours to 3 days; and (d) culturing the cells resulting from step (c) in the presence of IL-21, IL-15 and IL-7 in an antigen free environment for 5-20 days so as to allow proliferation of cells comprising the central memory T-lymphocyte (Tcm) phenotype, thereby generating the isolated population of cells.

According to an aspect of some embodiments of the present invention there is provided a method of generating an isolated population of cells comprising anti-third party cells having a central memory T-lymphocyte (Tcm) phenotype, the cells being endowed with anti-disease activity, and capable of homing to the lymph nodes following transplantation, the method comprising: (a) treating non-adherent peripheral blood mononuclear cells (PBMC) with an agent capable of depleting CD4+ and/or CD56+ cells so as to obtain CD8+ T cells; (b) contacting the CD8+ T cells with non-syngeneic dendritic cells in the presence of IL-21 for 12 hours to 5 days so as to allow enrichment of antigen reactive cells; (c) culturing the cells resulting from step (b) with the non-syngeneic dendritic cells in the presence of IL-21, IL-15 and IL-7 for 12 hours to 3 days; and (d) culturing the cells resulting from step (c) in the presence of IL-21, IL-15 and IL-7 in an antigen free environment for 5-20 days so as to allow proliferation of cells comprising the central memory T-lymphocyte (Tcm) phenotype, thereby generating the isolated population of cells.

According to an aspect of some embodiments of the present invention there is provided an isolated population of cells comprising anti-third party cells having a central memory T-lymphocyte (Tcm) phenotype, wherein at least 50% of the isolated population of cells are CD3+CD8+ cells of which at least 50% comprise a $CD3^+$, $CD8^+$, $CD62L^+$, $CD45RA^-$, $CD45RO^+$ signature, and further wherein the cells are tolerance-inducing cells and/or endowed with anti-disease activity, and capable of homing to the lymph nodes following transplantation.

According to an aspect of some embodiments of the present invention there is provided an isolated population of cells comprising anti-third party cells having a central memory T-lymphocyte (Tcm) phenotype, the cells being tolerance-inducing cells and/or endowed with anti-disease activity, and capable of homing to the lymph nodes following transplantation, generated according to the present methods.

According to an aspect of some embodiments of the present invention there is provided a method of treating a disease in a subject in need thereof, wherein the disease is selected from the group consisting of a malignant disease, a viral disease and an autoimmune disease, the method comprising administering to the subject a therapeutically effective amount of the isolated population of cells of the present invention, thereby treating the subject.

According to an aspect of some embodiments of the present invention there is provided a method of treating a subject in need of a cell or tissue transplantation, the method comprising: (a) transplanting a cell or tissue transplant into the subject; and (b) administering to the subject a therapeutically effective amount of the isolated population of cells of the present invention, thereby treating the subject.

According to an aspect of some embodiments of the present invention there is provided a method of treating a subject in need of an immature hematopoietic cell transplantation, the method comprising: (a) transplanting immature hematopoietic cells into the subject; and (b) administering to the subject a therapeutically effective amount of the isolated population of cells of the present invention, thereby treating the subject.

According to some embodiments of the invention, the method further comprises depleting non-adherent cells from the PBMC prior to step (a).

According to some embodiments of the invention, the method further comprises depleting CD4+ and/or CD56+ cells from the PBMC prior to step (a).

According to some embodiments of the invention, the method further comprises selecting CD45RA+ and/or CD45RO− cells from the PBMC prior to step (a).

According to some embodiments of the invention, the PBMC comprise CD8+ T cells.

According to some embodiments of the invention, the method further comprises culturing the cells resulting from step (a) with a third party antigen or antigens in the presence of IL-21, IL-15 and IL-7 following step (a) and prior to step (b).

According to some embodiments of the invention, the third party antigen or antigens comprise dendritic cells.

According to some embodiments of the invention, the dendritic cells are irradiated dendritic cells.

According to some embodiments of the invention, the third party antigen or antigens is selected from the group consisting of third party cells, a cell antigen, a viral antigen, a bacterial antigen, a protein extract, a purified protein and a synthetic peptide presented by autologous presenting cells, non-autologous presenting cells or on an artificial vehicle or on artificial antigen presenting cells.

According to some embodiments of the invention, the third party cells are stimulatory cells selected from the group consisting of cells purified from peripheral blood lymphocytes, spleen or lymph nodes, cytokine-mobilized PBLs, in vitro expanded antigen-presenting cells (APC), in vitro expanded dendritic cells and artificial antigen presenting cells.

According to some embodiments of the invention, the method further comprises selecting CD45RA+ and/or CD45RO− cells from the PBMC following step (a) and prior to step (b).

According to some embodiments of the invention, the CD8+ T cells comprise naïve CD8+ T cells.

According to some embodiments of the invention, the dendritic cells comprise in vitro expanded dendritic cells.

According to some embodiments of the invention, the dendritic cells comprise irradiated dendritic cells.

According to some embodiments of the invention, the contacting in the presence of IL-21 is effected for 12 hours to 5 days.

According to some embodiments of the invention, the contacting in the presence of IL-21 is effected for 2-3 days.

According to some embodiments of the invention, the contacting in the presence of IL-21 is effected for 3 days.

According to some embodiments of the invention, the method further comprises selecting for activated cells following step (a) and prior to step (b).

According to some embodiments of the invention, the method further comprises selecting for activated cells following step (b) and prior to step (c).

According to some embodiments of the invention, the selecting for activated cells is effected by selection of CD137+ and/or CD25+ cells.

According to some embodiments of the invention, the selecting for activated cells is effected 12-72 hours after the contacting.

According to some embodiments of the invention, the culturing with the third party antigen or antigens in the presence of IL-21, IL-15 and IL-7 is effected for 12 hours to 3 days.

According to some embodiments of the invention, the presence of IL-21, IL-15 and IL-7 in the antigen free environment is effected for 5-20 days.

According to some embodiments of the invention, the culturing in the presence of IL-21, IL-15 and IL-7 in the antigen free environment is effected for 7-11 days.

According to some embodiments of the invention, the method further comprises depleting alloreactive cells following step (b).

According to some embodiments of the invention, the method further comprises depleting alloreactive cells following step (d).

According to some embodiments of the invention, the depleting the alloreactive cells is effected by depletion of CD137+ and/or CD25+ cells following contacting the cells comprising the central memory T-lymphocyte (Tcm) with host antigen presenting cells (APCs).

According to some embodiments of the invention, the peripheral blood mononuclear cells (PBMC) are syngeneic with respect to a subject.

According to some embodiments of the invention, the peripheral blood mononuclear cells (PBMC) are non-syngeneic with respect to a subject.

According to some embodiments of the invention, the non-syngeneic PBMC are xenogeneic or allogeneic with respect to a subject.

According to some embodiments of the invention, the anti-third party cells having a T central memory phenotype comprises a $CD3^+$, $CD8^+$, $CD62L^+$, $CD45RA^-$, $CD45RO^+$ signature.

According to some embodiments of the invention, at least 50% of the isolated population of cells are CD3+CD8+ cells of which at least 50% have the signature.

According to some embodiments of the invention, the malignant disease comprises a leukemia or a lymphoma.

According to some embodiments of the invention, the isolated population of cells are syngeneic with the subject.

According to some embodiments of the invention, the isolated population of cells are non-syngeneic with the subject.

According to some embodiments of the invention, the method further comprises conditioning the subject under sublethal, lethal or supralethal conditions prior to the transplanting.

According to some embodiments of the invention, the cell or tissue transplant is syngeneic with the subject.

According to some embodiments of the invention, the cell or tissue transplant is derived from a donor selected from the group consisting of an HLA identical allogeneic donor, an HLA non-identical allogeneic donor and a xenogeneic donor.

According to some embodiments of the invention, the cell or tissue transplant comprises immature hematopoietic cells.

According to some embodiments of the invention, the cell or tissue transplant is selected from the group consisting of a liver, a pancreas, a spleen, a kidney, a heart, a lung, a skin, an intestine and a lymphoid/hematopoietic tissue or organ.

According to some embodiments of the invention, the cell or tissue transplant comprises a co-transplantation of several organs.

According to some embodiments of the invention, the co-transplantation comprises transplantation of immature hematopoietic cells and a solid organ.

According to some embodiments of the invention, the immature hematopoietic cells and the solid organ or obtained from the same donor.

According to some embodiments of the invention, immature hematopoietic cells are transplanted prior to, concomitantly with, or following the transplantation of the solid organ.

According to some embodiments of the invention, the isolated population of cells are administered prior to, concomitantly with, or following the cell or tissue transplant.

According to some embodiments of the invention, the isolated population of cells are syngeneic with the subject.

According to some embodiments of the invention, the isolated population of cells are non-syngeneic with the subject.

According to some embodiments of the invention, the cell or tissue transplant and the isolated population of cells are derived from the same donor.

According to some embodiments of the invention, the cell or tissue transplant is syngeneic with the subject and the isolated population of cells are non-syngeneic with the subject.

According to some embodiments of the invention, the cell or tissue transplant is syngeneic with the subject and the isolated population of cells are syngeneic with the subject.

According to some embodiments of the invention, the isolated population of cells are administered prior to, concomitantly with, or following the immature hematopoietic cells.

According to some embodiments of the invention, the immature hematopoietic cells and the isolated population of cells are derived from the same donor.

According to some embodiments of the invention, the donor is non-syngeneic with the subject.

According to some embodiments of the invention, the immature hematopoietic cells and the isolated population of cells are derived from the subject.

According to some embodiments of the invention, the method further comprises conditioning the subject under sublethal, lethal or supralethal conditions prior to the transplanting.

According to some embodiments of the invention, the subject is a human subject.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 1A-1B are schematic diagrams depicting human autologous (FIG. 1A) and allogeneic (FIG. 1B) settings. Of note, the two settings differ from each other in the origin of the bone marrow (BM) donor (host vs. allogeneic), the responders (host vs. allogeneic) and stimulators (any allogeneic donor vs. $3^{rd}$ party not cross-reactive with host MHC) that are involved in the Tcm generation.

FIGS. 2A-2B are schematic diagrams depicting mouse syngeneic (FIG. 2A) and allogeneic (FIG. 2B) settings. Of note, the two settings differ from each other in the origin of the BM donor (syngeneic or F1 vs. allogeneic), the responders (syngeneic or F1 vs. allogeneic) and stimulators (allogeneic vs. $3^{rd}$ party) that are involved in the Tcm generation.

FIGS. 3A-3B are schematic diagrams depicting the autologous human protocol for generation of Tcm (FIG. 3A) in comparison to the syngeneic mouse protocol (FIG. 3B).

FIGS. 4A-4C depict the kinetics of anti-$3^{rd}$ party central memory generation ("reference control experiments"). Naïve CD8 T cells were stimulated with irradiated allogeneic 3rd party DC at a ratio of 4:1 in a medium containing IL-21 for 3 days. Thereafter, the cells received no further activation and were expanded in medium containing IL-7 and IL-15 until day 12.5. On days 7.5, 10.5 and 12.5, cells were evaluated for phenotype (surface marker expression) (FIG. 4A), and percentage of Tcm (CD62L+CD45RO+) from CD8 T cells using FACS analysis (FIG. 4B), and for cell numbers by trypan blue exclusion (FIG. 4C). For each time point data represent average ±SE of n independent experiments.

Figure 5A:
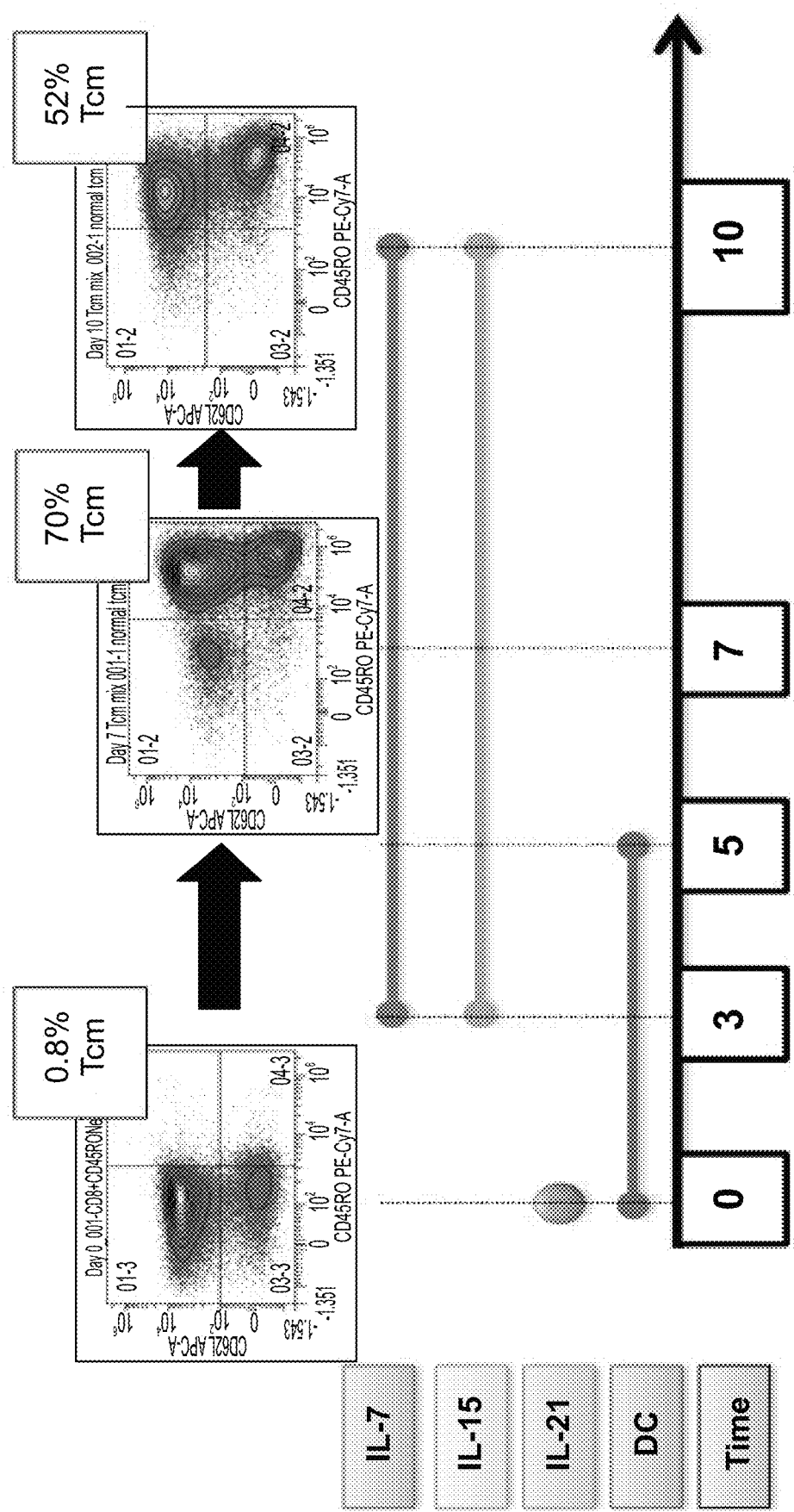
Figure 5B:
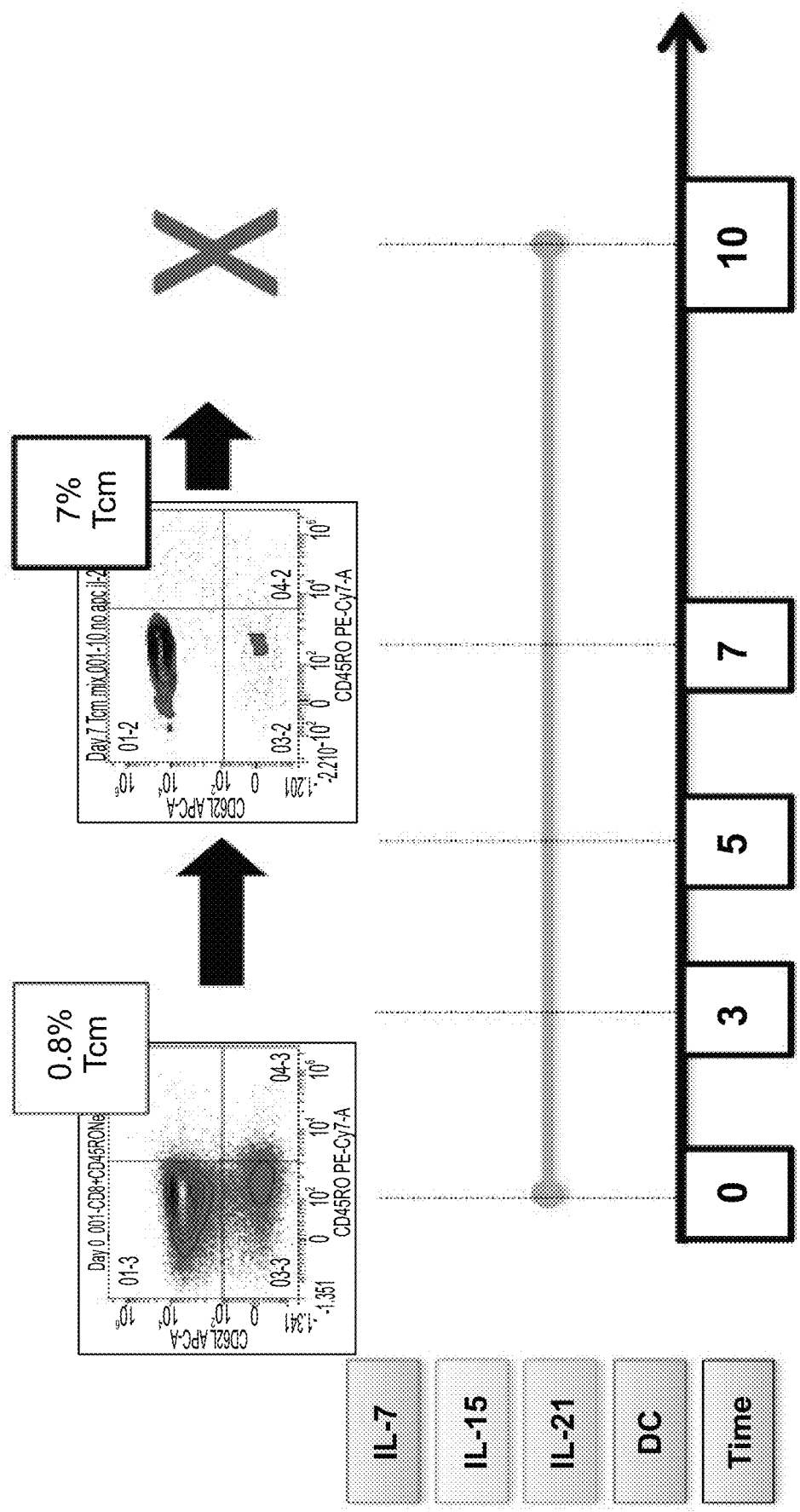

FIGS. 5A-5C depict a typical experiment demonstrating the role of priming with allogeneic DC. Of note, IL-21 alone or IL-7 plus IL-15 without DC priming does not induce central memory phenotype in naïve CD8 T cells and poorly supports their expansion. FIG. 5A illustrates naïve CD8 T cells which were stimulated with irradiated allogeneic 3rd party DC at a ratio of 4:1 in a medium containing IL-21 for 3 days. Thereafter, the cells received no further activation and were expanded with IL-7 and IL-15 until day 13 ("reference control group"=d(0-3) IL21+DC d(3-13)IL7+IL15); FIGS. 5B-5C illustrate naïve CD8 T cells which were cultured with IL-21 (FIG. 5B) or with a combination of IL-7 and IL-15 (FIG. 5C) in the absence of stimulation until day 10 or day 13, respectively.

FIGS. 6A-6B depict the role of priming with allogeneic DC demonstrated by the average relative impact on Tcm level and fold expansion compared to the reference control group. Naïve CD8 T cells were stimulated with irradiated allogeneic 3rd party DC at a ratio of 4:1 in a medium containing IL-21 for 3 days. Thereafter, the cells received no further activation and were expanded with IL-7 and IL-15 until day 13 ("Reference control group"=d(0-3) IL21+DC d(3-13)IL7+IL15). Alternatively, naïve CD8 T cells were cultured with IL-21 or with combination of IL-7 and IL-15 in the absence of stimulation until day 13. Cells were evaluated for cell numbers by trypan blue exclusion (FIG. 6A), and percentage of Tcm (CD62L+CD45RO+) from CD8 T cells using FACS analysis (FIG. 6B). For each time point, data represent the average ±SE of n independent experiments.

Figure 7A:
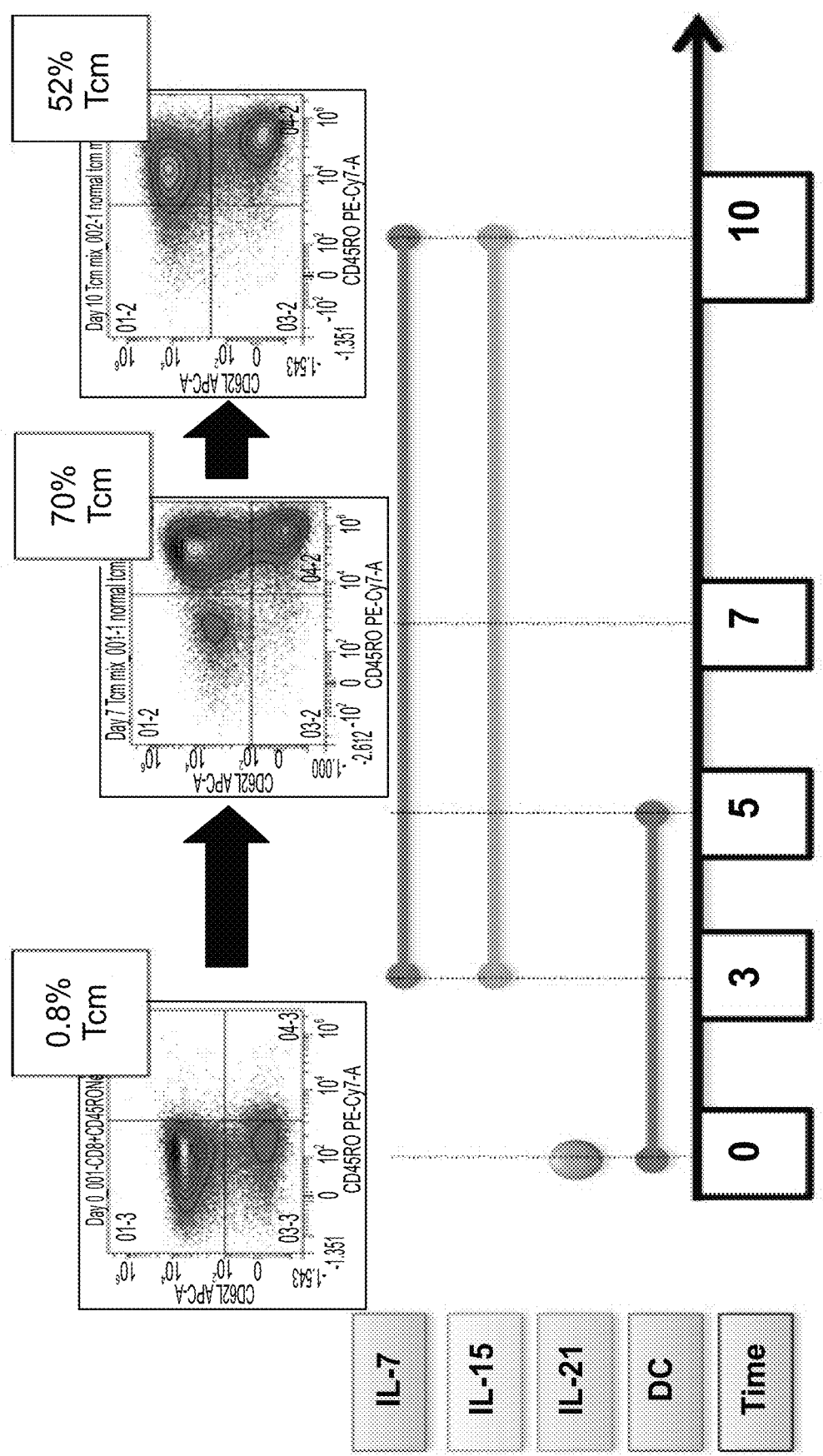
Figure 7B:
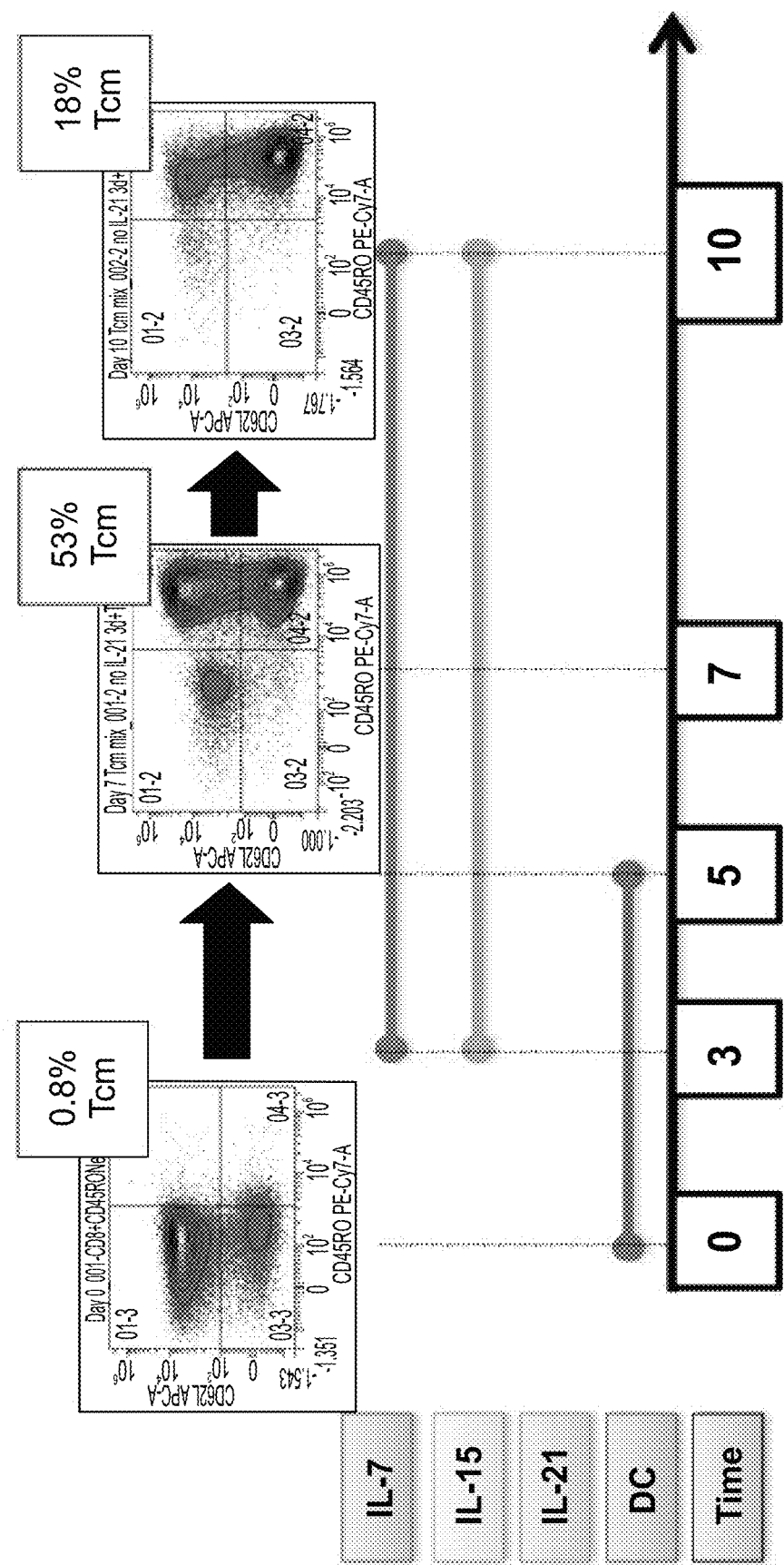
Figure 7C:
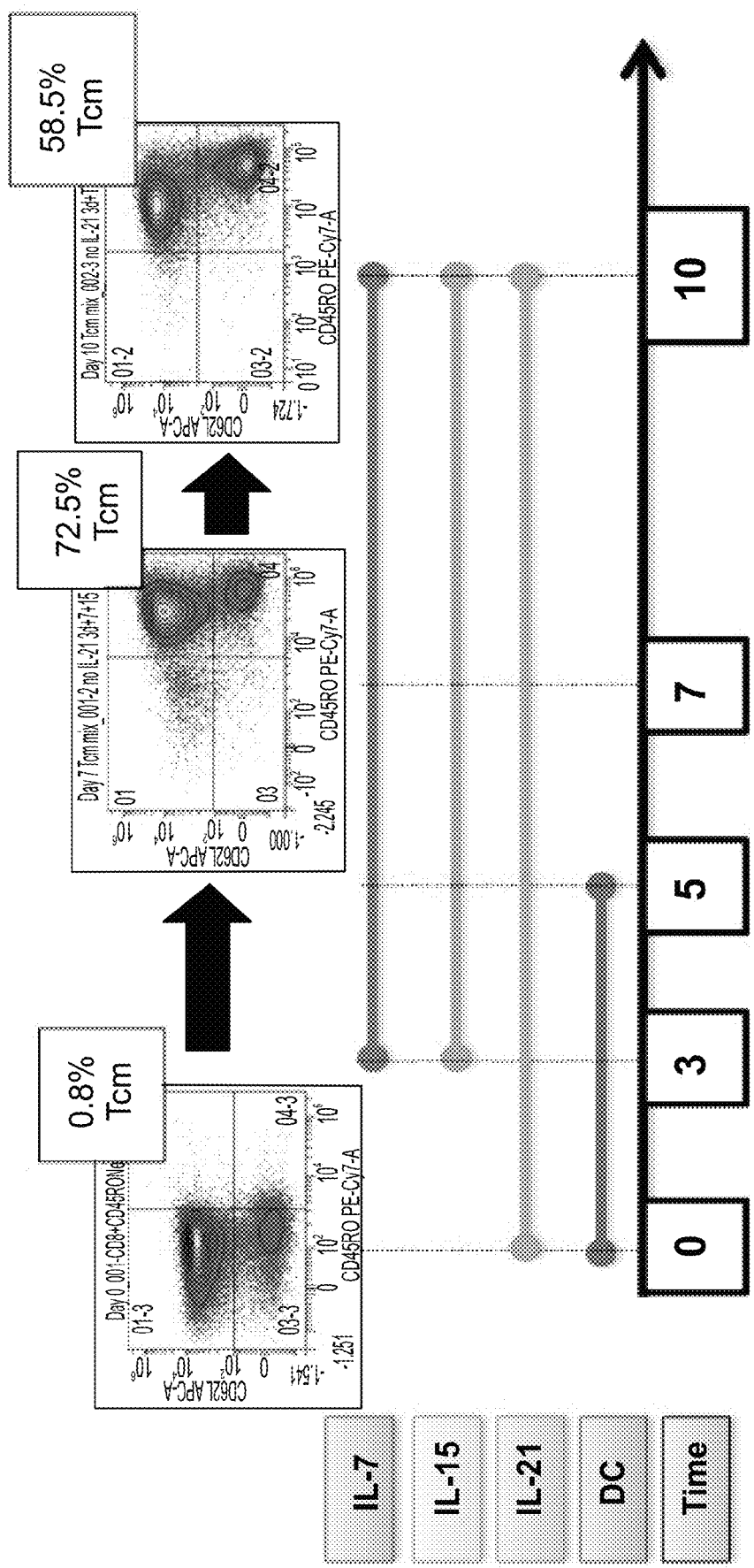

FIGS. 7A-7C depict a typical experiment demonstrating the role of IL-21 in the priming and expansion phases of anti-3rd party Tcm. Of note, removal of IL-21 from the priming phase reduced both expansion and Tcm induction, while the presence of IL-21 throughout the culture increased Tcm induction. FIG. 7A illustrates naïve CD8 T cells which were stimulated with irradiated allogeneic 3rd party DC at a ratio of 4:1 in a medium containing IL-21 for 3 days. Thereafter, the cells received no further activation and were expanded with IL-7 and IL-15 until day 13 ("reference control group"=d(0-3) IL21+DC d(3-13)IL7+IL15); FIGS.

7B-7C illustrate naïve CD8 T cells which were stimulated with irradiated allogeneic 3rd party DC at a ratio of 4:1 in the absence of IL-21 for 3 days. Thereafter the cells received no further activation and were expanded with IL-7 and IL-15 until day 13 (FIG. 7B), or stimulated with irradiated allogeneic 3rd party DC at a ratio of 4:1 with continuous presence of IL-21 in both the priming phase (IL-21 alone) and in the expansion phase (together with IL-7 and IL-15) (FIG. 7C).

FIGS. 8A-8B depict the requirement for IL-21 for optimal Tcm yield (average of several independent experiments). Naïve CD8 T cells were treated as above and cultures were evaluated for cell number by trypan blue exclusion (FIG. 8A), and percentage of Tcm (CD62L+CD45RO+) from CD8 T cells using FACS analysis (FIG. 8B). Results of each experiment are shown separately and lines indicate average results over n experiments.

FIGS. 9A-9B depict the optimal responder/DC ratio for the induction of Tcm phenotype and robust expansion. $4 \times 10^5$ naïve CD8 T cells were stimulated against irradiated allogeneic 3rd party DC at increasing numbers in the presence of IL-21 for 3 days. Thereafter the cells received no further activation and were expanded with IL-7 and IL-15 until day 13 ("reference control group"=d(0-3) IL21+100,00 DC d(3-13) IL7+IL15). Cultures were evaluated for cell numbers by trypan blue exclusion (FIG. 9A), and percentage of Tcm (CD62L+CD45RO+) from CD8 T cells using FACS analysis (FIG. 9B). Results of each experiment are shown separately and Lines indicate average results over n experiments.

FIG. 10 depicts an evaluation of the effect of different GMP grade reagents on the enrichment of CD8+ and naïve CD8+CD45RA+ T cells. Donor PBMC were depleted from adherent cells by overnight incubation in plates specifically designed to remove adherent myeloid cells (upper panel), and on day 0, non adherent cells were divided to four test groups, each subjected to a different magnetic sorting protocols. Cells were evaluated for cell composition and Tcm phenotype by FACS analysis. The results in the left column (CD45RO and CD45RA) are gated on CD3+CD8+ cells. The results represent a typical experiment out of two independent experiments performed.

Figure 11:
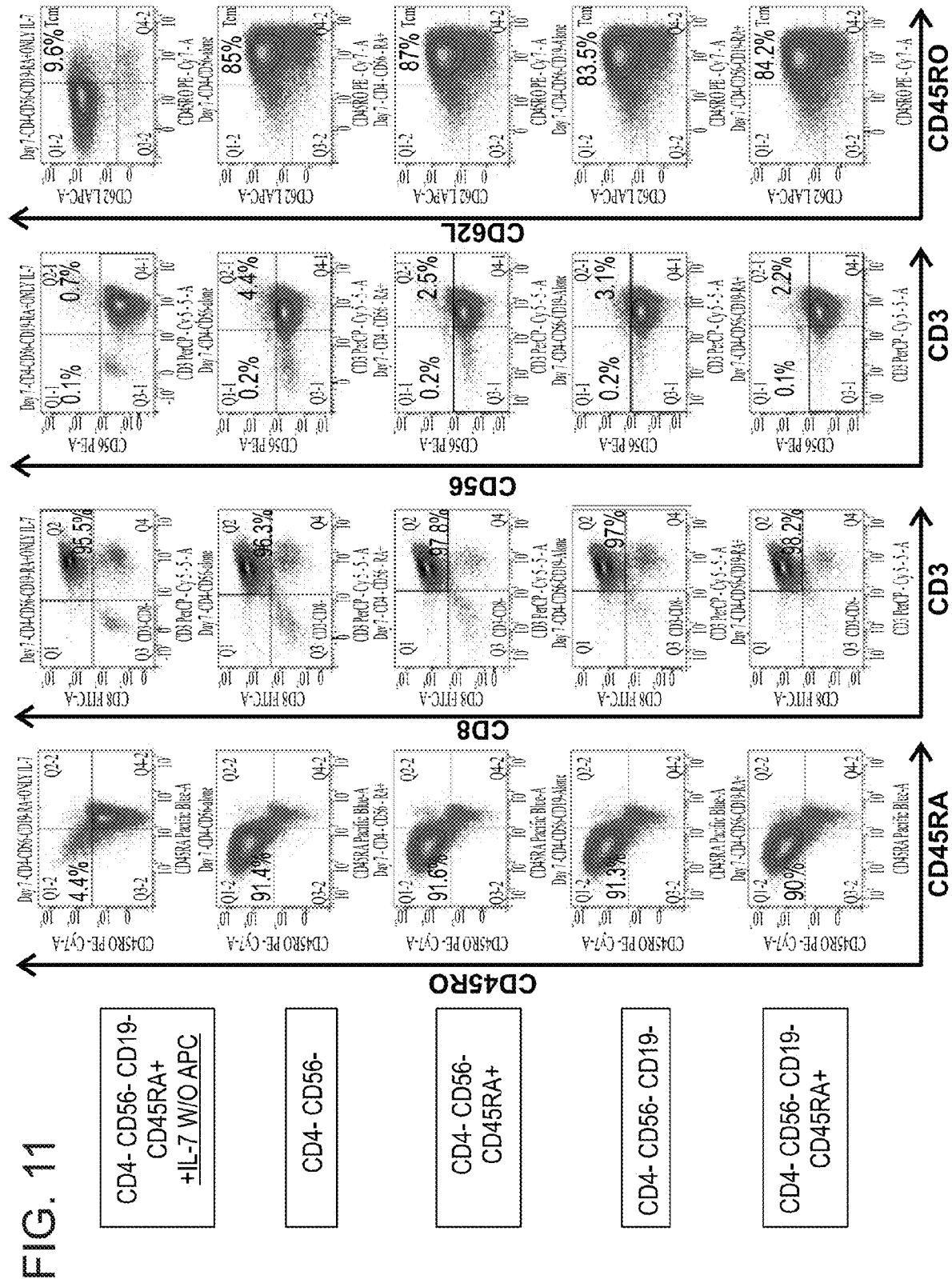

FIG. 11 depicts a typical experiment showing the effect of different GMP grade reagents used for isolation of CD8 T cells, on the proportion of CD8+ T cells with a Tcm phenotype, and contamination with NK and NKT cells, 7 days after stimulation with 3rd party DCs. Unstimulated cells maintained in culture with IL-7 alone (upper panel) were used as a reference. The results in the left most column (CD45RO and CD45RA) and right most column (CD62L and CD45RO) are gated on CD3+CD8+ cells.

Figure 12:
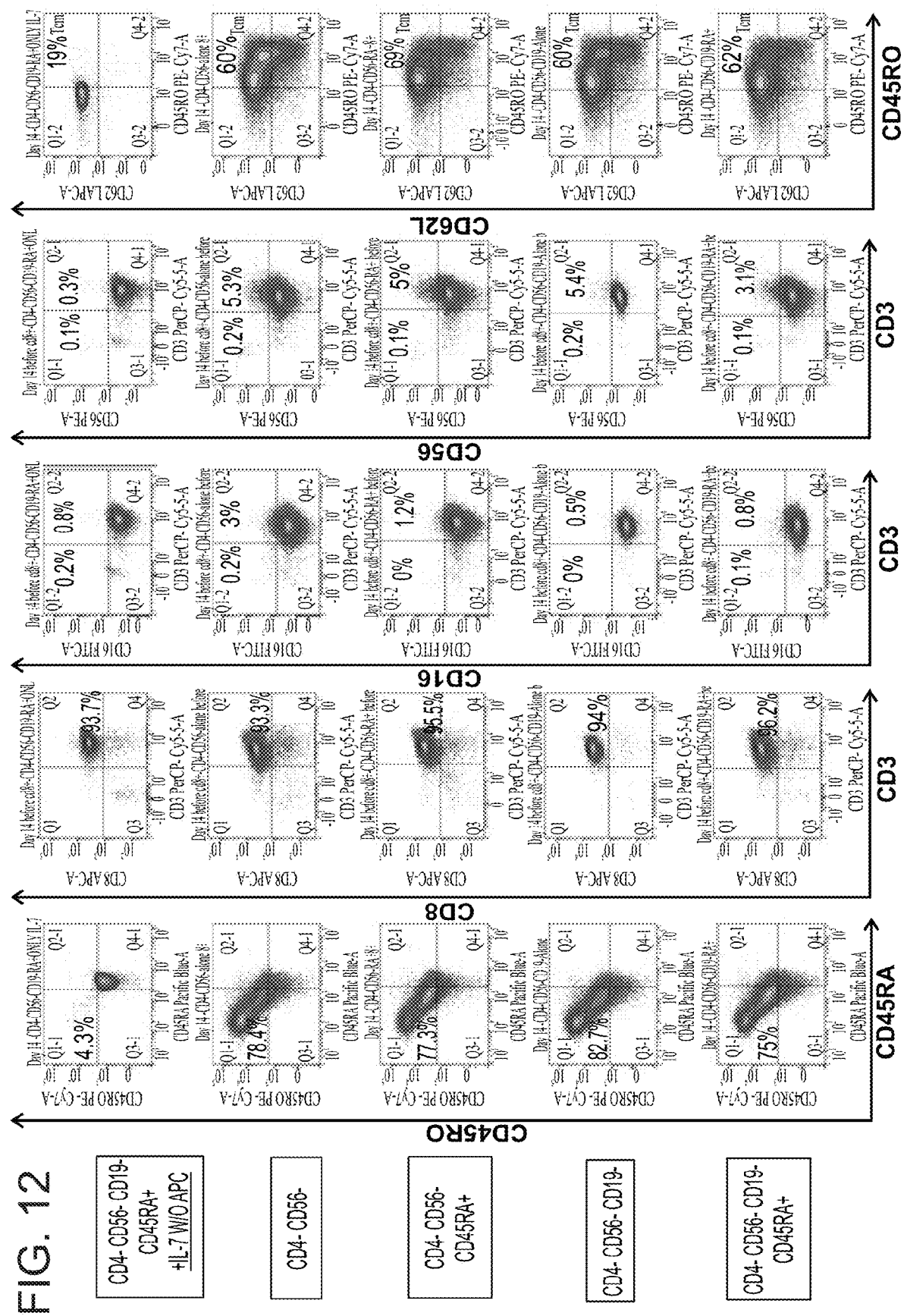

FIG. 12 depicts a typical experiment showing the effect of different GMP grade reagents used for isolation of CD8 T cells, on the proportion of CD8+ T cells with a Tcm phenotype, and contamination with NK and NKT cells, 14 days after stimulation with $3^{rd}$ party DCs. Unstimulated cells maintained in culture with IL-7 alone (upper panel) were used as a reference. The results in the left most column (CD45RO and CD45RA) and right most column (CD62L and CD45RO) are gated on CD3+CD8+ cells.

Figure 13A:
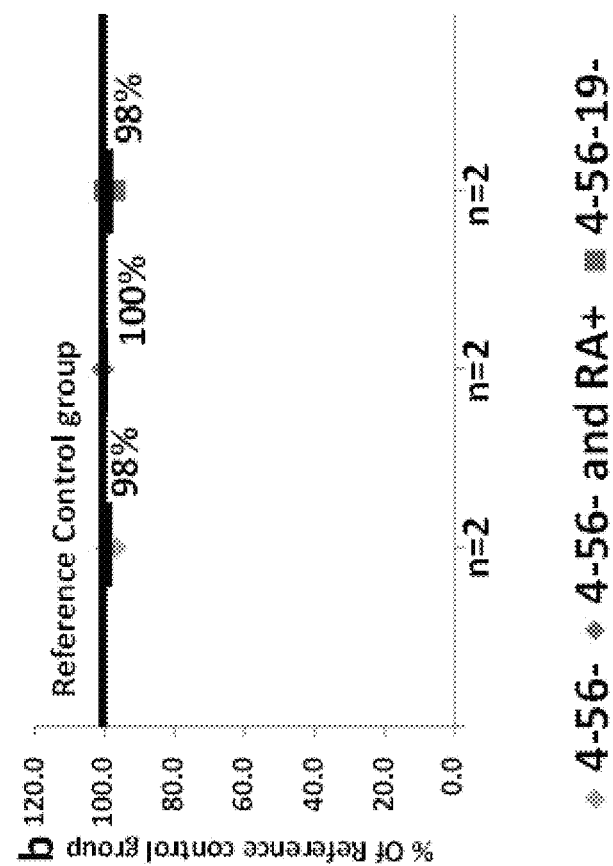
Figure 13B:
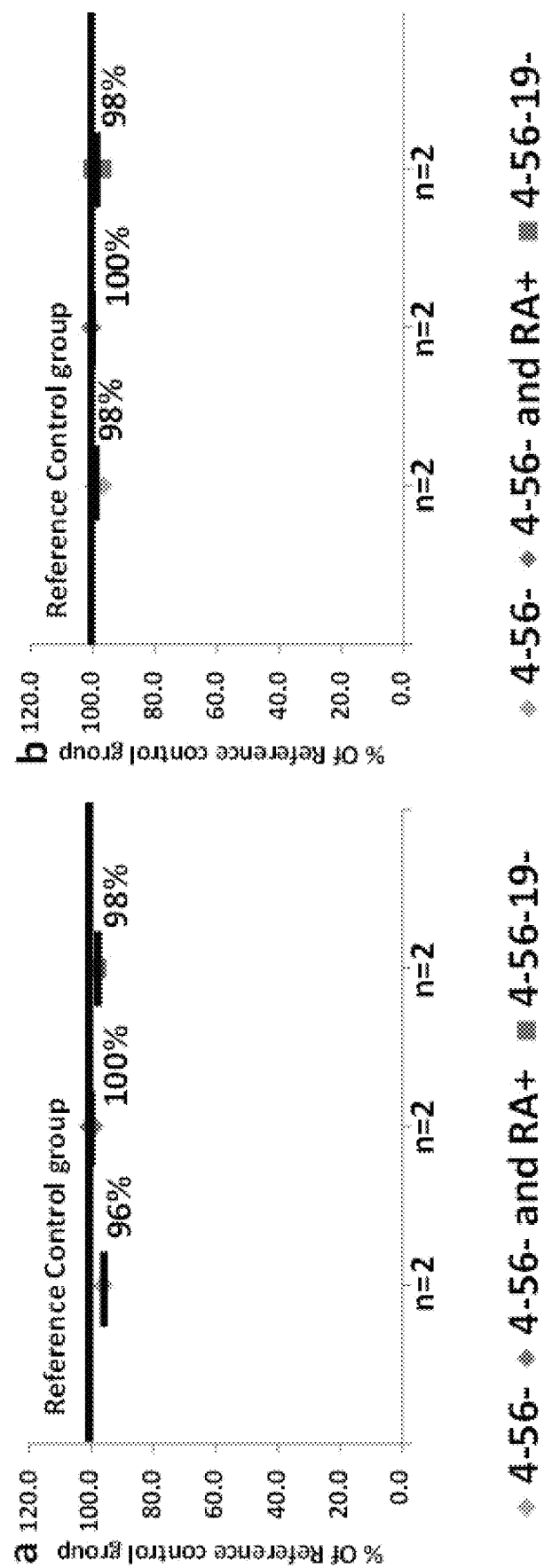

FIGS. 13A-13B depict the effect of different GMP grade reagents used for isolation of CD8 T cells on the levels of CD8 T cells with a Tcm phenotype after 7 days of stimulation against 3rd party DCs. Average percent of CD3+ CD8+ NKT− T cells (FIG. 13A) and Tcm (FIG. 13B) are shown as percent of the levels attained in the optimal control group making use of all 4 reagents (CD4/CD56/CD19/CD45RA).

Figure 14A:
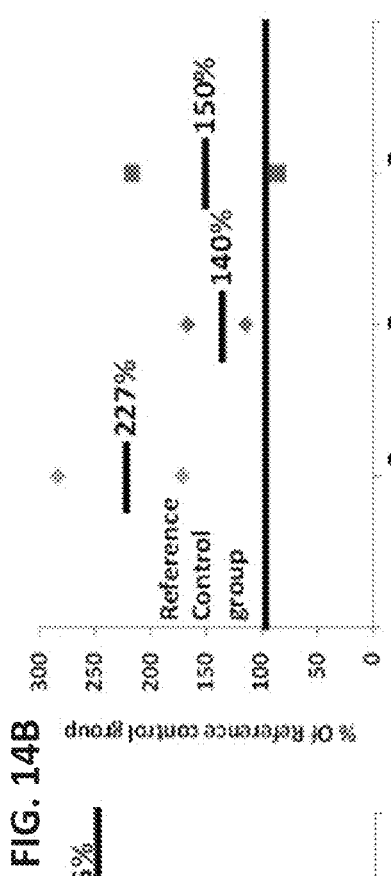
Figure 14B:
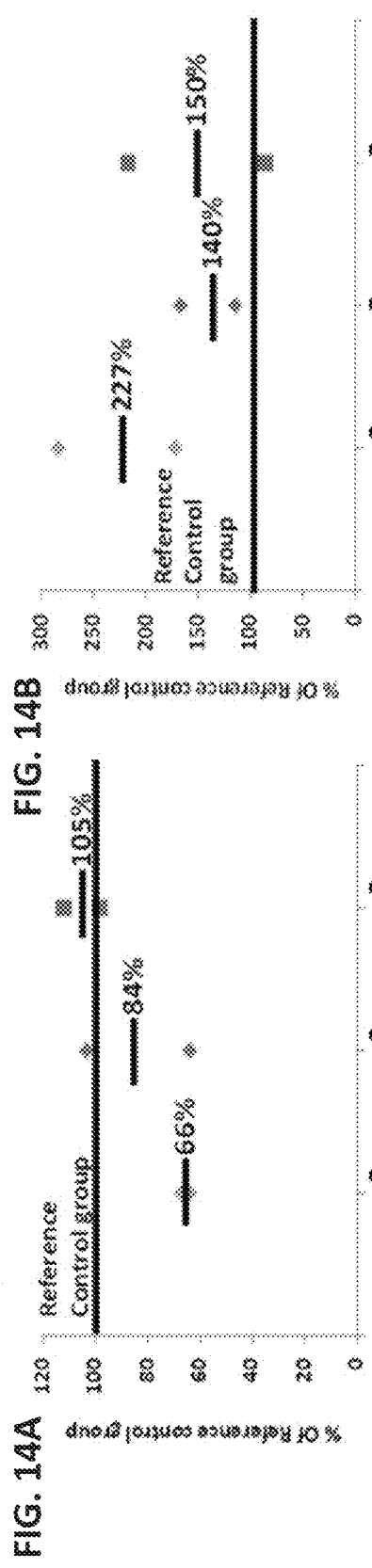
Figure 14C:
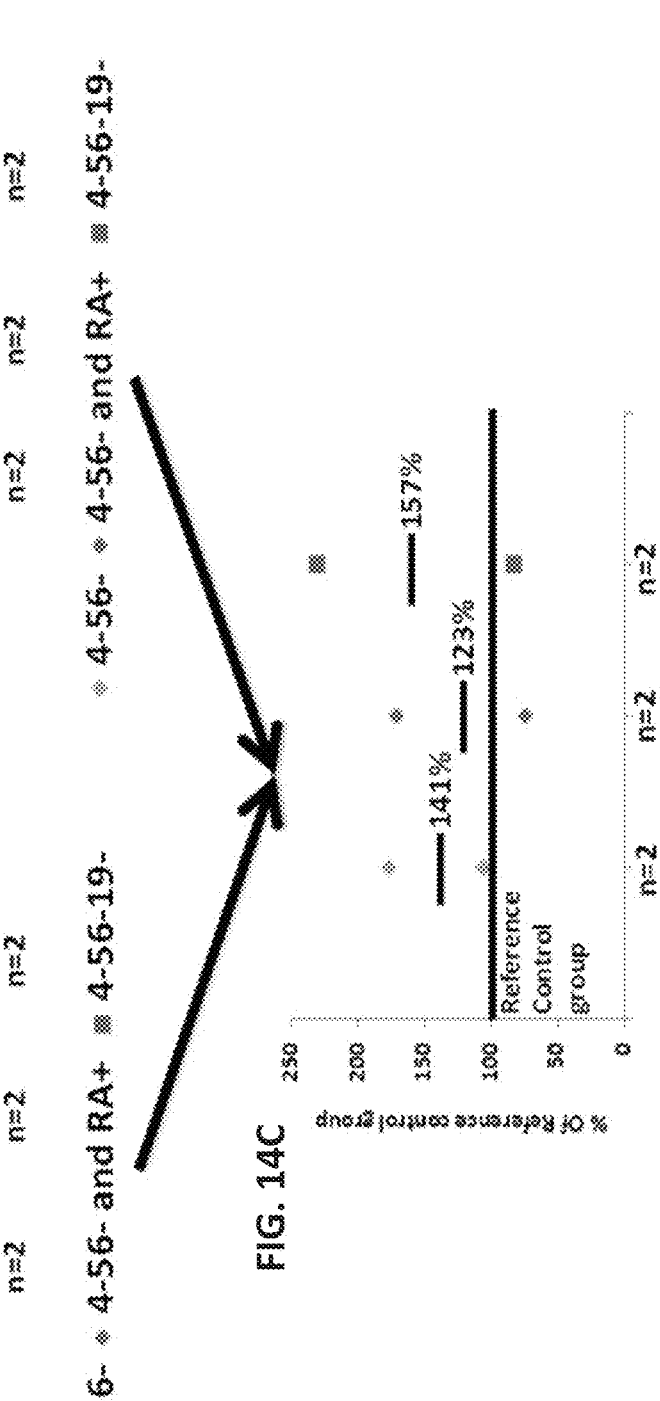

FIGS. 14A-14C depict the effect of different GMP grade reagents used for isolation of CD8 T cells on the final yield of CD8 T cells with a Tcm phenotype after 10 days of stimulation against 3rd party DCs. Average fold expansion from day 0 at day 10 (FIG. 14A), and average yield after magnetic sorting (FIG. 14B) are shown as percent of the levels attained in the optimal control group making use of all four selection reagents (CD4/CD56/CD19/CD45RA). The yield of Tcm at day 10 (FIG. 14C) was calculated by multiplication of the yield after magnetic sorting (at day 0) with the fold expansion from day 0 (at day 10).

Figure 15:
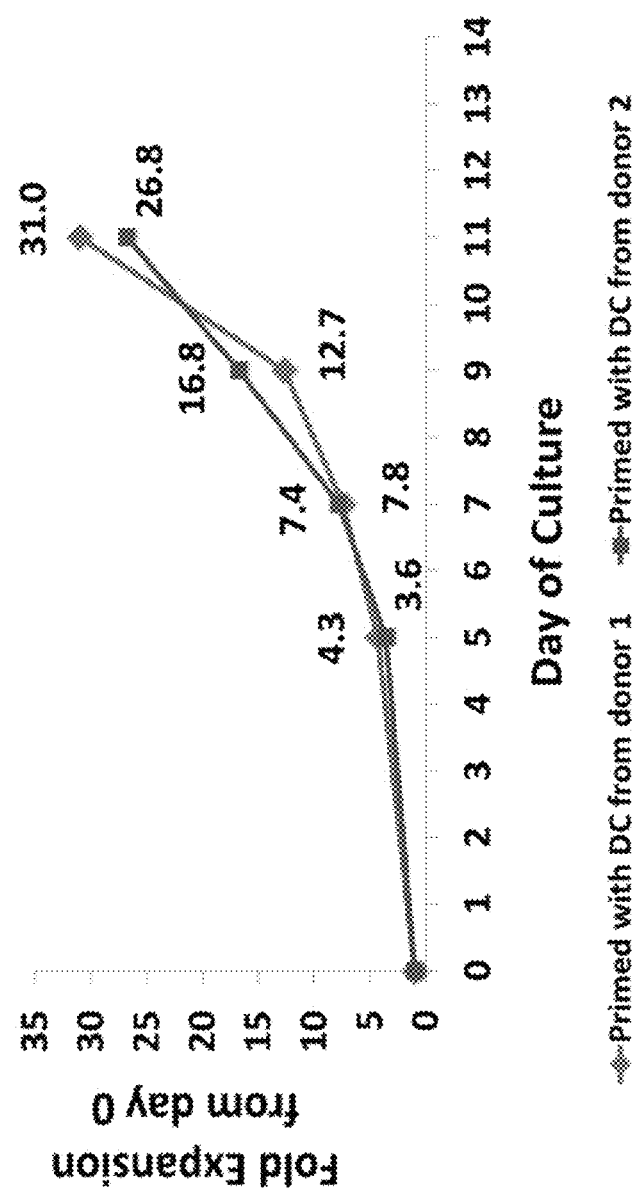

FIG. 15 depicts that changing the source for allogeneic DC stimulators had only minor effect on the expansion potential of the Tcm cells. CD8 T cells were enriched from thawed leukapheresis by depletion of CD4+ and CD56+ cells using the CliniMacs system. The enriched CD8 T cells were then divided into two test groups, each stimulated with different irradiated allogeneic 3rd party DC, at a ratio of 6:1 in a medium containing IL-21 for 3 days in culture bags. Thereafter, the cells received no further activation and were expanded in medium containing IL-7, IL-15 and IL-21 until day 11. On days 5, 7, 9 and 11 of culture cell numbers was determined by trypan blue exclusion.

Figure 16A:
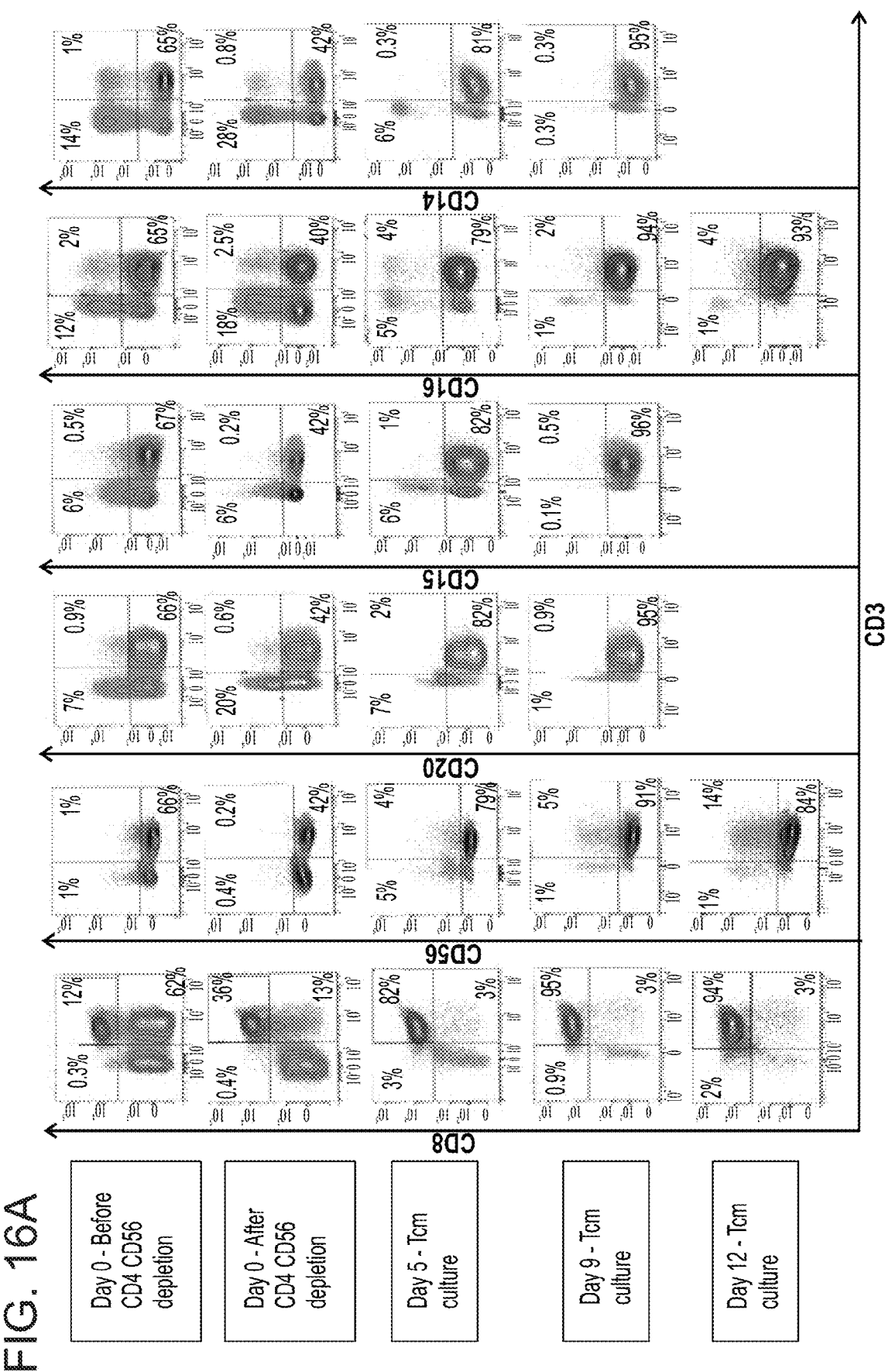
Figure 16B:
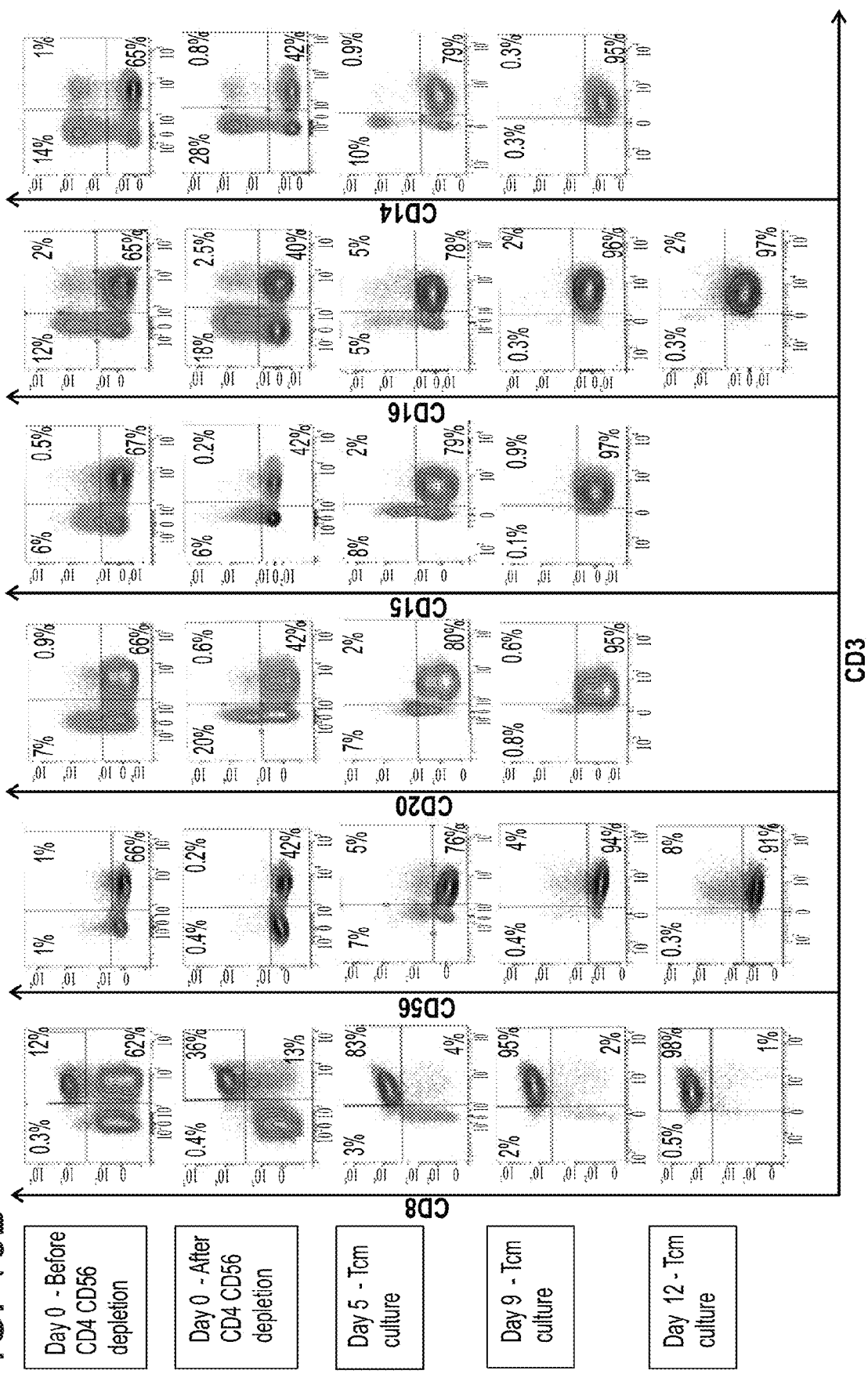

FIGS. 16A-16B depict that changing the source for allogeneic DC stimulators had only minor effect on the cell composition. CD8 T cells were enriched from thawed leukapheresis by depletion of CD4+ and CD56+ cells using the CliniMacs system for large scale isolation. The enriched CD8 T cells were then divided into two test groups, each stimulated with different irradiated allogeneic 3rd party DC (FIGS. 16A and 16B, respectively), at a ratio of 6:1 in a medium containing IL-21 for 3 days in culture bags. Thereafter, the cells received no further activation and were expanded in medium containing IL-7, IL-15 and IL-21 until day 11. On days 0, 5, 9 and 12 of culture cells were evaluated for cell composition by FACS analysis. All the results are gated from lymphogate and live gate (7AAD−).

FIGS. 17A-17B depict that changing the source for allogeneic DC stimulators had only minor effect on the cell composition. CD8 T cells were enriched from thawed leukapheresis by depletion of CD4+ and CD56+ Cells using the CliniMacs system. The enriched CD8 T cells were then divided into two test groups, each stimulated with different irradiated allogeneic 3rd party DC, at a ratio of 6:1 in a medium containing IL-21 for 3 days in culture bags. Thereafter, the cells received no further activation and were expanded in medium containing IL-7, IL-15 and IL-21 until day 11. On days 0, 5, 9 and 12 of culture cells were evaluated for Tcm phenotype (CD45RO+CD62L+) composition by FACS analysis. All the results are gated from lymphogate and live gate (7AAD−) and CD8 T cell (CD3+CD8+CD56− CD16−).

Figure 17C:
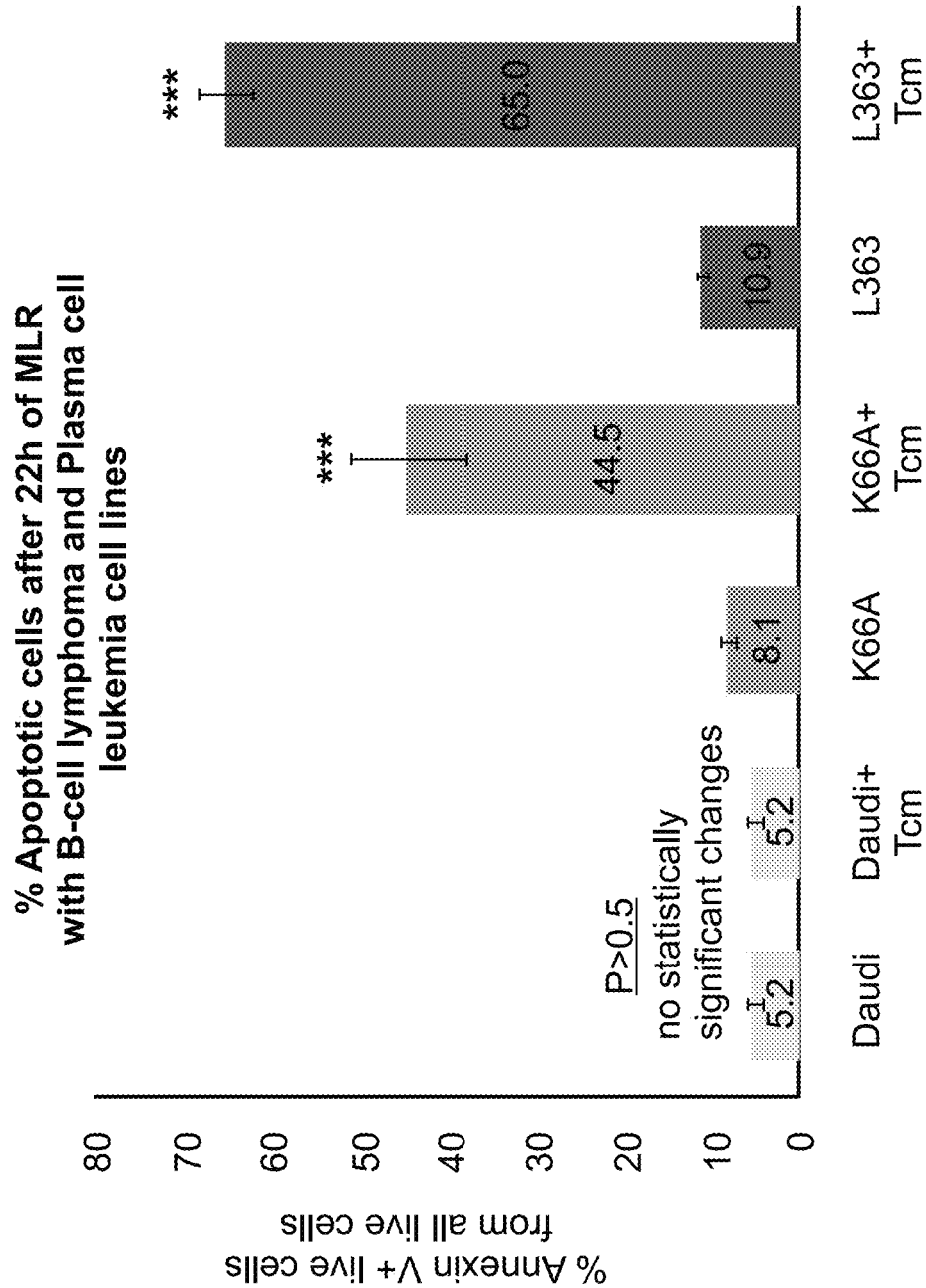

FIG. 17C depicts the percent apoptotic cells after 22 hours of mixed lymphocyte reaction (MLR) with B-cell lymphoma and plasma cell leukemia cell lines. CalceinAM pre-labeled Daudi, H.My2 C1R HLA A2 K66A mutant or L363 cell lines were incubated for 22 hours with or without 5-fold excess of anti-$3^{rd}$ party Tcm. Annexin V+ cells were determined by FACS. Data is shown as mean±SD of pentaplicate cultures.***p<0.001 values indicate statistically significant changes compared to samples cultured in the absence of Tcm.

Figure 18:
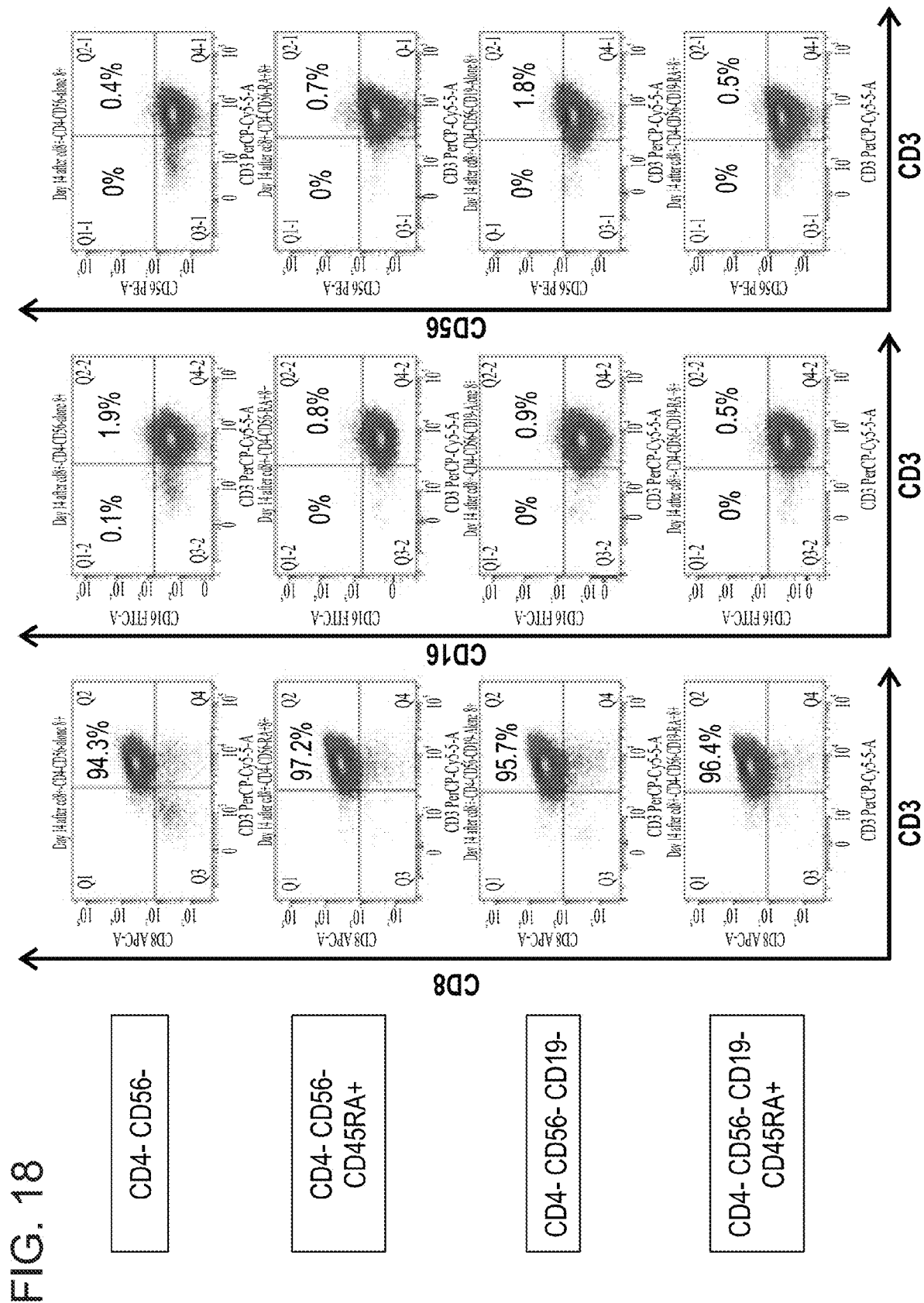

FIG. 18 depicts a typical experiment showing enrichment for CD8 T cells, at day 14 before graft versus leukemia (GVL) assay, by extensively depleting non CD8 T cells (i.e., CD4+ T cells, γ/δ T cells, B cells, NK cells, dendritic cells, monocytes, granulocytes, and erythroid cells) using magnetic bead sorting.

Figure 19A:
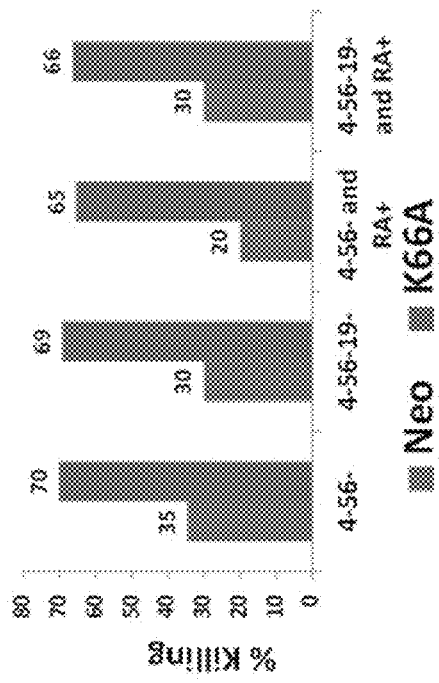
Figure 19B:
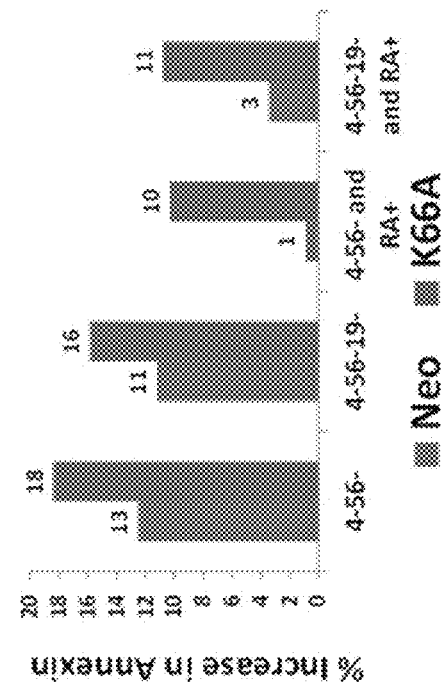
Figure 19C:
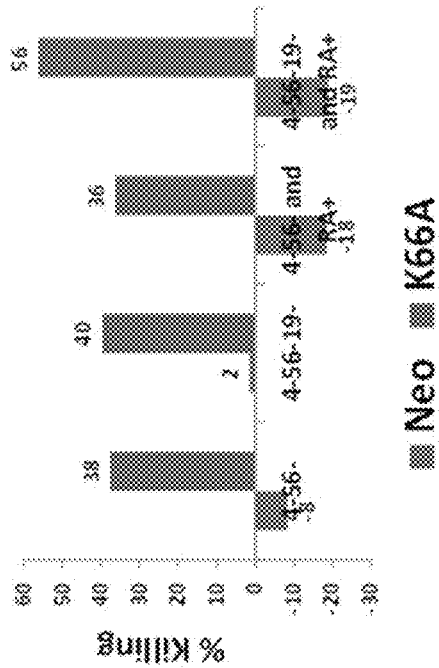
Figure 19D:
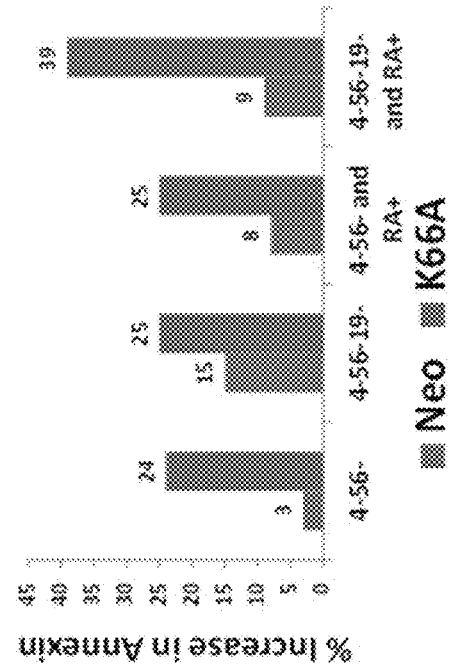

FIGS. 19A-19D depict H.My C1R ("Neo") and H.My C1R HLA A2 K66A mutant transfectant ("K66A") B-cell lymphoblastoid cell lines which were labeled with CalceinAM, a vital dye that is released upon cell death and then incubated for 22 hours with or without anti-$3^{rd}$ party Tcm cells at a 1 to 5 ratio in favor of anti-$3^{rd}$ party Tcm cells. After 22 hours, cells were recovered and analyzed for survival by measuring the number of surviving Calcein+ stained cells, and for apoptosis by AnnexinV+ cells from the calcein+ population by FACS. FIGS. 19A-19B and FIGS. 19C-19D represent two independent experiments, respectively; FIGS. 19A and 19C show killing while FIGS. 19B and 19D show apoptosis.

The percentage of B lymphoblast line cells killing was calculated by the following formula:

$$\left(1 - \frac{\text{The number of live } B \text{ lymphoblast line cells in the assessed well}}{\text{The number of live } B \text{ lymphoblast line cells in the control well}}\right) \times 100$$

Negative values signify that the B-cell lymphoblastoid cell lines proliferated in the presence of Tcm.

The percentage of B lymphoblast line cells undergoing specific apoptosis was calculated by the following formula: =(% Calcein+AnnexinV+ B lymphoblast line cells in the assessed well)−(% Calcein+AnnexinV+ B lymphoblast line cells in the control well).

FIG. 20 depicts the effect of different GMP grade reagents used for isolation of CD8 T cells on levels of K66A killing. H.My C1R HLA A2 K66A mutant transfectant cell lines were incubated for 22 hours with or without anti-3rd party Tcm cells at a 1 to 5 ratio in favor of anti-3rd party Tcm cells. After 22 hours, cells were recovered and analyzed for survival by measuring the number of surviving Calcein+ stained cells a by FACS (mean of two independent experiments). Average percent of killing of H.My C1R HLA A2 K66A mutant cells shown as percent of the levels attained by the optimal control group isolated making use of all four reagents (CD4/CD56/CD19/CD45RA).

Figure 22:
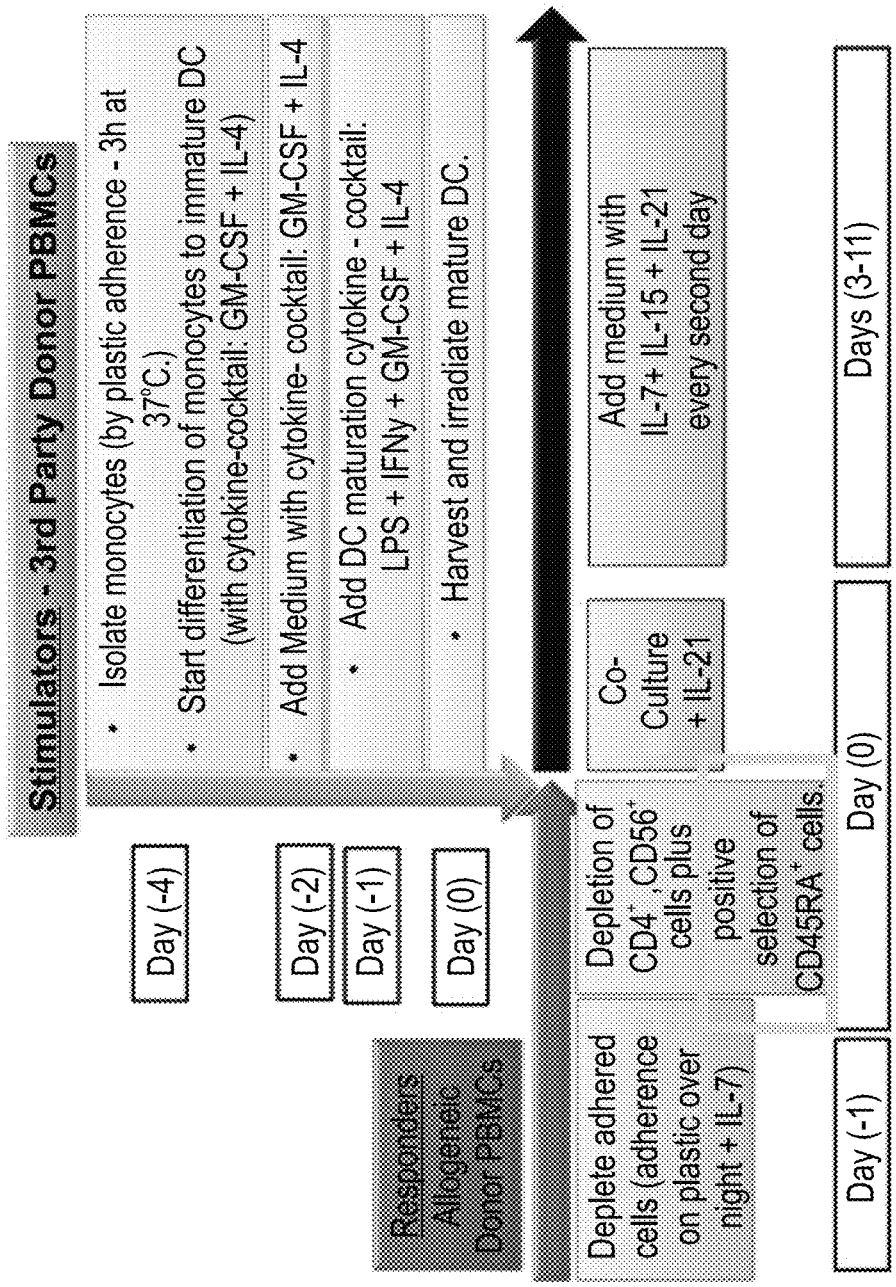

FIGS. 21-22 are schematic illustrations depicting protocols for generation of Tcm for autologous (FIG. 21) and allogeneic (FIG. 22) transplantation.

Figure 23A:
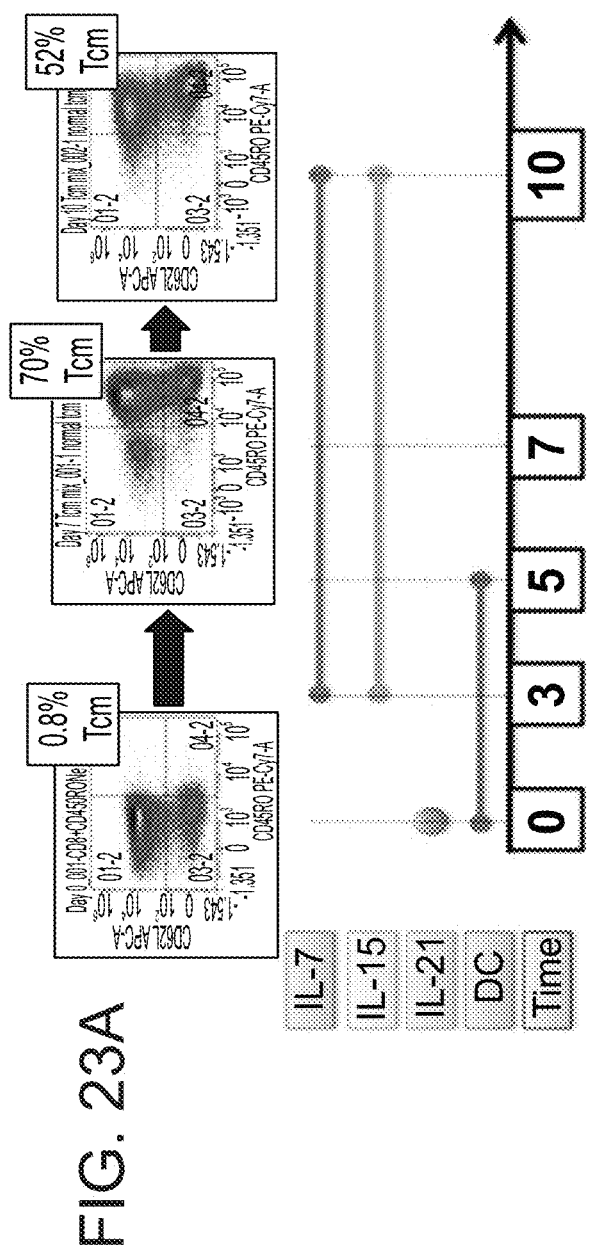
Figure 23B:
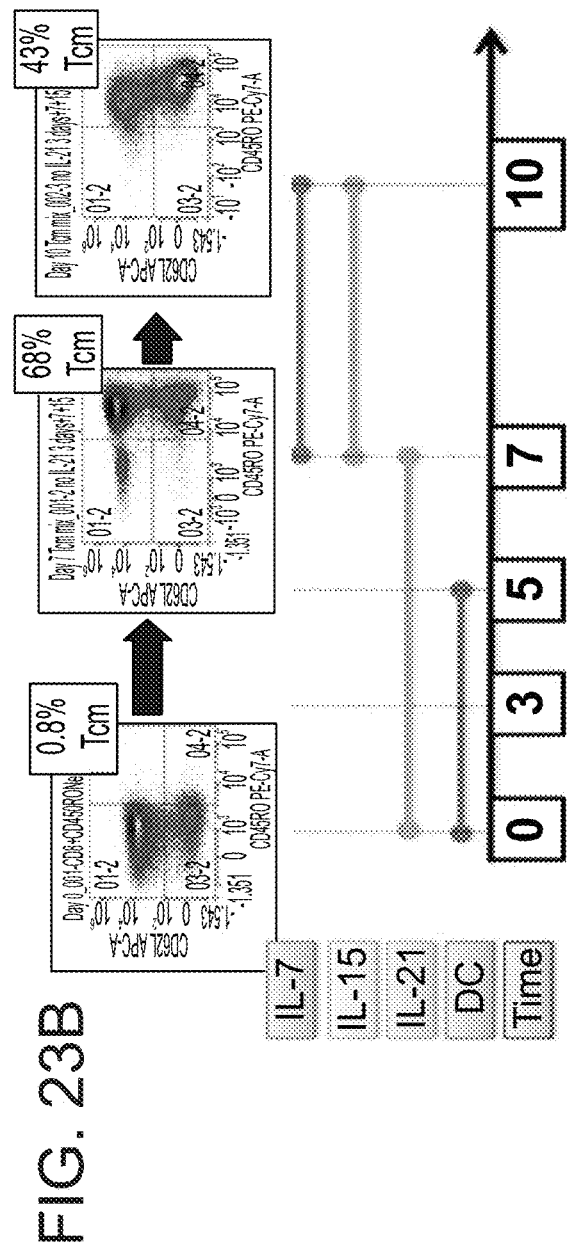
Figures 23C, 23D:
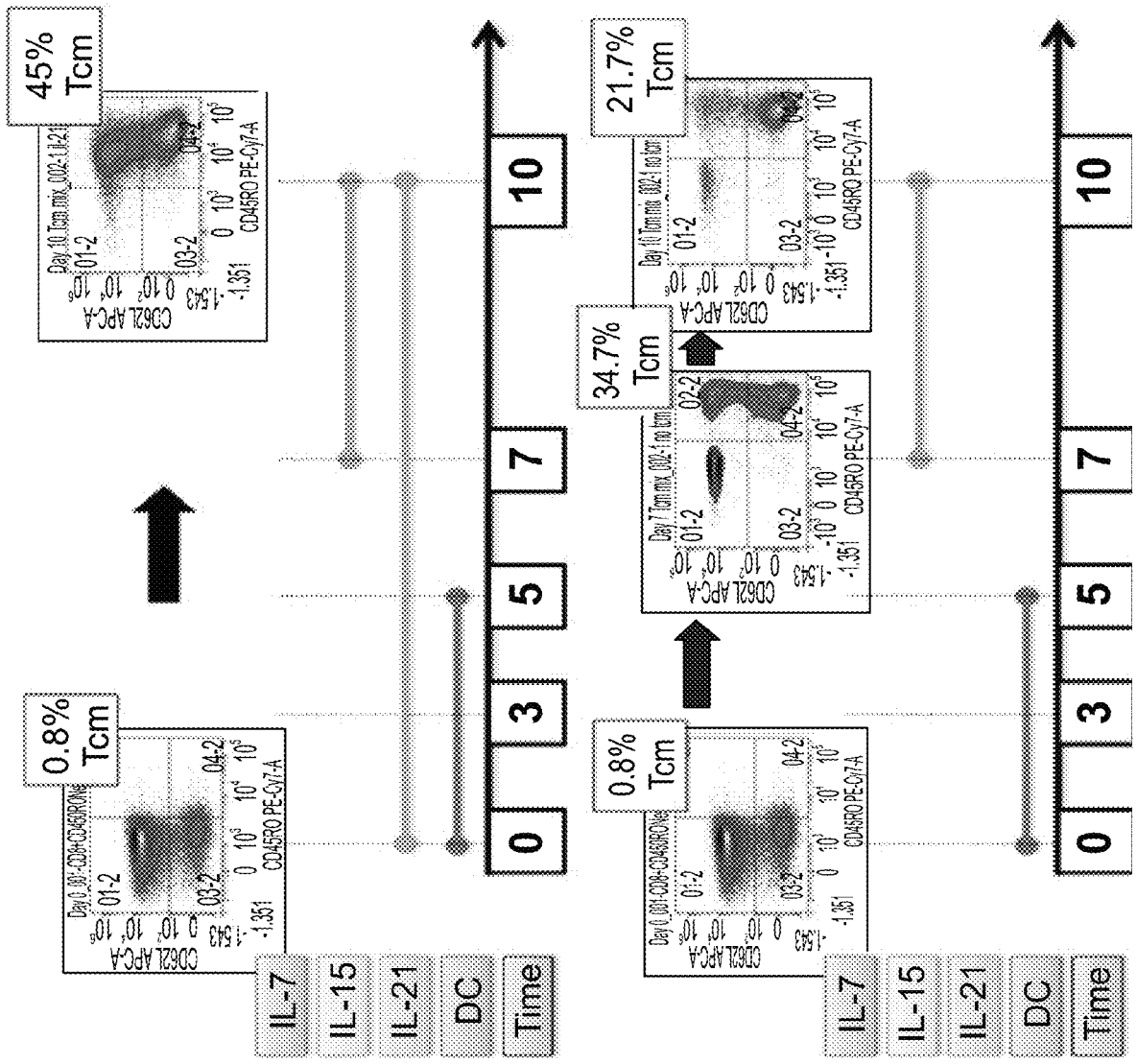

FIGS. 23A-23D depict a typical experiment demonstrating the role of timing of addition of cytokines on the induction of Tcm phenotype in CD8 T cells stimulated by allogeneic $3^{rd}$ party monocyte-derived mature DC. FIG. 23A illustrates naïve CD8 T cells which were stimulated with irradiated allogeneic 3rd party DC at a ratio of 4:1 in a medium containing IL-21 for 3 days. Thereafter the cells received no further activation and were expanded with IL-7 and IL-15 until day 13 ("reference control group"=d(0-3) IL21+DC d(3-13)IL7+IL15); FIG. 23B illustrates naïve CD8 T cells which were stimulated with irradiated allogeneic 3rd party DC at a ratio of 4:1 in the presence of IL-21 for 7 days. Thereafter the cells received no further activation and were expanded with IL-7 and IL-15 until day 13; FIG. 23C illustrates CD8 T cells which were stimulated with irradiated allogeneic 3rd party DC at a ratio of 4:1 with continuous presence of IL-21 in both the priming phase (IL21 alone) and in the expansion phase (together with IL-15); FIG. 23D illustrates CD8 T cells which were stimulated with irradiated allogeneic 3rd party DC at a ratio of 4:1 with cytokine deprivation for 7 days. Thereafter, the cells received no further activation and were expanded with IL-15 alone until day 13.

Figure 24B:
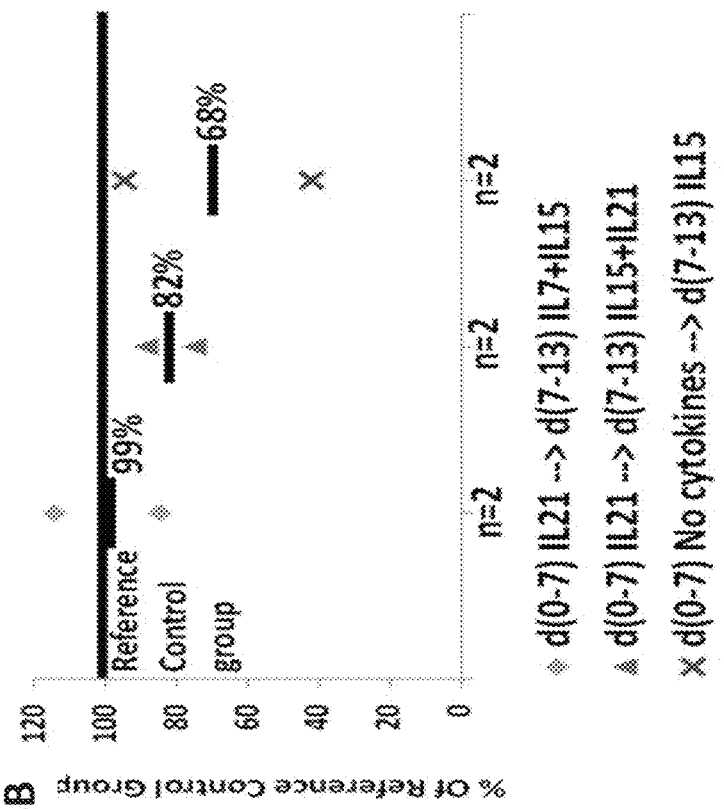
Figure 24A:
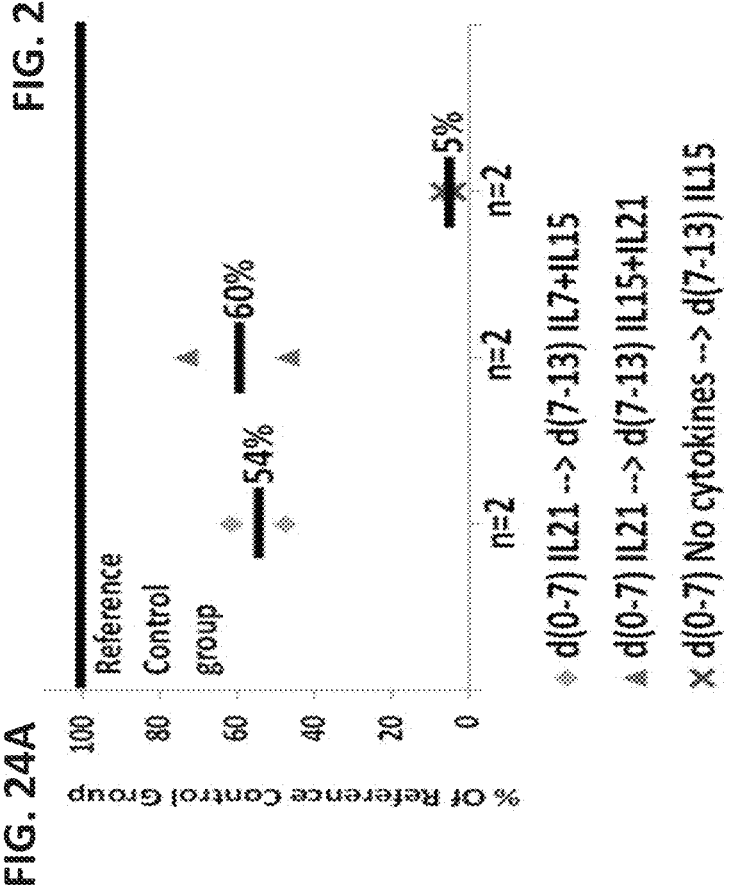

FIGS. 24A-24B depict the role of timing of addition of cytokines in the human allogeneic model; summary of experiments. Naïve CD8 T cells were stimulated with irradiated allogeneic 3rd party DC at a ratio of 4:1 in a medium containing IL-21 for 3 days. Thereafter the cells received no further activation and were expanded with IL-7 and IL-15 until day 13 ("reference control group"=d(0-3) IL21→d(3-13)IL7+IL15). The other groups were treated as indicated under the graphs. Cultures were evaluated for cell numbers by trypan blue exclusion (FIG. 24A), and percentage of Tcm (CD62L+CD45RO+) from CD8 T cells using FACS analysis (FIG. 24B). For each time point data represents average ±SE of the indicated number (n) of independent experiments.

Figure 25:
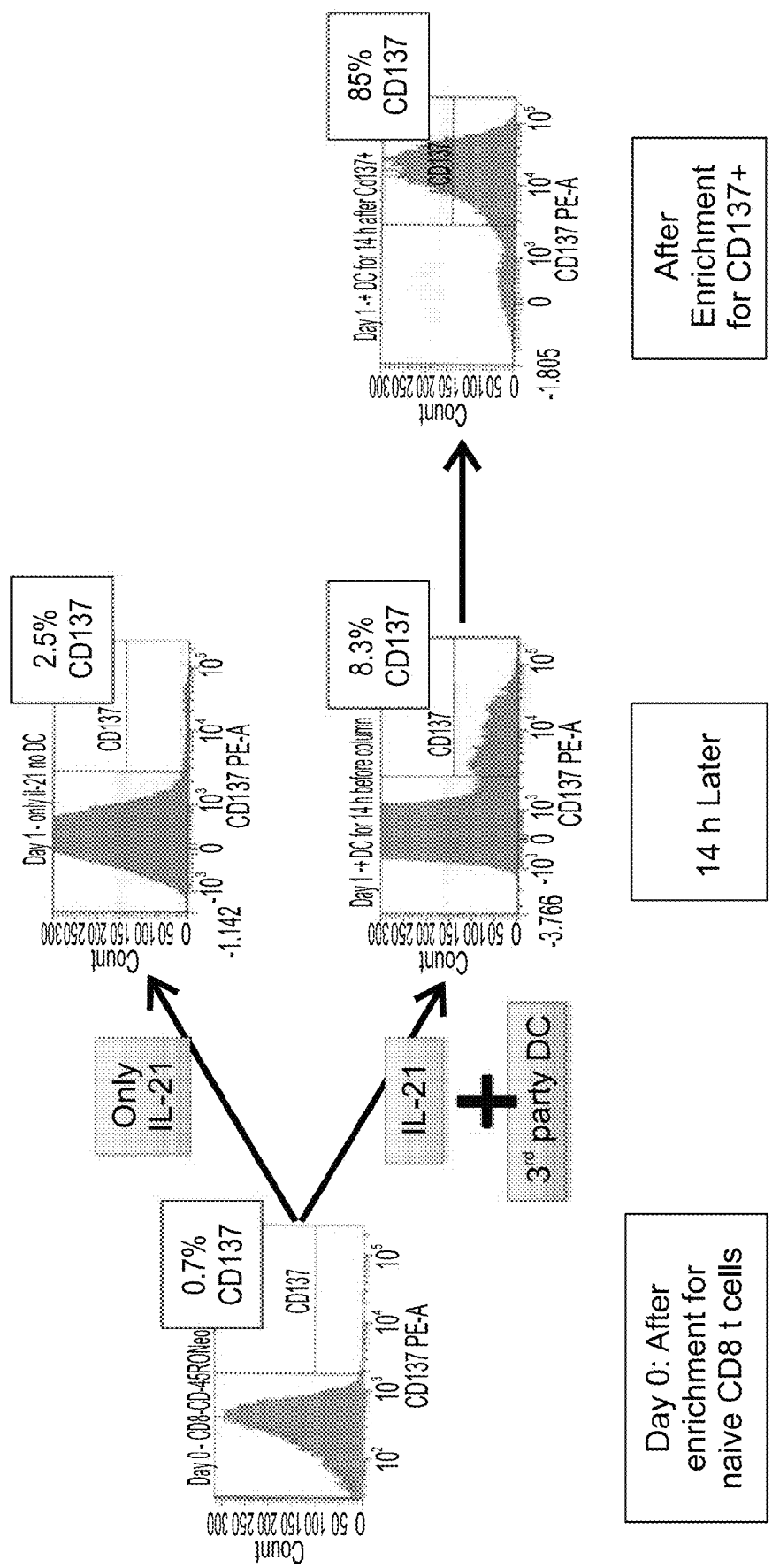

FIG. 25 depicts enrichment of anti-$3^{rd}$ party specific CD8 T cell by positive selection of CD137+ cells. Naïve CD8 T cells were stimulated with irradiated allogeneic 3rd party DC (at a ratio of 5.7:1) in the presence of IL-21. After 14 hours of activation, CD137+ cells were positively selected by magnetic sorting. The expression of CD137 on CD8 T cells was evaluated by FACS.

Figure 26:
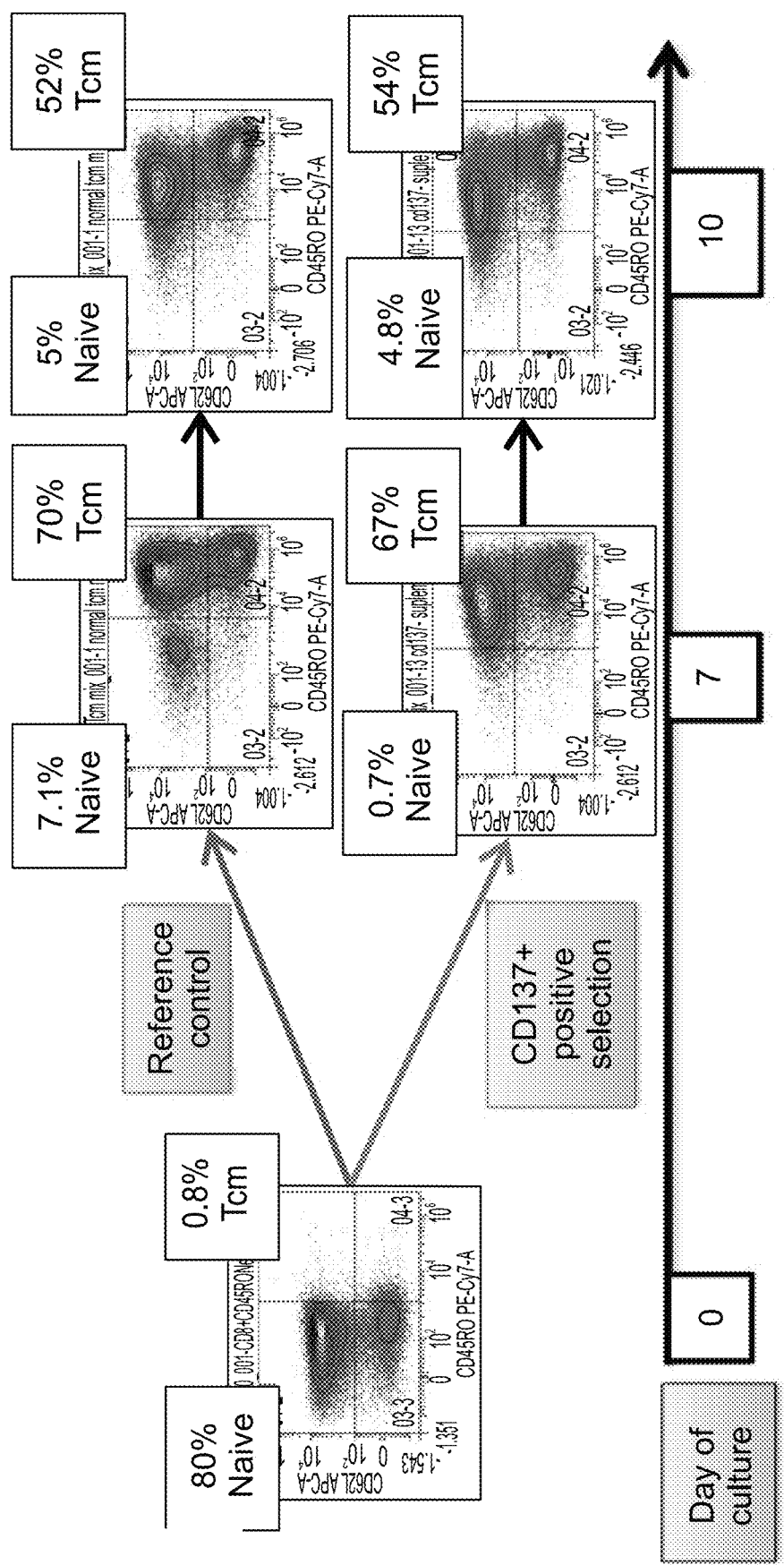

FIG. 26 depicts that enrichment of anti-$3^{rd}$ party specific CD8 T cell by positive selection of CD137+ cells does not reduce acquisition of Tcm phenotype. Naïve CD8 T cells were stimulated with irradiated allogeneic 3rd party DC at a ratio of 4:1 in the presence of IL-21 for 3 days. Thereafter, the cells received no further activation and were expanded with IL-7 and IL-15 until day 10 ("Reference control group"). Alternatively, naïve CD8 T cells were stimulated with irradiated allogeneic 3rd party DC at a ratio of 5.7:1 in the presence of IL-21. After 14 hours of activation, CD137+ cells were positively selected by magnetic sorting. CD137+ cells were then re-stimulated with irradiated allogeneic 3rd party DC at a ratio of 4:1 in the presence of IL-21 until day 3. Thereafter the cells were expanded with IL-7 and IL-15 until day 10. Cells were evaluated for percentage of Tcm (CD62L+CD45RO+) from CD8 T cells by FACS analysis.

Figure 27:
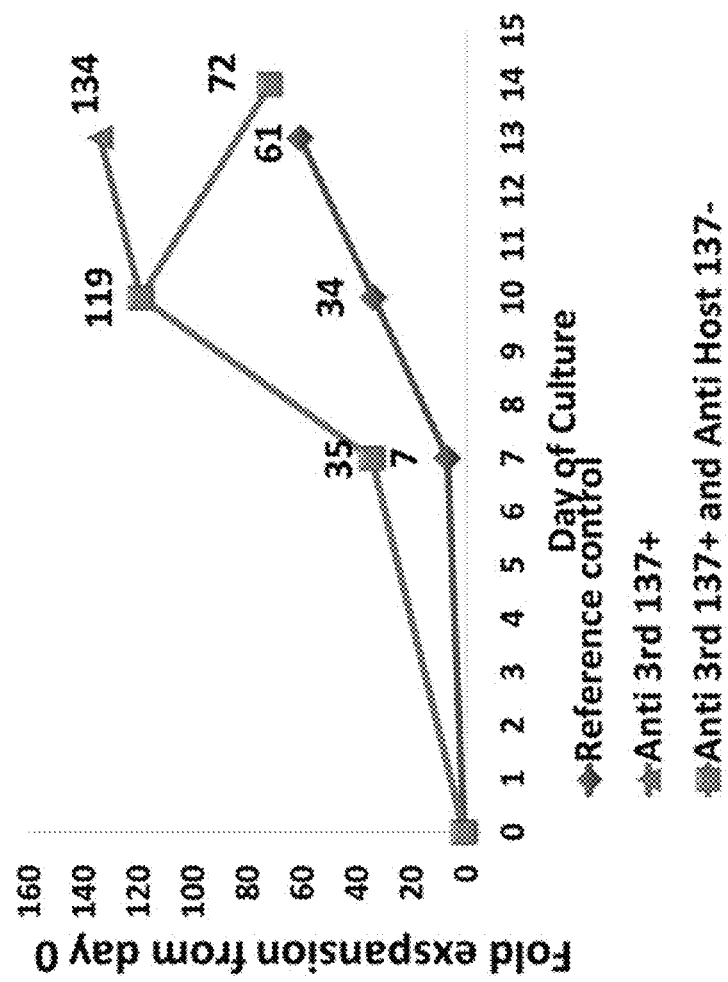

FIG. 27 depicts a comparison of proliferation kinetics. Naïve CD8 T cells were stimulated with irradiated allogeneic 3rd party DC at a ratio of 4:1 in the presence of IL-21 for 3 days. The cells received no further activation thereafter and were expanded with IL-7 and IL-15 until day 14 ("Reference control group"). Alternatively, naïve CD8 T cells were stimulated with irradiated allogeneic 3rd party DC at a ratio of 5.7:1 in the presence of IL-21. After 14 hours of activation, CD137+ cells were positively selected by magnetic sorting. CD137+ cells were then re-stimulated with irradiated allogeneic 3rd party DC in at a ratio of 4:1 in the presence of IL-21 until day 3. Thereafter, the cells were expanded with IL-7 and IL-15 until day 10. On day 10, cells were divided into two test groups. In the first group cells continued to be expanded with IL-7 and IL-15 until day 14 ("Anti $3^{rd}$ CD137+") while cells in the second test group were activated with irradiated host PBMC in the presence of IL-7 and IL-15 (at a ratio of 1 to 2). After 24 hours, CD137+ cells were depleted by magnetic sorting. The CD137 depleted cells were re-plated with IL-7 and IL-15 and cultured until day 14 ("Anti $3^{rd}$ CD137+ and Anti host CD137−"). On the indicated days, cells were counted by trypan blue exclusion.

Figure 28:
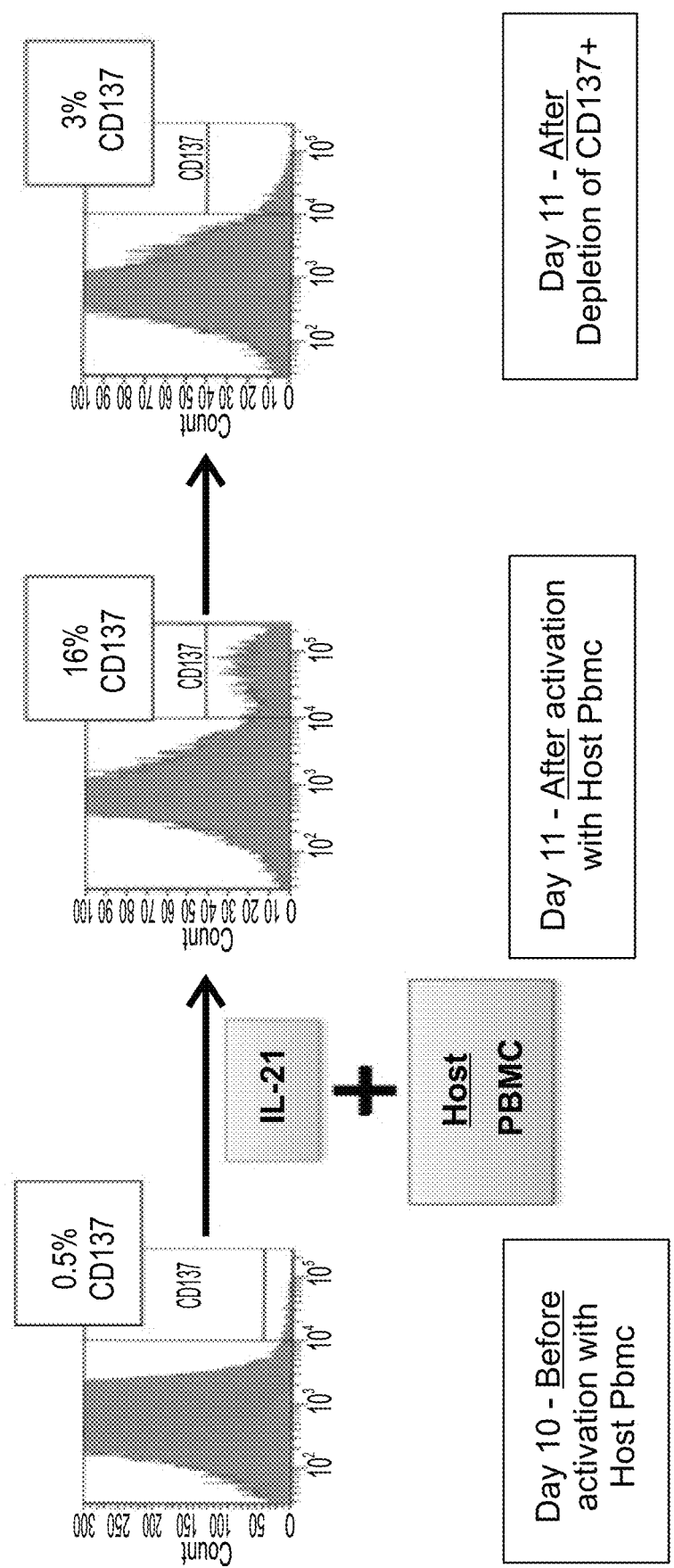

FIG. 28 depicts depletion of anti-host specific clones by depletion of CD137+ cells after activation with irradiated host PBMC. On day 10 of culture, 9 days after positive selection of anti-3$^{rd}$ party specific clones, cells were activated by irradiated host PBMC (at a 1:2 ratio, in favor of the host PBMC) in the presence of IL-7 and IL-15. After 24 h, cells were depleted of CD137+ cells. The expression of CD137 on CD8 T cells was evaluated by FACS analysis.

Figure 29:
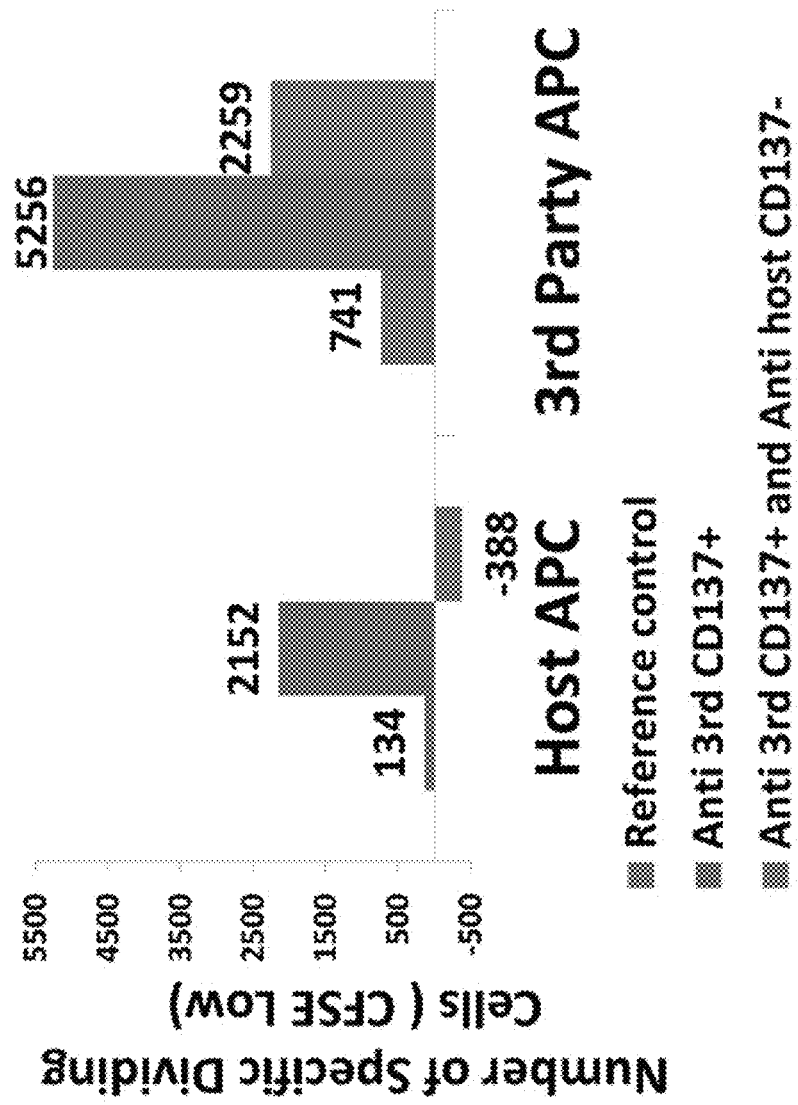

FIG. 29 depicts a two stage magnetic sorting technique, based on CD137 upregulation after antigen specific activation of CD8 T cells successfully depletes anti-host clones and increases the percent of cells specific for 3$^{rd}$ party antigens. Naïve CD8 T cells were stimulated with irradiated allogeneic 3rd party DC at a ratio of 4:1 in the presence of IL-21 for 3 days. The cells received no further activation thereafter and were expanded with IL-7 and IL-15 until day 14 ("Reference control group"). Alternatively, naïve CD8 T cells were stimulated with irradiated allogeneic 3rd party DC at a ratio of 5.7:1 in the presence of IL-21. After 14 hours of activation, CD137+ cells were positively selected by magnetic sorting. CD137+ cells were then re-stimulated with irradiated allogeneic 3rd party DC in at a ratio of 4:1 in the presence of IL-21 until day 3. Thereafter, the cells were expanded with IL-7 and IL-15 until day 10. On day 10, cells were divided into two test groups. In the first group cells continued to be expanded with IL-7 and IL-15 until day 14 ("Anti 3$^{rd}$ CD137+") while cells in the second test group were activated with irradiated host PBMC in the presence of IL-7 and IL-15 (at a ratio of 1 to 2). After 24 h, CD137+ cells were depleted by magnetic sorting. The CD137 depleted cells were re plated with IL-7 and IL-15 and cultured until day 14 ("Anti 3$^{rd}$ CD137+ and Anti host CD137−"). On day 14, anti 3rd party and anti-host alloreactivity was evaluated by CFSE assay against 3rd party or irradiated host PBMCs. For the CFSE assay, 1×10$^6$ CFSE+ responders were incubated with or without 2×10$^6$ irradiated (20 gy) PBMC stimulators for 84 h in the presence of IL-7. After 84 h, cells were recovered and analyzed for cell division by measuring the number of CFSE low stained CD8 T cells (CD3+CD8+ CD56−) cells by FACS. To obtain absolute values of cells, samples were suspended in a constant volume and flow cytometric counts for each sample were obtained during a constant, predetermined period of time. The number of specific dividing cells=(Number of dividing cell with APC)− (Number of dividing cell without APC). Negative values signify that the number of dividing cells in response to activation with host PBMC was even lower that the number of dividing cell without any activation.

DESCRIPTION OF SPECIFIC EMBODIMENTS OF THE INVENTION

The present invention, in some embodiments thereof, relates to tolerance inducing and/or graft versus leukemia reactive anti-third party cells comprising central memory T-lymphocyte phenotype and, more particularly, but not exclusively, to methods of generating same and to the use of same in transplantation and in disease treatment.

The principles and operation of the present invention may be better understood with reference to the drawings and accompanying descriptions.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

While reducing the present invention to practice, the present inventors have uncovered an improved population of anti-third party central memory T (Tcm) cells which homes to the lymph nodes following transplantation and induces tolerance and anti-disease activity (e.g. graft versus leukemia (GVL) activity) without inducing a graft versus host (GVH) reaction.

Figure 1A:
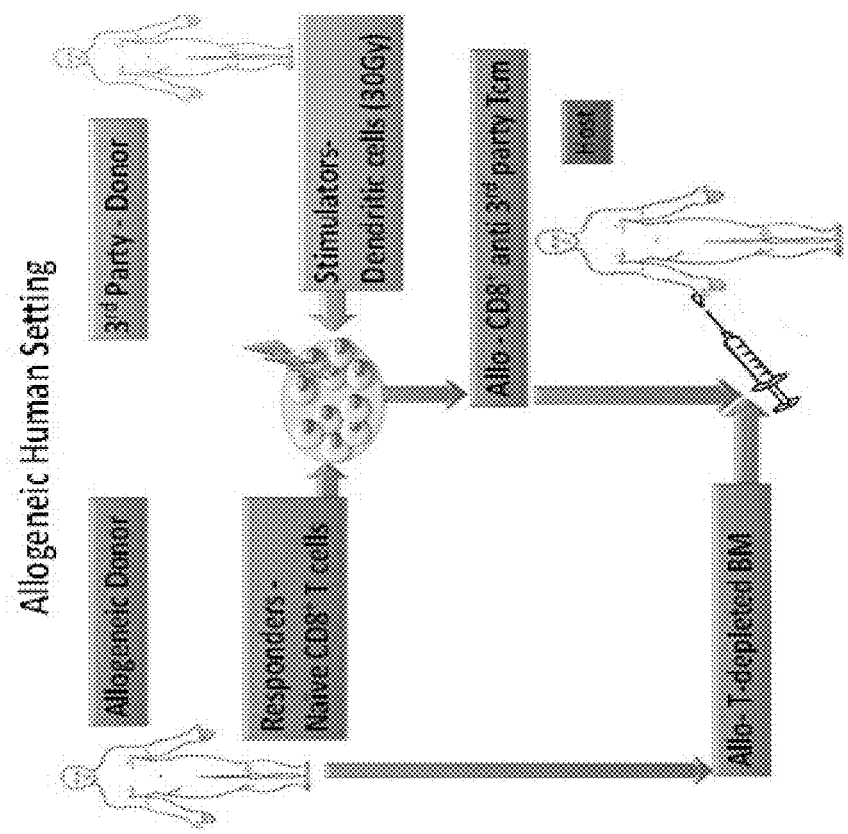

As is shown hereinbelow and in the Examples section which follows, the present inventors have provided new methods of generating Tcm cells for allogeneic and autologous applications. As shown in FIGS. 1A and 21, autologous Tcm cells, which are endowed with anti-disease activity (e.g. anti-tumor activity), were generated by first exposing CD8$^+$ T cells to allogeneic stimuli (e.g. dendritic cells) in the presence of IL-21 for 3 days and subsequently adding IL-15 and IL-7 to the cells with the antigenic stimuli for another 1-2 days. Next, the resultant cells were cultured in an antigen free environment in the presence of IL-21, IL-15 and IL-7 for additional 6-8 days.

Figure 1B:
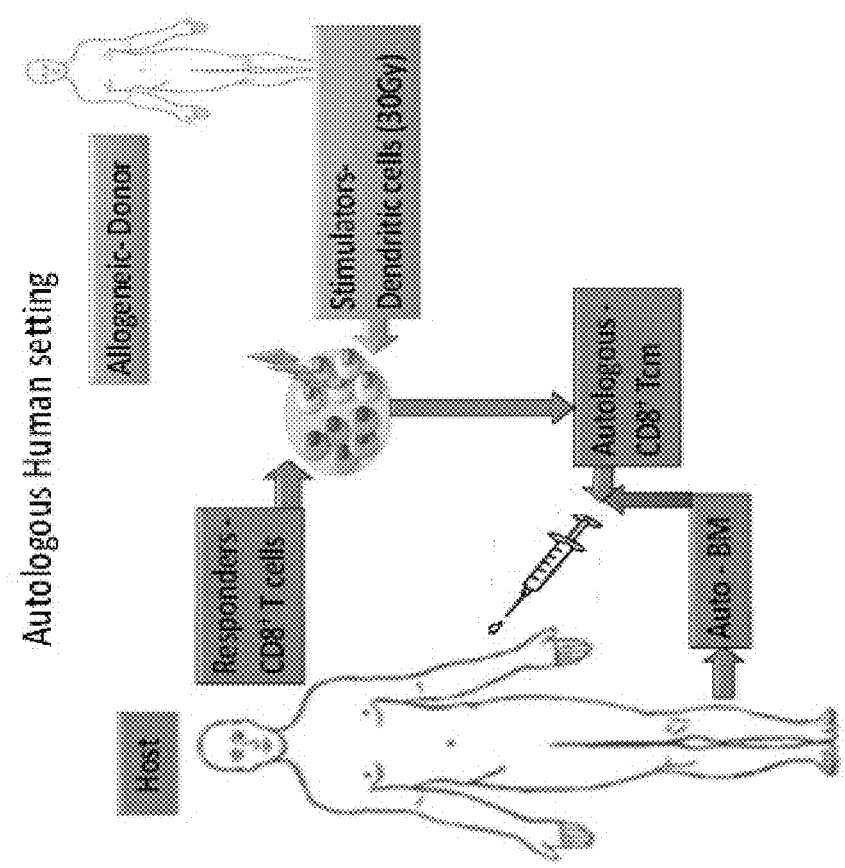
Figure 2A:
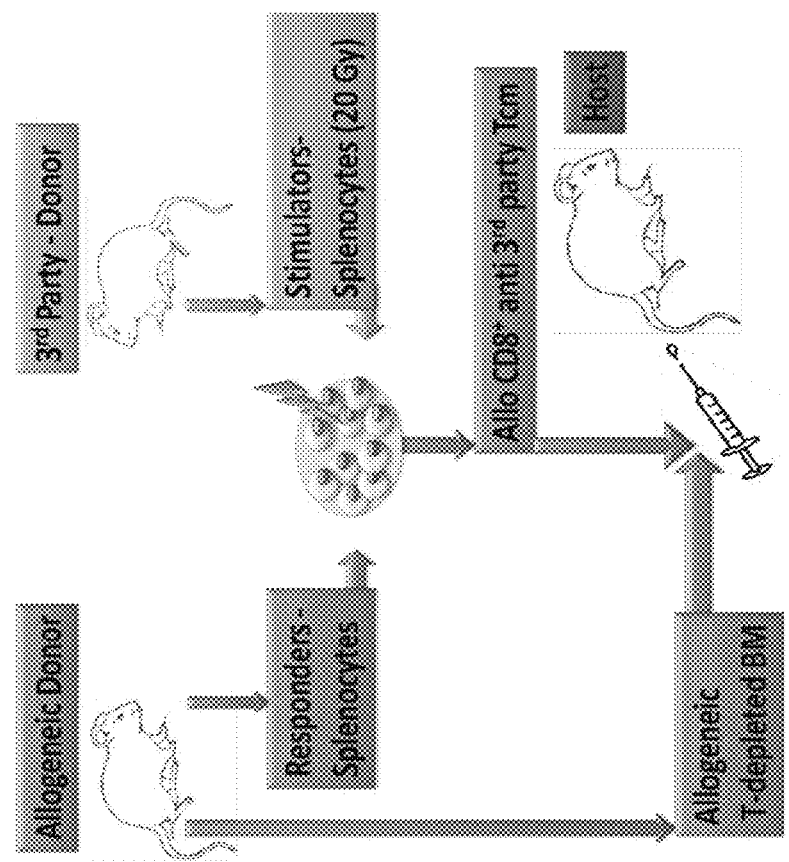
Figure 2B:
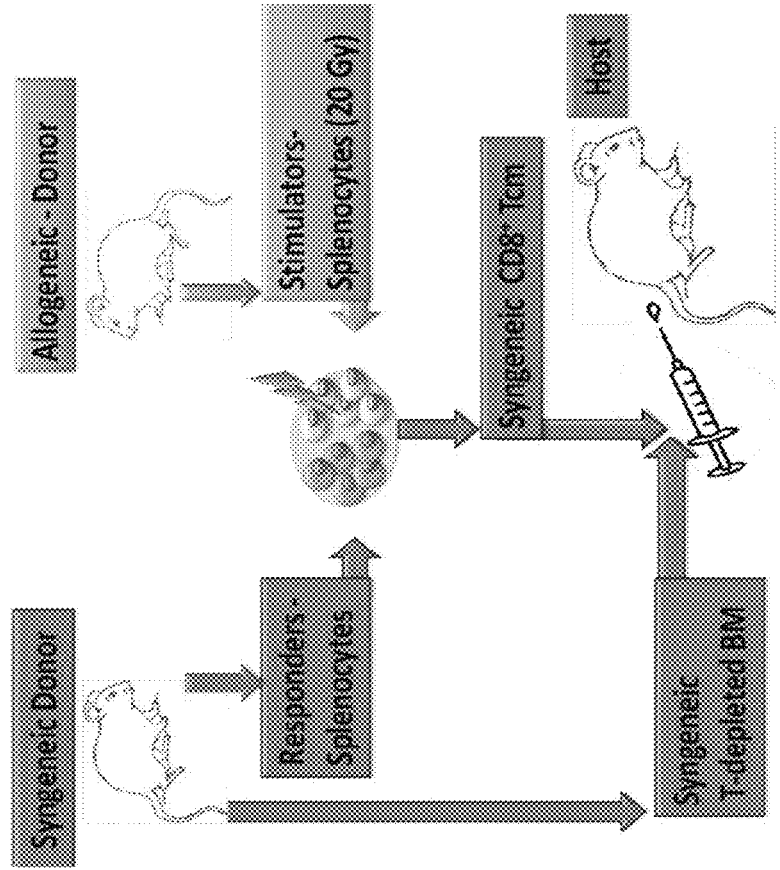

As depicted in FIGS. 1B and 22, allogeneic Tcm cells, which are tolerance inducing cells and are endowed with GVL activity, were generated by first exposing CD8$^+$ T cells to a third party stimuli (e.g. dendritic cells) in the presence of IL-21 for 3 days. Approximately 14 hours from the beginning of culture, the activated cells were selected by positive selection of CD137+, and these cells were re-cultured with IL-21. Subsequently, IL-15 and IL-7 were added to the IL-21 culture with the antigenic stimuli for another 1-2 days. Next, the resultant cells were cultured in an antigen free environment in the presence of IL-21, IL-15 and IL-7 for additional 6-8 days. At the end of culture, the Tcm cells were depleted of alloreactive cells by depletion of CD137+ cells following contacting of the Tcm cells with host type antigen presenting cells (e.g. dendritic cells).

The cells generated by the present inventors comprised more than 50% CD3+CD8+ cells of which more than 50% are Tcm cells (i.e. comprise a CD3$^+$, CD8$^+$, CD62L$^+$, CD45RA$^−$, CD45RO$^+$ signature see e.g. Example 1 of the Examples section which follows) and comprised TCR independent anti-leukemic activity (see Example 2).

Taken together, these results substantiate the use of anti-third party Tcm cells as graft facilitating cells and for use in disease treatment in situations in which allogeneic transplantation is warranted (e.g. hematopoietic stem cell transplantation or in solid organ transplantation). Furthermore, these results substantiate the use anti-third party Tcm cells in disease treatment in situations in which autologous transplantation is needed, such as for hematological malignancies.

Thus, according to one aspect of the present invention there is provided an isolated population of cells comprising non-GVHD inducing anti-third party cells having a central memory T-lymphocyte (Tcm) phenotype, the cells being tolerance-inducing cells and capable of homing to the lymph nodes following transplantation.

The phrase "isolated population of cells" as used herein refers to cells which have been isolated from their natural environment (e.g., the human body).

The term "non-GVHD" as used herein refers to having substantially reduced or no graft versus host inducing reactivity. Thus, the cells of the present invention are generated as to not significantly cause graft versus host disease (GVHD) as evidenced by survival, weight and overall appearance of the transplanted subject 100 days following transplantation.

As used herein, the term "syngeneic" refers to a cell or tissue which is derived from an individual who is essentially genetically identical with the subject. Typically, essentially fully inbred mammals, mammalian clones, or homozygotic twin mammals are syngeneic.

Examples of syngeneic cells or tissues include cells or tissues derived from the subject (also referred to in the art as "autologous"), a clone of the subject, or a homozygotic twin of the subject.

As used herein, the term "non-syngeneic" refers to a cell or tissue which is derived from an individual who is allogeneic or xenogeneic with the subject's lymphocytes.

As used herein, the term "allogeneic" refers to a cell or tissue which is derived from a donor who is of the same species as the subject, but which is substantially non-clonal with the subject. Typically, outbred, non-zygotic twin mammals of the same species are allogeneic with each other. It will be appreciated that an allogeneic donor may be HLA identical or HLA non-identical with respect to the subject.

As used herein, the term "xenogeneic" refers to a cell or tissue which substantially expresses antigens of a different species relative to the species of a substantial proportion of the lymphocytes of the subject. Typically, outbred mammals of different species are xenogeneic with each other.

The present invention envisages that xenogeneic cells or tissues are derived from a variety of species such as, but not limited to, bovines (e.g., cow), equids (e.g., horse), porcines (e.g. pig), ovids (e.g., goat, sheep), felines (e.g., *Felis domestica*), canines (e.g., *Canis domestica*), rodents (e.g., mouse, rat, rabbit, guinea pig, gerbil, hamster) or primates (e.g., chimpanzee, rhesus monkey, macaque monkey, marmoset).

Cells or tissues of xenogeneic origin (e.g. porcine origin) are preferably obtained from a source which is known to be free of zoonoses, such as porcine endogenous retroviruses. Similarly, human-derived cells or tissues are preferably obtained from substantially pathogen-free sources.

The phrase "anti-third party cells" as used herein refers to lymphocytes (e.g. T lymphocytes) which are directed (e.g. by T cell recognition) against a third party antigen or antigens.

As used herein the phrase "third party antigen or antigens" refers to a soluble or non-soluble (such as membrane associated) antigen or antigens which are not present in either the donor or recipient, as depicted in detail infra.

For example, third party antigens can be third party cells, antigens of viruses, such as for example, Epstein-Barr virus (EBV) or cyto-megalo virus (CMV) or antigens of bacteria, such as flagellin. Viral or bacterial antigens can be presented by cells (e.g., cell line) infected therewith or otherwise made to express viral/bacterial proteins. Autologous or non-autologous antigen presenting cells can be used to present short synthetic peptides fused or loaded thereto. Such short peptides may be viral derived peptides or peptides representing any other antigen.

Dedicated software can be used to analyze viral or other sequences to identify immunogenic short peptides, i.e., peptides presentable in context of class I MHC or class II MHC.

Third party cells can be either allogeneic or xenogeneic with respects to the recipient (explained in further detail hereinbelow). In the case of allogeneic third party cells, such cells have HLA antigens different from that of the donor but which are not cross reactive with the recipient HLA antigens, such that anti-third party cells generated against such cells are not reactive against a transplant or recipient antigens.

According to an embodiment of the present invention the allogeneic or xenogeneic third party cells are stimulatory cells selected from the group consisting of cells purified from peripheral blood lymphocytes (PBL), spleen or lymph nodes, cytokine-mobilized PBLs, in vitro expanded antigen-presenting cells (APC), in vitro expanded dendritic cells (DC) and artificial antigen presenting cells.

The artificial APC of the present invention may be engineered to exhibit autologous MHC with a $3^{rd}$ party peptide or a $3^{rd}$ party MHC without being pulsed with an exogenous peptide. Thus, according to one embodiment, the artificial APC comprises K562 tumor cells transfected with a third party MHC determinant and a co-stimulatory molecule [as previously described e.g. Suhoski M M et al., Mol Ther. (2007) 15(5): 981-8], or fibroblasts transfected with same.

Third party antigens can be presented on the cellular, viral or bacterial surfaces or derived and/or purified therefrom. Additionally, a viral or bacterial antigen can be displayed on an infected cell and a cellular antigen can be displayed on an artificial vehicle such as a liposome or an artificial antigen presenting cell (e.g. leukemic or fibroblast cell line transfected with the third party antigen or antigens).

The third party antigen may further comprise a synthetic peptide presented by autologous presenting cells, non-autologous presenting cells or on an artificial vehicle or on artificial antigen presenting cells.

In addition, third party antigens can, for example, be proteins extracted or purified from a variety of sources. An example of a purified protein which can serve as a third party antigen according to the present invention is ovalbumin. Other examples are envisaged.

Utilizing cells, viruses, bacteria, virally infected, bacteria infected, viral peptides or bacteria peptides presenting cells as third party antigens is particularly advantageous since such third party antigens include a diverse array of antigenic determinants and as such direct the formation of anti-third party cells of a diverse population, which may further serve in faster reconstitution of T-cells in cases where such reconstitution is required, e.g., following lethal or sublethal irradiation or chemotherapy procedure.

Furthermore, when anti-third party cells are directed against third party antigens, the cells are endowed with anti-disease activity. The term "anti-disease activity" refers to the activity (e.g. killing capability) of the Tcm cells against a diseased cell (e.g. cancer cell, such as graft versus leukemia, GVL, activity). This activity is typically due to TCR independent killing mediated by LFA1-I/CAM1 binding [Arditti et al., Blood (2005) 105(8):3365-71. Epub 2004 Jul. 6].

According to one embodiment, the third party cells comprise dendritic cells.

According to one embodiment, the third party cells comprise mature dendritic cells.

Methods of generating third party dendritic cells, which may be used as stimulatory cells for inducing Tcm cells, are well known in the art. Thus, as a non-limiting example, peripheral blood mononuclear cells (PBMC) may be obtained from a third party non-syngeneic cell donor [e.g. in case the Tcm cells are syngeneic, e.g. autologous, the dendritic cells (DCs) may be non-syngeneic, e.g. allogeneic, with respect to the subject; whereas if the Tcm cells are non-syngeneic, e.g. allogeneic, the DCs are selected from a donor being non-syngeneic, e.g. allogeneic, and HLA mismatched with both the subject and the Tcm cells]. Monocytes may then be isolated by plastic adherence and cultured (e.g. in cell culture plates) using DC cell medium (e.g. Cellgro DC medium) supplemented with human serum (e.g. 1% human serum), penicillin/streptomycin and GM-CSF (800 IU/ml) and IL-4 (20 ng/ml) (available from e.g. Peprotech, Hamburg, Germany). After about 48 h of culture, DC medium may be added comprising GM-CSF (1600 IU/ml) and IL-4 (20 ng/ml). About 24 h later, non-adherent cells may be harvested, and large cells (mostly immature DC) may be resuspended in fresh medium containing GM-CSF (800 IU/ml), IL-4 (20 ng/ml), LPS (e.g. from E. coli 055:B5 at 10 ng/ml) and IFNγ 100 IU/ml) (available from e.g. Peprotech, Hamburg, Germany), plated and incubated overnight. The next day, non-adherent cells may be discarded, and adherent DCs may be gently removed using e.g. cold PBS/1% HS after incubation on ice for 20 minutes, thereby obtaining large cells consisting of mature DC.

According to one embodiment, the third party cells comprise irradiated dendritic cells.

Thus, according to one embodiment, the DCs are irradiated with about 5-10 Gy, about 10-20 Gy, about 20-30 Gy, about 20-40 Gy, about 20-50 Gy, about 10-50 Gy. According to a specific embodiment, the DCs are irradiated with about 10-50 Gy (e.g. 30 Gy).

According to some embodiments, the anti-third party cells of the present invention comprise a central memory T-lymphocyte (Tcm) phenotype.

The phrase "central memory T-lymphocyte (Tcm) phenotype" as used herein refers to a subset of T cytotoxic cells which home to the lymph nodes. Cells having the Tcm phenotype, in humans, typically comprise a CD3+/CD8+/CD62L+/CD45RO+/CD45RA− signature. It will be appreciated that Tcm cells may express all of the signature markers on a single cell or may express only part of the signature markers on a single cell.

It will be appreciated that at least 30%, at least 40%, at least 50%, at least 55%, at least 60%, at least 65%, at least 70%, at least 75%, at least 80%, at least 85%, at least 90%, at least 95% or even 100% of the isolated population of cells are CD3+CD8+ cells. According to a specific embodiment, the isolated population of cells comprise about 70-90% CD3+CD8+ cells.

It will be appreciated that at least 30%, at least 40%, at least 50%, at least 55%, at least 60%, at least 65%, at least 70%, at least 75%, at least 80%, at least 85%, at least 90%, at least 95% or even 100% of the CD3+CD8+ cells have the Tcm cell signature. According to a specific embodiment, about 30-80% of the CD3+CD8+ cells have the Tcm cell signature (e.g. 40-50%).

According to one embodiment, there is provided an isolated population of cells comprising anti-third party cells having a central memory T-lymphocyte (Tcm) phenotype, wherein at least 50% of the isolated population of cells are CD3+CD8+ cells of which at least 50% comprise a CD3$^+$, CD8$^+$, CD62L$^+$, CD45RA$^−$, CD45RO$^+$ signature, and further wherein the cells are tolerance-inducing cells and/or endowed with anti-disease activity (e.g. graft-versus-leukemia (GVL) activity), and capable of homing to the lymph nodes following transplantation.

As mentioned, the Tcm cells typically home to the lymph nodes following transplantation. According to some embodiments the anti-third party Tcm cells of the present invention may home to any of the lymph nodes following transplantation, as for example, the peripheral lymph nodes and mesenteric lymph nodes. The homing nature of these cells allows them to exert their tolerance effect in a rapid and efficient manner.

Thus, the anti-third party Tcm cells of the present invention are tolerance-inducing cells.

The phrase "tolerance inducing cells" as used herein refers to cells which provoke decreased responsiveness of the recipient's cells (e.g. recipient's T cells) when they come in contact with same as compared to the responsiveness of the recipient's cells in the absence of administered tolerance inducing cells. Tolerance inducing cells include veto cells (i.e. T cells which lead to apoptosis of host T cells upon contact with same) as was previously described in PCT Publication Nos. WO 2001/049243 and WO 2002/102971.

According to some embodiments, the Tcm cells of the present invention may be non-genetically modified cells or genetically modified cells (e.g. cells which have been genetically engineered to express or not express specific genes, markers or peptides or to secrete or not secrete specific cytokines). Any method known in the art may be implemented in genetically engineering the cells, such as by inactivation of the relevant gene/s or by insertion of an antisense RNA interfering with polypeptide expression (see e.g. WO/2000/039294, which is hereby incorporated by reference).

According to some embodiments of the invention there is provided a method of generating the isolated population of cells, the method comprising: (a) contacting peripheral blood mononuclear cells (PBMC) with a third party antigen or antigens in the presence of IL-21 so as to allow enrichment of antigen reactive cells; and (b) culturing the cells resulting from step (a) in the presence of IL-21, IL-15 and IL-7 in an antigen free environment so as to allow proliferation of cells comprising the central memory T-lymphocyte (Tcm) phenotype.

The anti-third party Tcm cells of the present invention are typically generated by first contacting syngeneic or non-syngeneic peripheral blood mononuclear cells (PBMC) with a third party antigen or antigens (such as described above) in a culture supplemented with IL-21 (otherwise cytokine-free culture i.e., without the addition of any additional cytokines). This step is typically carried out for about 12-24 hours, about 12-36 hours, about 12-72 hours, 24-48 hours, 24-36 hours, about 24-72 hours, about 48-72 hours, 1-2 days, 2-3 days, 1-3 days, 2-4 days, 1-5 days, 2-5 days, 2-6 days, 1-7 days, 5-7 days, 2-8 days, 8-10 days or 1-10 days and allows enrichment of antigen reactive cells. According to a specific embodiment, contacting of syngeneic or non-syngeneic PBMC with a third party antigen or antigens (such as described above) in a culture supplemented with IL-21 (otherwise cytokine-free culture) is effected for 1-5 days (e.g. 3 days. This step is typically carried out in the presence of about 0.001-3000 ng/ml, 0.001-1000 ng/ml, 0.01-1000 ng/ml, 0.1-1000 ng/ml, 1-1000 ng/ml, 10-1000 ng/ml, 10-500 ng/ml, 10-300 ng/ml, 10-100 ng/ml, 100-1000 ng/ml, 1-100 ng/ml, 1-50 ng/ml, 1-30 ng/ml, 10-50 ng/ml, 10-30 ng/ml, 10-20 ng/ml, 20-30 ng/ml, 20-50 ng/ml, 30-50 ng/ml, 30-100 ng/ml, 1-10 ng/ml, 0.1-10 ng/ml, 0.1-100 ng/ml, 1 ng/ml, 10 ng/ml-100 ng/ml IL-21. According to a specific embodiment, the concentration of IL-21 is 10-50 ng/ml (e.g. 30 ng/ml).

According to a specific embodiment, contacting the syngeneic or non-syngeneic PBMC with a third party antigen or antigens is effected in a cytokine free culture (e.g. supplemented with only IL-21), such a culture condition enables survival and enrichment of only those cells which undergo stimulation and activation by the third party antigen or antigens (i.e. of antigen reactive cells) as these cells secrete cytokines (e.g. IL-2) which enable their survival (all the rest of the cells die under these culture conditions).

The ratio of third party antigen or antigens (e.g. dendritic cell) to PBMC is typically about 1:2 to about 1:10 such as about 1:4, about 1:6, about 1:8 or about 1:10. According to a specific embodiment, the ratio of third party antigen or antigens (e.g. dendritic cell) to PBMC is about 1:2 to about 1:8 (e.g. 1:4).

Next, the anti-third party cells are cultured in the presence of IL-21, IL-15 and IL-7 in an antigen free environment so as to allow proliferation of cells comprising the Tcm phenotype. This step is typically carried out for about 12-24 hours, about 12-36 hours, about 12-72 hours, 24-48 hours, 24-36 hours, about 24-72 hours, about 48-72 hours, 1-20 days, 1-15 days, 1-10 days, 1-5 days, 5-20 days, 5-15 days, 5-10 days, 1-2 days, 2-3 days, 1-3 days, 2-4 days, 2-5 days, 2-8 days, 2-10 days, 4-10 days, 4-8 days, 6-8 days, 8-10 days, 7-9 days, 7-11 days, 7-13 days, 7-15 days, 10-12 days, 10-14 days, 12-14 days, 14-16 days, 14-18 days, 16-18 days or 18-20 days. According to a specific embodiment, the anti-third party cells are cultured in the presence of IL-21, IL-15 and IL-7 in an antigen free environment for about 7-11 days (e.g. 8 days).

This step is typically carried out in the presence of IL-21 at a concentration of about 0.001-3000 ng/ml, 0.001-1000 ng/ml, 0.01-1000 ng/ml, 0.1-1000 ng/ml, 1-1000 ng/ml, 10-1000 ng/ml, 10-500 ng/ml, 10-300 ng/ml, 10-100 ng/ml, 100-1000 ng/ml, 1-100 ng/ml, 1-50 ng/ml, 1-30 ng/ml, 10-50 ng/ml, 10-30 ng/ml, 10-20 ng/ml, 20-30 ng/ml, 20-50 ng/ml, 30-50 ng/ml, 30-100 ng/ml, 1-10 ng/ml, 0.1-10 ng/ml, 0.1-100 ng/ml, 1 ng/ml-100 ng/ml IL-21. According to a specific embodiment, the concentration of IL-21 is 10-50 ng/ml (e.g. 30 ng/ml).

This step is further carried out in the presence of IL-15 at a concentration of about 0.001-3000 ng/ml, 0.001-1000 ng/ml, 0.01-1000 ng/ml, 0.05-1000 ng/ml, 0.1-1000 ng/ml, 0.5-1000 ng/ml, 0.05-500 ng/ml, 0.5-500 ng/ml, 0.1-100 ng/ml, 0.1-10 ng/ml, 0.5-100 ng/ml, 1-100 ng/ml, 5-100 ng/ml, 1-50 ng/ml, 5-50 ng/ml, 1-10 ng/ml, 5-10 ng/ml, 1-5 ng/ml, 2-3 ng/ml, 2-5 ng/ml, 2-7 ng/ml, 3-5 ng/ml, 3-7 ng/ml, 4-5 ng/ml, 5-6 ng/ml, 5-7 ng/ml, 1-8 ng/ml, 10-100 ng/ml, 10-1000 ng/ml, 100-1000 ng/ml. According to a specific embodiment the concentration of IL-15 is 1-10 ng/ml (e.g. 5 ng/ml).

This step is further carried out in the presence of IL-7 at a concentration of about 0.001-3000 ng/ml, 0.001-1000 ng/ml, 0.01-1000 ng/ml, 0.05-1000 ng/ml, 0.1-1000 ng/ml, 0.5-1000 ng/ml, 0.05-500 ng/ml, 0.5-500 ng/ml, 0.1-100 ng/ml, 0.1-10 ng/ml, 0.5-100 ng/ml, 1-100 ng/ml, 5-100 ng/ml, 1-50 ng/ml, 5-50 ng/ml, 1-10 ng/ml, 5-10 ng/ml, 1-5 ng/ml, 2-3 ng/ml, 2-5 ng/ml, 2-7 ng/ml, 3-5 ng/ml, 3-7 ng/ml, 4-5 ng/ml, 5-6 ng/ml, 5-7 ng/ml, 1-8 ng/ml, 10-100 ng/ml, 10-1000 ng/ml, 100-1000 ng/ml. According to a specific embodiment the concentration of IL-7 is 1-10 ng/ml (5 ng/ml).

The present inventors have collected through laborious experimentation and screening a number of criteria which may be harnessed towards to improving the proliferation of anti-third party cells comprising a central memory T-lymphocyte (Tcm) phenotype being devoid of graft versus host (GVH) reactive cells and/or being enhanced for anti-disease (e.g. GVL) reactive cells.

According to one embodiment, the PBMCs are depleted of non-adherent cells prior to contacting with a third party antigen or antigens in the presence of IL-21.

According to one embodiment, the PBMCs are depleted of CD4+ and/or CD56+ cells prior to contacting with a third party antigen or antigens in the presence of IL-21.

According to one embodiment, the PBMCs are selected for CD45RA+ cells prior to contacting with a third party antigen or antigens in the presence of IL-21.

Depletion of $CD4^+$ and/or CD56+ cells may be carried out using any method known in the art, such as by affinity based purification (e.g. such as by the use of MACS beads, FACS sorter and/or capture ELISA labeling). Such a step may be beneficial in order to increase the purity of the $CD8^+$ cells within the culture (i.e. eliminate other lymphocytes within the cell culture e.g. T $CD4^+$ cells or NK cells) or in order to increase the number of $CD8^+$ T cells.

According to one embodiment, the PBMCs comprise non-adherent cells.

According to one embodiment, the PBMCs comprise CD8+ T cells.

According to one embodiment, the PBMCs comprise naïve CD8+ T cells.

Selection of naïve CD8+ T cells may be effected by selection of cells expressing CD45RA+ and/or cells expressing CD45RO– and may be carried out using any method known in the art, such as by affinity based purification (e.g. such as by the use of MACS beads, FACS sorter and/or capture ELISA labeling).

According to one embodiment, the PBMCs comprise CD45RA+ cells.

An additional step which may be carried out in accordance with the present teachings include culturing the PBMCs cells with a third party antigen or antigens in the presence of IL-21, IL-15 and IL-7 prior to removing the third party antigen or antigens from the cell culture (i.e. prior to generating an antigen free environment). This step is typically carried out for about 12-24 hours, about 12-36 hours, about 12-72 hours, 24-48 hours, 24-36 hours, about 24-72 hours, about 48-72 hours, 1-2 days, 2-3 days, 1-3 days, 2-4 days, 1-5 days or 2-5 days, and is effected at the same doses of IL-21, IL-15 and IL-7 indicated above. According to a specific embodiment, culturing the PBMCs cells with a third party antigen or antigens in the presence of IL-21, IL-15 and IL-7 is carried out for 12 hours to 4 days (e.g. 1-2 days).

Additionally or alternatively, an additional two step process which allows selection and isolation of activated cells may be carried out. Such a selection step aids in removal of potential host reactive T cells in situations where the PBMCs are non-syngeneic with respect to the subject (as described in further detail below).

Thus, isolating activated cells may be carried out in a two stage approach. In the first stage activated cells are selected before culturing the cells in the presence of IL-15 and IL-7. This first stage is typically carried out after the initial contacting of the PBMC with a third party antigen or antigens in the presence of IL-21. This selection process picks only those cells which were activated by the third party antigen (e.g. express activation markers as described below) and is typically affected about 12-24 hours, about 24-36 hours, about 12-36 hours, about 36-48 hours, about 12-48 hours, about 48-60 hours, about 12-60 hours, about 60-72 hours, about 12-72 hours, about 72-84 hours, about 12-84 hours, about 84-96 hours, about 12-96 hours, after the initial contacting of the PBMC with a third party antigen or antigens. According to a specific embodiment, the selection process is effected about 12-24 hours (e.g. 14 hours) after the initial contacting of the PBMC with a third party antigen or antigens.

Isolating activated cells may be effected by affinity based purification (e.g. such as by the use of MACS beads, FACS sorter and/or capture ELISA labeling) and may be effected towards any activation markers including cell surface markers such as, but not limited to, CD69, CD44, CD25, CFSE, CD137 or non-cell surface markers such as, but not limited to, IFN-γ and IL-2. Isolating activated cells may also be effected by morphology based purification (e.g. isolating large cells) using any method known in the art (e.g. by FACS). Typically, the activated cells are also selected for expression of CD8+ cells. Furthermore, any combination of the above methods may be utilized to efficiently isolate activated cells.

According to an embodiment of the present invention, selecting for activated cells is effected by selection of CD137+ and/or CD25+ cells.

The second stage of isolation of activated cells is typically carried out at the end of culturing (i.e. after culturing in an antigen free environment with IL-21, IL-15 and IL-7). This stage depletes alloreactive cells by depletion of those cells which were activated following contacting of the central memory T-lymphocyte (Tcm) with irradiated host antigen presenting cells (APCs e.g. dendritic cells). As mentioned above, isolating activated cells may be effected by affinity based purification (e.g. such as by the use of MACS beads, FACS sorter and/or capture ELISA labeling) and may be effected towards any activation markers including cell surface markers such as, but not limited to, CD69, CD44, CD25, CFSE, CD137 or non-cell surface markers such as, but not limited to, IFN-γ and IL-2.

According to an embodiment of the present invention, depleting the alloreactive cells is effected by depletion of CD137+ and/or CD25+ cells.

Following are a number of non-limiting examples of protocols which can be used according to some embodiments of the invention.

According to one embodiment of the invention, there is provided a method of generating an isolated population of cells comprising anti-third party cells having a central memory T-lymphocyte (Tcm) phenotype, the cells being tolerance-inducing cells and/or endowed with anti-disease activity (e.g. graft-versus-leukemia (GVL) activity), and capable of homing to the lymph nodes following transplantation, the method comprising: (a) treating non-adherent peripheral blood mononuclear cells (PBMC) with an agent capable of depleting CD4+ and/or CD56+ cells so as to obtain CD8+ T cells; (b) contacting the CD8+ T cells with third party dendritic cells in the presence of IL-21 for 12 hours to 5 days so as to allow enrichment of antigen reactive cells; (c) culturing the cells resulting from step (b) with the third party dendritic cells in the presence of IL-21, IL-15 and IL-7 for 12 hours to 3 days; and (d) culturing the cells resulting from step (c) in the presence of IL-21, IL-15 and IL-7 in an antigen free environment for 5-20 days so as to allow proliferation of cells comprising the central memory T-lymphocyte (Tcm) phenotype.

The above describe protocol is typically used for no-syngeneic transplantation and therefore the PBMC used are typically allogeneic with respect to a subject (e.g. from an allogeneic donor).

According to one embodiment of the invention, there is provided a method of generating an isolated population of cells comprising anti-third party cells having a central memory T-lymphocyte (Tcm) phenotype, the cells being endowed with anti-disease activity (e.g. anti-tumor cell activity), and capable of homing to the lymph nodes following transplantation, the method comprising: (a) treating non-adherent peripheral blood mononuclear cells (PBMC) with an agent capable of depleting CD4+ and/or CD56+ cells so as to obtain CD8+ T cells; (b) contacting the CD8+ T cells with non-syngeneic dendritic cells in the presence of IL-21 for 12 hours to 5 days so as to allow enrichment of antigen reactive cells; (c) culturing the cells resulting from step (b) with the non-syngeneic dendritic cells in the presence of IL-21, IL-15 and IL-7 for 12 hours to 3 days; and (d) culturing the cells resulting from step (c) in the presence of IL-21, IL-15 and IL-7 in an antigen free environment for 5-20 days so as to allow proliferation of cells comprising the central memory T-lymphocyte (Tcm) phenotype.

The above describe protocol is typically used for syngeneic transplantation and therefore the PBMC used are typically autologous with respect to a subject (e.g. from the subject).

Thus, as mentioned, the PBMC may be syngeneic or non-syngeneic with respect to a subject.

According to some embodiments of the invention, the non-syngeneic PBMCs of the present invention may be allogeneic or xenogeneic with respect to the subject (explained in further detail hereinbelow).

The source of the PBMCs will be determined with respect to the intended use of the cells (see further details hereinbelow) and is well within the capability of one skilled in the art, especially in light of the detailed disclosure provided herein.

The use of tolerance inducing cells is especially beneficial in situations in which there is a need to eliminate graft rejection and overcome graft versus host disease (GVHD), such as in transplantation of allogeneic or xenogeneic cells or tissues.

Thus, according to another aspect of the present invention, there is provided a method of treating a subject in need of a cell or tissue transplantation, the method comprising transplanting a cell or organ transplant into the subject and administering to the subject a therapeutically effective amount of the isolated population of cells.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

As used herein, the term "subject" or "subject in need thereof" refers to a mammal, preferably a human being, male or female at any age that is in need of a cell or tissue transplantation or suffers from a disease which may be treated with the Tcm cells. Typically the subject is in need of cell or tissue transplantation (also referred to herein as recipient) due to a disorder or a pathological or undesired condition, state, or syndrome, or a physical, morphological or physiological abnormality which is amenable to treatment via cell or tissue transplantation. Examples of such disorders are provided further below.

As used herein, the phrase "cell or tissue transplantation" refers to a bodily cell (e.g. a single cell or a group of cells) or tissue (e.g. solid tissues/organs or soft tissues, which may be transplanted in full or in part). Exemplary tissues or organs which may be transplanted according to the present teachings include, but are not limited to, liver, pancreas, spleen, kidney, heart, lung, skin, intestine and lymphoid/hematopoietic tissues (e.g. lymph node, Peyer's patches thymus or bone marrow). Exemplary cells which may be transplanted according to the present teachings include, but are not limited to, immature hematopoietic cells including stem cells. Furthermore, the present invention also contemplates transplantation of whole organs, such as for example, kidney, heart, liver or skin.

Depending on the application, the method may be effected using a cell or tissue which is syngeneic or non-syngeneic with the subject.

According to an embodiment of the present invention, both the subject and the donor are humans.

Depending on the application and available sources, the cells or tissues of the present invention may be obtained from a prenatal organism, postnatal organism, an adult or a cadaver donor. Moreover, depending on the application needed the cells or tissues may be naïve or genetically modified. Such determinations are well within the ability of one of ordinary skill in the art.

Any method known in the art may be employed to obtain a cell or tissue (e.g. for transplantation).

Transplanting the cell or tissue into the subject may be effected in numerous ways, depending on various parameters, such as, for example, the cell or tissue type; the type, stage or severity of the recipient's disease (e.g. organ failure); the physical or physiological parameters specific to the subject; and/or the desired therapeutic outcome.

Transplanting a cell or tissue transplant of the present invention may be effected by transplanting the cell or tissue transplant into any one of various anatomical locations, depending on the application. The cell or tissue transplant may be transplanted into a homotopic anatomical location (a normal anatomical location for the transplant), or into an ectopic anatomical location (an abnormal anatomical location for the transplant). Depending on the application, the cell or tissue transplant may be advantageously implanted under the renal capsule, or into the kidney, the testicular fat, the sub cutis, the omentum, the portal vein, the liver, the spleen, the heart cavity, the heart, the chest cavity, the lung, the skin, the pancreas and/or the intra abdominal space.

For example, a liver tissue according to the present teachings may be transplanted into the liver, the portal vein, the renal capsule, the sub-cutis, the omentum, the spleen, and the intra-abdominal space. Transplantation of a liver into various anatomical locations such as these is commonly practiced in the art to treat diseases amenable to treatment via hepatic transplantation (e.g. hepatic failure). Similarly, transplanting a pancreatic tissue according to the present invention may be advantageously effected by transplanting the tissue into the portal vein, the liver, the pancreas, the testicular fat, the sub-cutis, the omentum, an intestinal loop (the subserosa of a U loop of the small intestine) and/or the intra-abdominal space. Transplantation of pancreatic tissue may be used to treat diseases amenable to treatment via pancreatic transplantation (e.g. diabetes). Likewise, transplantation of tissues such as a kidney, a heart, a lung or skin tissue may be carried out into any anatomical location described above for the purpose of treating recipients suffering from, for example, renal failure, heart failure, lung failure or skin damage (e. g., burns).

The method of the present invention may also be used, for example, for treating a recipient suffering from a disease requiring immature hematopoietic cell transplantation.

In the latter case, immature autologous, allogeneic or xenogeneic hematopoietic cells (including stem cells) which can be derived, for example, from bone marrow, mobilized peripheral blood (by for example leukapheresis), fetal liver, yolk sac and/or cord blood of the donor and which are preferably T-cell depleted CD34+ immature hematopoietic cells, can be transplanted to a recipient suffering from a disease. Such a disease includes, but is not limited to, leukemia such as acute lymphoblastic leukemia (ALL), acute nonlymphoblastic leukemia (ANLL), acute myelocytic leukemia (AML) or chronic myelocytic leukemia (CML), severe combined immunodeficiency syndromes (SCID), including adenosine deaminase (ADA), osteopetrosis, aplastic anemia, Gaucher's disease, thalassemia and other congenital or genetically-determined hematopoietic abnormalities.

It will be appreciated that the immature autologous, allogeneic or xenogeneic hematopoietic cells of the present invention may be transplanted into a recipient using any method known in the art for cell transplantation, such as but not limited to, cell infusion (e.g. I.V.) or via an intraperitoneal route.

Optionally, when transplanting a cell or tissue transplant of the present invention into a subject having a defective organ, it may be advantageous to first at least partially remove the failed organ from the subject so as to enable optimal development of the transplant, and structural/functional integration thereof with the anatomy/physiology of the subject.

According to one embodiment, the immature hematopoietic cells and the isolated population of cells are derived from the same donor.

According to one embodiment, the immature hematopoietic cells and the isolated population of cells are derived from the same subject.

The method of the present invention also envisions co-transplantation of several organs (e.g. heart and lung tissues) in case the subject may be beneficially effected by such a procedure.

According to one embodiment, the co-transplantation comprises transplantation of immature hematopoietic cells and a solid tissue/organ or a number of solid organs/tissues.

According to one embodiment, the immature hematopoietic cells and the solid organ or obtained from the same donor.

According to another embodiment, the immature hematopoietic cells and the solid organ/tissue or organs/tissue are obtained from different (non-syngeneic) donors.

According to one embodiment, the immature hematopoietic cells are transplanted prior to, concomitantly with, or following the transplantation of the solid organ.

According to an embodiment, hematopoietic chimerism is first induced in the subject by transplantation of immature hematopoietic cells in conjunction with the Tcm cells of the present invention, leading to tolerance of other tissues/organs transplanted from the same donor.

According to an embodiment, the Tcm cells of the present invention are used per se for reduction of rejection of transplanted tissues/organs organs transplanted from the same donor.

In a further embodiment, the cell or tissue transplant and the isolated population of cells are derived from the same donor.

In a further embodiment, the cell or tissue transplant is syngeneic with the subject and the isolated population of cells are non-syngeneic with the subject.

In a further embodiment, the cell or tissue transplant is syngeneic with the subject and the isolated population of cells are syngeneic with the subject.

Following transplantation of the cell or tissue transplant into the subject according to the present teachings, it is advisable, according to standard medical practice, to monitor the growth functionality and immuno-compatibility of the organ according to any one of various standard art techniques. For example, the functionality of a pancreatic tissue transplant may be monitored following transplantation by standard pancreas function tests (e.g. analysis of serum levels of insulin). Likewise, a liver tissue transplant may be monitored following transplantation by standard liver function tests (e.g. analysis of serum levels of albumin, total protein, ALT, AST, and bilirubin, and analysis of blood-clotting time). Structural development of the cells or tissues may be monitored via computerized tomography, or ultrasound imaging.

Depending on the transplantation context, in order to facilitate engraftment of the cell or tissue transplant, the method may further advantageously comprise conditioning the subject under sublethal, lethal or supralethal conditions prior to the transplanting.

As used herein, the terms "sublethal", "lethal", and "supralethal", when relating to conditioning of subjects of the present invention, refer to myelotoxic and/or lymphocytotoxic treatments which, when applied to a representative population of the subjects, respectively, are typically: non-lethal to essentially all members of the population; lethal to some but not all members of the population; or lethal to essentially all members of the population under normal conditions of sterility.

According to one embodiment, the conditioning step is effected by conditioning the subject under supralethal conditions, such as under myeloablative conditions.

Alternatively, the conditioning step may be effected by conditioning the subject under lethal or sublethal conditions, such as by conditioning the subject under myeloreductive conditions.

Examples of conditioning agents which may be used to condition the subject include, without limitation, irradiation, pharmacological agents, and tolerance-inducing cells (as described herein).

Examples of pharmacological agents include myelotoxic drugs, lymphocytotoxic drugs and immunosuppressant drugs.

Examples of myelotoxic drugs include, without limitation, busulfan, dimethyl mileran, melphalan and thiotepa.

The method may further advantageously comprise conditioning the subject with an immunosuppressive regimen prior to, concomitantly with, or following transplantation of the cell or tissue transplant.

Examples of suitable types of immunosuppressive regimens include administration of immunosuppressive drugs, tolerance inducing cell populations (as described in detail hereinbelow), and/or immunosuppressive irradiation.

Ample guidance for selecting and administering suitable immunosuppressive regimens for transplantation is provided in the literature of the art (for example, refer to: Kirkpatrick C H. and Rowlands D T Jr., 1992. JAMA. 268, 2952; Higgins R M. et al., 1996. Lancet 348, 1208; Suthanthiran M. and Strom T B., 1996. New Engl. J. Med. 331, 365; Midthun D E. et al., 1997. Mayo Clin Proc. 72, 175; Morrison V A. et al., 1994. Am J Med. 97, 14; Hanto D W., 1995. Annu Rev Med. 46, 381; Senderowicz A M. et al., 1997. Ann Intern Med. 126, 882; Vincenti F. et al., 1998. New Engl. J. Med. 338, 161; Dantal J. et al. 1998. Lancet 351, 623).

Preferably, the immunosuppressive regimen consists of administering at least one immunosuppressant agent to the subject.

Examples of immunosuppressive agents include, but are not limited to, methotrexate, cyclophosphamide, cyclosporine, cyclosporin A, chloroquine, hydroxychloroquine, sulfasalazine (sulphasalazopyrine), gold salts, D-penicillamine, leflunomide, azathioprine, anakinra, infliximab (REMICADE), etanercept, TNF.alpha. blockers, a biological agent that targets an inflammatory cytokine, and Non-Steroidal Anti-Inflammatory Drug (NSAIDs). Examples of NSAIDs include, but are not limited to acetyl salicylic acid, choline magnesium salicylate, diflunisal, magnesium salicylate, salsalate, sodium salicylate, diclofenac, etodolac, fenoprofen, flurbiprofen, indomethacin, ketoprofen, ketorolac, meclofenamate, naproxen, nabumetone, phenylbutazone, piroxicam, sulindac, tolmetin, acetaminophen, ibuprofen, Cox-2 inhibitors, tramadol, rapamycin (sirolimus) and rapamycin analogs (such as CCI-779, RAD001, AP23573). These agents may be administered individually or in combination.

Regardless of the transplant type, to avoid graft rejection and graft versus host disease, the method of the present invention utilizes the novel anti third party Tcm cells (as described in detail hereinabove).

According to the method of the present invention, these anti third party Tcm cells are administered either concomitantly with, prior to, or following the transplantation of the cell or tissue transplant.

The anti third party Tcm cells may be administered via any method known in the art for cell transplantation, such as but not limited to, cell infusion (e.g. I.V.) or via an intraperitoneal route.

Without being bound to theory, a therapeutically effective amount is an amount of anti-third party Tcm cells efficient for tolerization, anti-tumor effect and/or immune reconstitution without inducing GVHD. Since the Tcm cells of the present invention home to the lymph nodes following transplantation, lower amounts of cells (compared to the dose of cells previously used, see for example WO 2001/049243) may be needed to achieve the beneficial effect/s of the cells (e.g. tolerization, anti-tumor effect and/or immune reconstitution). It will be appreciated that lower levels of immunosuppressive drugs may be needed in conjunction with the Tcm cells of the present invention (such as exclusion of rapamycin from the therapeutic protocol).

Determination of the therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

For example, in case of tissue transplantation the number of anti-third party Tcm cells infused to a recipient should be more than $1\times10^4$/Kg body weight. The number of anti-third party Tcm cells infused to a recipient should typically be in the range of $1\times10^3$/Kg body weight to $1\times10^4$/Kg body weight, range of $1\times10^4$/Kg body weight to $1\times10^5$/Kg body weight, range of $1\times10^4$/Kg body weight to $1\times10^6$/Kg body weight, range of $1\times10^4$/Kg body weight to $1\times10^7$/Kg body weight, range of $1\times10^4$/Kg body weight to $1\times10^8$/Kg body weight, range of $1\times10^3$/Kg body weight to $1\times10^5$/Kg body weight, range of $1\times10^4$/Kg body weight to $1\times10^6$/Kg body weight, range of $1\times10^6$/Kg body weight to $1\times10^7$/Kg body weight, range of $1\times10^5$/Kg body weight to $1\times10^7$/Kg body weight, range of $1\times10^6$/Kg body weight to $1\times10^8$/Kg body weight. According to a specific embodiment, the number of anti-third party Tcm cells infused to a recipient should be in the range of $1\times10^5$/Kg body weight to $1\times10^7$/Kg body weight.

Thus, the novel anti-third party Tcm cells of the present invention may be used as adjuvant therapy for a cell or tissue transplant (as described hereinabove). In addition the novel Tcm cells of the present invention are also endowed with anti-disease activity (e.g. anti-tumor cell activity, as described in further detail hereinabove) and thus may be used per se for disease treatment.

According to a specific embodiment, in order to obtain a graft versus diseased cell activity (e.g. anti-tumor effect such as anti-leukemia treatment), syngeneic cells as well as non-syngeneic cells may be used.

Thus, the method of the present invention may be applied to treat any disease such as, but not limited to, a malignant disease, a disease associated with transplantation of a graft, an infectious disease such as a viral disease or a bacterial disease, an inflammatory disease and/or an autoimmune disease.

Diseases which may be treated using the methods of the present invention include, but are not limited to, malignant diseases such as leukemia [e.g., acute lymphatic, acute lymphoblastic, acute lymphoblastic pre-B cell, acute lymphoblastic T cell leukemia, acute-megakaryoblastic, monocytic, acute myelogenous, acute myeloid, acute myeloid with eosinophilia, B cell, basophilic, chronic myeloid, chronic, B cell, eosinophilic, Friend, granulocytic or myelocytic, hairy cell, lymphocytic, megakaryoblastic, monocytic, monocytic-macrophage, myeloblastic, myeloid, myelomonocytic, plasma cell, pre-B cell, promyelocytic, subacute, T cell, lymphoid neoplasm, predisposition to myeloid malignancy, acute nonlymphocytic leukemia, T-cell acute lymphocytic leukemia (T-ALL) and B-cell chronic lymphocytic leukemia (B-CLL)], lymphoma (e.g., Hodgkin's disease, non-Hodgkin's lymphoma, B cell, Burkitt, cutaneous T cell, histiocytic, lymphoblastic, T cell, thymic), carcinoma, blastoma and sarcoma; diseases associated with transplantation of a graft (e.g. graft rejection, chronic graft rejection, subacute graft rejection, hyper-acute graft rejection, acute graft rejection and graft versus host disease); infectious diseases including, but are not limited to, chronic infectious diseases, subacute infectious diseases, acute infectious diseases, viral diseases (e.g. EBV, CMV, HIV), bacterial diseases, protozoan diseases, parasitic diseases, fungal diseases, *mycoplasma* diseases and prion diseases; inflammatory diseases (e.g. chronic inflammatory diseases and acute inflammatory diseases); and autoimmune diseases (e.g. cardiovascular diseases, rheumatoid diseases, glandular diseases, gastrointestinal diseases, cutaneous diseases, hepatic diseases, neurological diseases, muscular diseases, nephric diseases, diseases related to reproduction, connective tissue diseases and systemic diseases).

Thus, the method of the present invention can furthermore be advantageously applied towards treating a disease in a subject while concomitantly facilitating engraftment of a transplant of cells or tissues syngeneic with the anti-third party Tcm cells (e.g. in situations where the cell or tissue transplant and the anti-third party cells are derived from the same donor).

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

General Materials and Experimental Procedures

Peripheral Blood Mononuclear Cells (PBMC)

PBMC were isolated from whole blood of patients and from healthy volunteers by Ficoll density gradient centrifugation. When indicated the cells were typed for Class I HLA by serological methods as previously described [Manual of Tissue Typing Techniques. Washington D.C., National Institute of Allergy and Infectious Diseases, NIH DHEW Publication 76-545, 1976, p 22].

Tumor Cell Lines

H.My2 C1R HLA A2 K66A transfectant cells and H.My2 C1R HLA A2 w.t. transfectant B cell line were used.

C1R, a human B-cell lymphoblastoid line lacking surface HLA A and B antigens, derived from Hmy.2 B-LCL by gamma irradiation followed by selection for Class I monoclonal antibodies and complement as previously described [Storkus W J, et al. Proc. Natl. Acad. Sci. USA (1989) 86: 2361-2364] was used.

C1R-neo, a stable transfectant cell line established in 1987 by electroporation of the C1R cell line with a modified neomycin drug-resistant eukaryotic vector, pSP65-Neo (the vector did not carry an insert), as previously described [Grumet F C, et al. Hum. Immunol. (1994) 40: 228-234] was used.

Dendritic Cell Generation

Monocytes were isolated by plastic adherence and cultured in 6-well plates using 3 ml of Cellgro DC medium supplemented with 1% human serum and penicillin/streptomycin plus GM-CSF (800 IU/ml) and IL-4 (20 ng/ml) (Peprotech, Hamburg, Germany). After 48 h of culture, 1.5 ml of medium was added (+GM-CSF at 1600 IU/ml and IL4 at 20 ng/ml). 24 h later, non-adherent cells were harvested, and large cells (mostly immature DC) were counted, resuspended in fresh medium containing GM-CSF 800 IU/ml, IL-4 20 ng/ml, LPS from E. coli 055:B5 at 10 ng/ml (Sigma, Deisenhofen, Germany) and IFNγ (Peprotech, 100 IU/ml), and plated at approximately $10^6$ DC per well in 2 ml and incubated overnight. The next day, non-adherent cells were discarded, and adherent DC were gently removed using cold PBS/1% HS after incubation on ice for 20 minutes. Large cells consisting of mature DC were counted. The cells were irradiated with 30 Gy to avoid outgrowth of few potentially contaminating NK– or memory T-cells and were then used for T-cell stimulation.

Isolation of Naïve CD8 T-Cells from PBMC

Naïve CD8 T cells were isolated by initial negative selection using a CD8 negative selection kit (Miltenyi, Bergisch Gladbach, Germany) according to the manufacturer's instructions. Antigen-experienced CD8+ T-cells were then depleted using CD45RO– beads and on LD column.

Generation of Anti-3rd Party Central Memory Human CD8 T-Cells

Naïve CD8 T cells were isolated and resuspended in T-cell medium supplemented with IL-21 (Peprotech, 30 ng/ml). Irradiated DCs were added at a 1:4 DC:T-cell ratio with $4\times10^5$ T-cells per well of a 48-well plate. Total volume of each well was 500 µl.

72 h after initiation of the culture, 500 µl T-cell medium with IL-7 and IL-15 (Peprotech, 5 ng/ml final concentrations) were added and cells were subsequently fed every 2-3 days as outline in the results section.

GVL Assay

H.My C1R ("Neo") and H.My C1R HLA A2 K66A mutant transfectant ("K66A") B lymphoblast line cells were obtained by Ficoll density gradient centrifugation and were labeled with 0.15 µg/ml CalceinAM (Molecular Probes, Inc, Eugene, Oreg.), a vital dye that is released upon cell death, according to manufacturer's instructions. Next, $2\times10^5$ Calcein labeled B lymphoblast line cells were incubated with or without anti-$3^{rd}$ party Tcm for 22 hours at a 1 to 5 ratio in favor of anti-$3^{rd}$ party Tcms in 24 well plates. Prior to the co culture anti-$3^{rd}$ party Tcm were enriched for CD8+ T cells by a negative selection kit (Miltenyi, Bergisch Gladbach, Germany). No exogenous cytokines were added to the MLR. Cells were recovered and analyzed for survival by measuring the number of surviving Calcein stained B lymphoblast line cells by FACS. For detection of apoptosis by AnnexinV+ samples were incubated with 5 µl AnnexinV-APC (BD) for 15 minutes at room temperature. Subsequently, unbound AnnexinV was washed out, and samples were analyzed by FACS. To obtain absolute values of cells, samples were suspended in constant volume and flow cytometric counts for each sample were obtained during a constant, predetermined period of time and were compared with flow cytometric counts obtained with fixed volume and fixed numbers of input cells. Survival rate are presented relative to the survival of B lymphoblast line cells alone.

The percentage of B lymphoblast line cells killing was calculated by the following formula:

$$\left(1 - \frac{\text{The number of live } B \text{ lymphoblast line cells in the assessed well}}{\text{The number of live } B \text{ lymphoblast line cells in the control well}}\right) \times 100$$

The percentage of B lymphoblast line cells undergoing specific apoptosis was calculated by the following formula: =(% Calcein+AnnexinV+ B lymphoblast line cells in the assessed well)−(% Calcein+AnnexinV+ B lymphoblast line cells in the control well).

A Two Stage Magnetic Sorting Approach for Depletion of Alloreactivity, Based on the CD137 Activation Marker Naïve CD8 T cells were stimulated with irradiated allogeneic 3rd party DC at a ratio of 6:1 in the presence of IL-21 (Peprotech, 30 ng/ml). After 14 hours of activation, CD137+ cells were positively selected by magnetic sorting (Miltenyi, Bergisch Gladbach, Germany). CD137+ cells were then re-stimulated with irradiated allogeneic 3rd party DC at a ratio of 4:1 in the presence of IL-21 (Peprotech, 30 ng/ml) until day 3. Thereafter, the cells were expanded with 5 ng/ml IL-7 and 5 ng/ml IL-15 (Peprotech) until day 10. On day 10, cells were divided into two test groups. In the first group cells continued to be expanded with IL-7 and IL-15 until day 14, while cells in the second test group were activated with irradiated host PBMC in the presence of IL-7 and IL-15 (at a ratio of 1 to 2). After 24 h, CD137+ cells were depleted by magnetic sorting. The CD137 depleted cells were re plated with IL-7 and IL-15 and cultured until day 14 ("Anti $3^{rd}$ CD137+ and Anti host CD137−"). On day 14, anti 3rd party and anti-host alloreactivity was evaluated by CFSE assay against 3rd party or irradiated host PBMCs. For the CFSE assay, $1\times10^6$ CFSE+ responders were incubated with or without $2\times10^6$ irradiated (20 gy) PBMC stimulators for 84 h in the presence of IL-7. After 84 h, cells were recovered and analyzed for cell division by measuring the number of CFSE low stained CD8 T cells (CD3+CD8+CD56−) by FACS. To obtain absolute values of cells, samples were suspended in a constant volume and flow cytometric counts for each sample were obtained during a constant, predetermined period. The number of specific dividing cells=(Number of dividing cell with APC)−(Number of dividing cell without APC). Negative values signify that the number of dividing cells in response to activation with host PBMC was even lower that the number of dividing cell without any activation.

Example 1

Generation and Optimization of Human Anti-Third Party T Central Memory (Tcm) Cells In order to translate the mouse studies previously presented to clinical application, the procedure was optimized for generating human anti-3rd party cytotoxic T lymphocytes (CTLs). To that end, different parameters were evaluated including different reagents for the isolation of CD8 responder cells, the composition of the stimulators and the cytokine milieu.

Potentially, as found in the previously presented mouse model, treatment with central memory T cells (Tcm) could be valuable either in the context of autologous [Lask A et al., Blood (ASH Annual Meeting Abstracts), (2010) 116: 424] or in allogeneic bone marrow transplant (BMT) [Ophir E et al., Blood. (2010) 115(10): 2095-104; Ophir E., 37th EBMT annual meeting, Apr. 3-6, 2011, Paris, France. Oral Presentation Abstract Nr: 662].

In the human autologous setting (FIG. 1A) anti-$3^{rd}$ party Tcm can be administrated together with autologous BMT. The patient's own CD8+ T cells are isolated and stimulated against allogeneic dendritic cells from an allogeneic donor.

In the human allogeneic setting (FIG. 1B), anti-$3^{rd}$ party Tcm can be transplanted together with allogeneic T depleted BM cells. Naïve CD8+ T cells originating from the allogeneic BM donor serve as responders and $3^{rd}$ party donor dendritic cells are used as stimulators to enable the generation of host non-reactive Tcm. In order to avoid GVHD, the $3^{rd}$ party donor is selected so as to insure that none of his HLA class I alleles are shared with the HLA class I alleles of the host.

While in both mouse and humans, the basic envisioned protocol similarly comprised CD8 T cell isolation followed by stimulation against $3^{rd}$ party cells (FIGS. 1A-1B and 2A-2B), several other parameters had to be modified in the human protocol, as outlined in Table 1, below.

Considering that autologous Tcm are free of GVHD risk, the optimization of the production protocol largely concentrated on attaining effective expansion of anti-$3^{rd}$ party CD8 T cells with central memory phenotype.

Figure 3A:
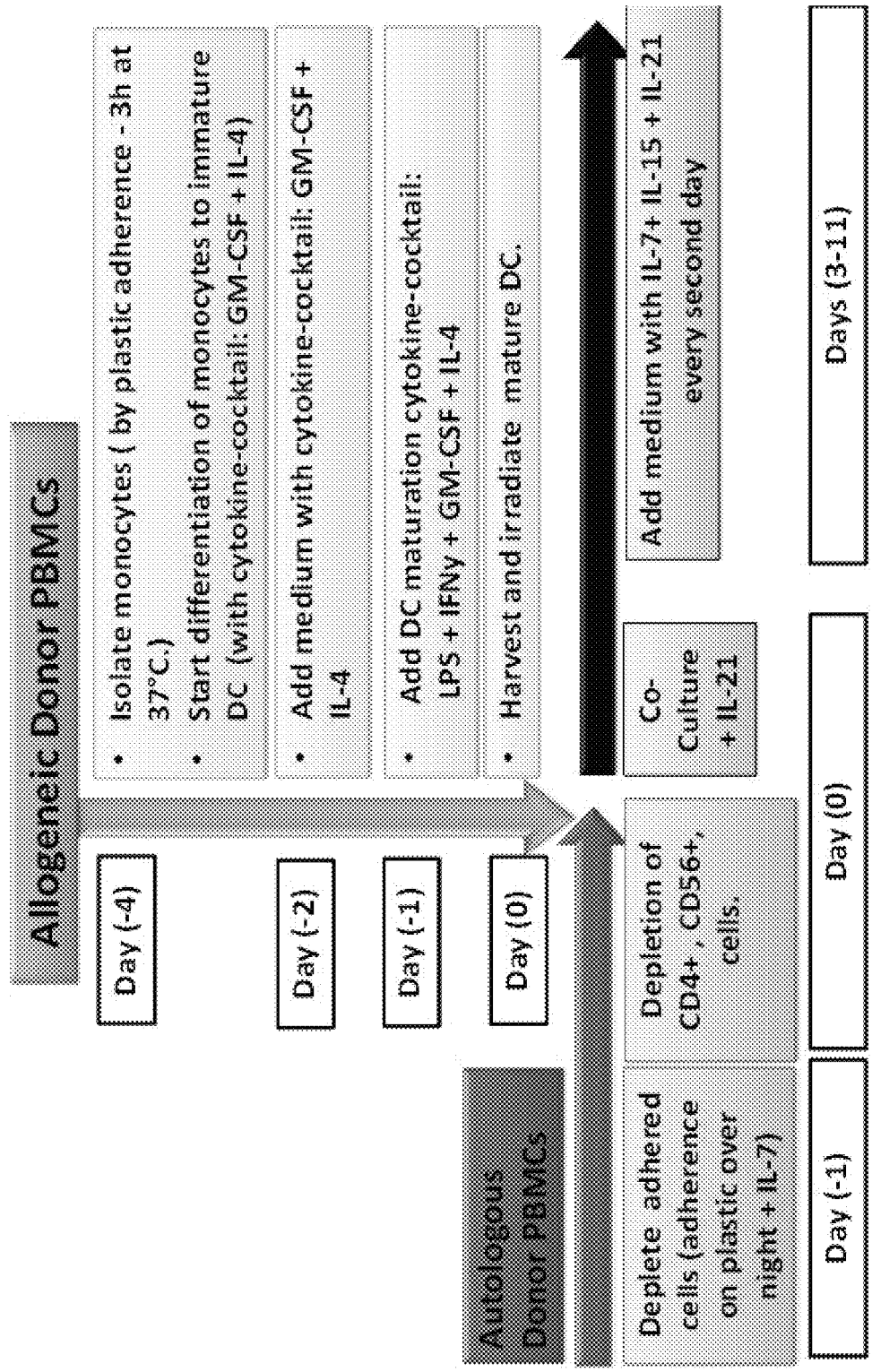

As can be seen in FIG. 3A, a new protocol was developed based on three major steps: a) Selection of CD8 T cells from PBMC; b) Stimulation against allogeneic dendritic cells (DC) for 3 days in the presence of IL-21; and c) Expansion in an antigen free environment with IL-7, IL-15 and IL-21 for an additional 8 days.

Figure 3B:
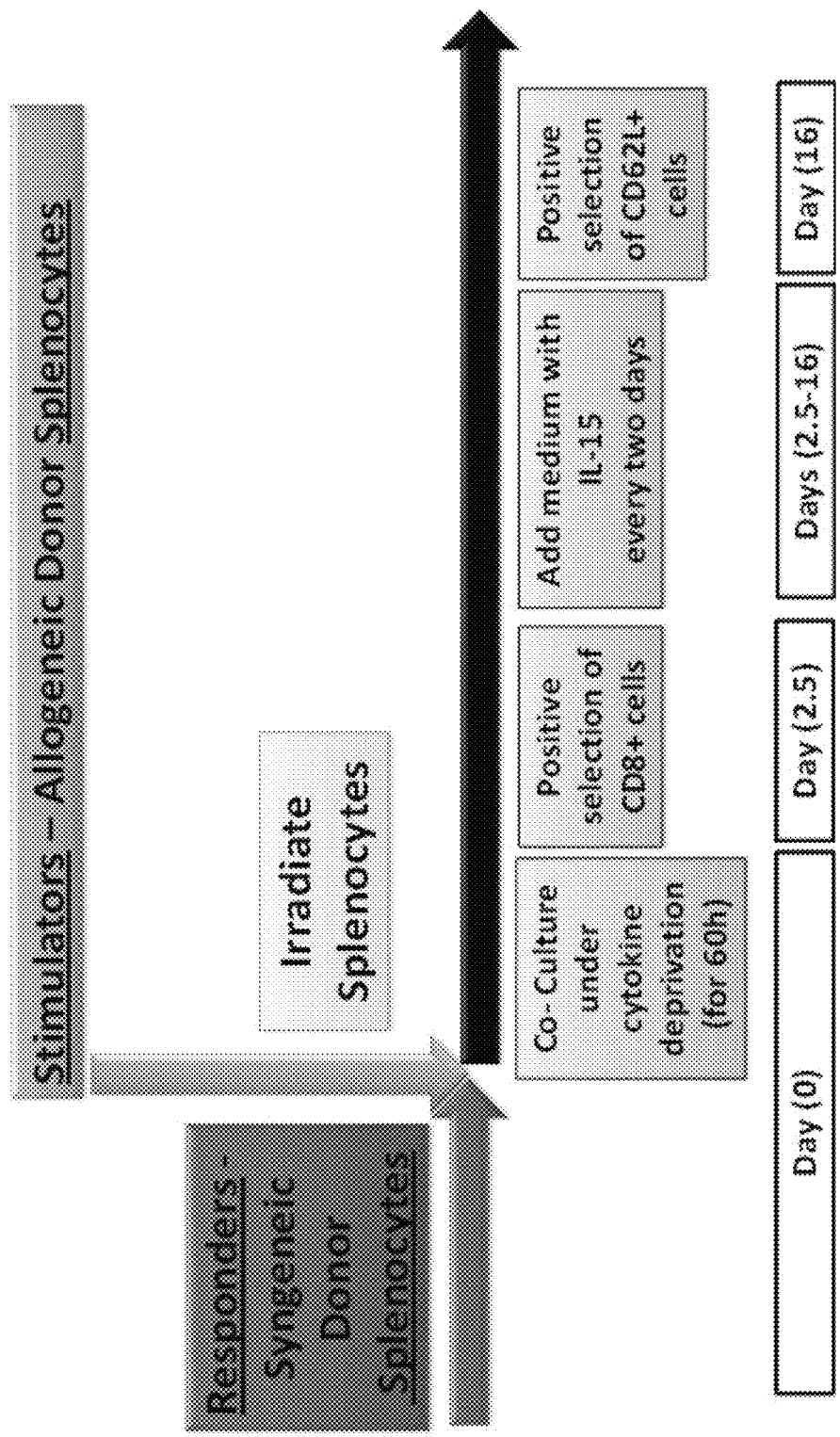

Thus, in this newly developed protocol various parameters differ from that used for the generation of mouse Tcm (Table 1 and FIGS. 3A-3B). The major differences concern the tissue of origin for the responders and stimulators (PBMC vs. splenocytes), the stimulators (dendritic cells vs. splenocytes), as well as the cytokine composition.

TABLE 1

Comparison of autologous human protocol versus the syngeneic mouse protocol for generation of Tcm

| Human | Mouse | Parameters | Major stages |
| --- | --- | --- | --- |
| Frozen PBMC YES | Fresh Splenocytes NO | Tissue of origin Depletion of adhered cells (Adherence on plastic overnight + IL-7) | Responders |
| YES | NO | Depletion of CD4+, CD56+ Cells | |
| CD8+ T cells | Whole Splenocytes | Final cell composition before co-culture with stimulators | |
| Frozen PBMC YES | Fresh Splenocytes NO | Tissue of origin Generation of monocyte derived mature dendritic cells | $3^{rd}$ party Stimulators |

TABLE 1-continued

| Dendritic Cells | Whole Splenocytes | Final cell composition before co-culture with responders | |
|---|---|---|---|
| CD8+ T cells→ Irradiated DCs | Splenocytes→ Irradiated Splenocytes | Cell composition | Co-Culture: (Priming) |
| 3 Days D0: IL-21 is added. Non adherent cells are transferred to a new plate | 2.5 Days No Cytokines! Ficoll, CD8+ positive selection and plating in a new flask. | Length of Co culture Cytokines Co culture is stopped by: | |
| IL-7, IL-15, IL-21 NO | IL-15 YES | Cytokines Positive selection of CD62L+ Cells at the end of culture | Antigen free Expansion |

Optimization of a GMP Grade Protocol for the Generation of Human Anti-$3^{rd}$ Party Tcm:

The initial attempts to develop a human protocol for the generation of anti-$3^{rd}$ party Tcm was based on a recent study by Wolff et al. [Wolff M et al., Cancer Immunol Immunother (2011) 60(2): 173-186], who described a procedure for the generation of human antigen specific CD8 T cells with a central memory phenotype.

The present approach was based on stimulation against antigen pulsed DC in the presence of IL-21 for 3 days and subsequent expansion in the presence of IL-7 and IL-15 for an additional 8 days.

In these initial experiments which resulted in an impressive expansion of anti-$3^{rd}$ party Tcm and subsequently served as a reference for further optimization, the following steps were used: a) CD8 T cell enrichment from PBMCs by depletion of non-CD8+ cells. (i.e., CD4+ T cells, γ/δ T cells, B cells, NK cells, dendritic cells, monocytes, granulocytes and erythroid cells); b) Enrichment of naïve cells by depletion of activated cells expressing CD45RO; and c) Stimulation of naïve CD8 T cells against allogeneic dendritic cells in the presence of IL-21 for 3 days followed by expansion in an antigen free environment with IL-7 and IL-15 for an additional 8 days.

The results of these initial reference experiments, shown in FIGS. 4A-4C, enabled evaluation of the role of different parameters in the protocol, by defining the impact of each parameter on the level of cell expansion and expression level of Tcm phenotype (as described in detail below).

The Role of Priming with 3rd Party DCs

Considering that autologous Tcm are free of GVHD risk by definition, the first parameter evaluated was the role of stimulation against a $3^{rd}$ party DC. This step was originally intended to reduce the risk for GVHD in the allogeneic setting, by selective expansion of anti-$3^{rd}$ party clones in the absence of stimulation of anti-host clones mediating GVHD.

As illustrated in FIGS. 5A-5C and 6A-6B, naïve CD8 T cells grown with IL-21 in the absence of allogeneic stimulation by dendritic cells, exhibited low proliferation level (2.7±1.1% of that exhibited by the reference control group), representing on day 7 approximately 0.4 fold expansion from day 0 (most cells died before day 10), and maintaining their naïve phenotype (CD45RO−CD62L+, small morphology) (Tcm level was only 10% from that of reference control group). A similar poor level of differentiation and expansion was found when the cells were maintained with IL-7 and IL-15 in the absence of allogeneic stimulation by dendritic cells; under these conditions, the cells maintained their naïve phenotype (Tcm level was only 7±1.6% from that of reference control group), though some proliferation was induced (12±3.2% of the control group value, representing on day 13 approximately 6 fold expansion from day 0). Thus, the role of allogeneic third party DC was very critical for induction of the Tcm phenotype and for robust cell expansion.

The Role of IL-21 in the Priming and Expansion Phases of Anti-3rd Party Tcm

Generally, both in mouse and human, conventional T cell expansion protocols the expansion phase is performed in antigen free environment. However, while in the mouse protocol, only IL-15 was added (FIG. 3B), in the human protocol described by Wolff et al. (Wolff et al. 2011, supra), cell expansion was performed in the presence of IL-7 and IL-15. Furthermore, considering that IL-21 was shown to be beneficial if added during the initial priming phase, the role of IL-21 was evaluated herein.

Interestingly, as shown in FIGS. 7A-7C and 8A-8B, while priming of naïve CD8 T cells by allogeneic DC in the presence or absence of IL-21 had only minor effect on cell composition (data not shown), priming in the absence of IL-21 hampered the acquisition of Tcm phenotype (CD45RO+CD62L+) (Only 69±18% of the Tcm level in the reference control group), and also resulted in reduced proliferation (76±23% of the expansion level in the reference control group) (FIGS. 8A-8B). Even in the single experiment out of four, in which expansion was not reduced (140% of reference control group) the Tcm phenotype was only 35% of the Tcm level in the reference control group, suggesting that priming in the presence of IL-21 is important for both expansion and induction of Tcm phenotype from the naïve CD8 T cell population.

Interestingly, continuous presence of IL-21 in both the priming phase (IL-21 alone) and in the expansion phase (together with IL-7 and IL-15) consistently improved induction of cells of the central memory phenotype (108±1.9% of the Tcm level in the reference control group) (FIGS. 7A-7C and 8A-8B). The impact of continuous IL-21 presence on cell expansion, although clearly leading to higher average increase (135±47% of the values found in the reference control group) was less consistent, leading in two out of three experiments to slightly reduced expansion (95% and 81% of reference values, respectively), while in the third experiment, exhibiting dramatically enhanced expansion (228%), indicating that adding IL-21 in both the priming and expansion phases might be desirable (FIGS. 8A-B).

Composition of the $3^{rd}$ Party Stimulator Cells

The results described above show that the sequential addition of IL-21, IL-7, and IL-15 must be accompanied by allogeneic stimulation by monocyte derived mature DC for successful induction of Tcm phenotype and for robust cell expansion.

To simplify the procedure, an experiment was carried out to evaluate whether the essential allogeneic stimulation could be delivered by irradiated PBMCs instead of monocyte derived mature DC that requires a 4 day preparation.

As can be seen in Table 2 below, at 7 days of culture, the efficiency of induction of Tcm phenotype by PBMC, as opposed to monocyte derived mature DC (md-mDC), stimulators was very similar, both when purified naïve CD8 T cells (92% vs. 92%, respectively) and when un-separated CD8 T cells served as responders (77% vs. 80%).

However, the PBMC stimulators were not able to elicit the same level of Tcm expansion compared to DCs using either naïve CD8 T cells (6.75 vs. 20.5, respectively) or un-separated CD8 T cells (1.8 vs. 16) as responders.

TABLE 2

The critical role of DCs as stimulators

| % Tcm (CD3+ CD8+ CD62L+ CD45RA−) | Fold expansion from day 0 (on day 7) | Group |
| --- | --- | --- |
| 92 | 20.5 | Naïve CD8 T cells → (md-mDC) |
| 92 | 6.75 | Naïve CD8 T cells → PBMC |
| 80 | 16 | Un-separated CD8 T cells → (md-mDC) |
| 77 | 1.8 | Un-separated CD8 T cells → PBMC |

MLR culture in which naïve CD8 T cells or unseparated CD8 T responders were stimulated against monocyte-derived mature DC (8:1 responder/DC ratio) or PBMC (1:1 responder/PBMC ratio), from the same allogeneic donor, in a medium containing IL-21 for 3 days. Thereafter, the cells were grown with IL-7 and IL-15 until day 7 without further activation. On day 7 of the culture, the different groups were evaluated for percentage of Tcm using FACS analysis and for cell numbers by trypan blue exclusion.

Thus, unlike the mouse protocol in which irradiated splenocytes were sufficient for inducing expansion, in the human protocol, allogeneic monocyte derived mature DC are crucial for good expansion of Tcm cells and cannot be replaced by allogeneic PBMC.

Defining the Optimal Responder/DC Ratio for the Induction of Tcm Phenotype and Cell Expansion.

To define the optimal responder/DC ratio, a MLR system was used, as described above, except that different responder/DC ratios were tested. As can be seen in FIGS. 9A-9B, when using $4 \times 10^5$ responders, an optimal acquisition of Tcm phenotype was attained upon addition of $50\text{-}100 \times 10^3$ DC, while expansion was optimal at the lowest DCs concentration. Further experiments at lower responder/DC ratios are examined.

Defining a Final Autologous Protocol Based Exclusively on GMP Grade Reagents.

Upon establishment of a satisfactory autologous protocol for the generation of anti-$3^{rd}$ party Tcm, an experiment was carried out to develop an equivalent procedure based solely on GMP grade reagents currently available commercially so as enable testing of this approach in human patients.

Depletion of Adherent Cells on Plastic Dishes.

Before optimizing the process of CD8 T cell selection, an experiment was carried out to attain a significant initial enrichment by removal of plastic adherent cells present in PBMC. This process not only increases the concentration of the desired CD8+ T cells but is also useful when processing cryopreserved human PBMC as opposed to fresh splenocytes used in the mouse model. This experiment revealed that overnight incubation with 10% human serum and IL-7 allowed the thawed cells to recover before being subjected to the magnetic enrichment process (data not shown).

Enrichment of Naïve CD8 T Cells

Next, the focus was on adapting the enrichment of naïve CD8 T cells to clinical grade reagents using as few antibodies as possible As shown in FIG. 10, representing a typical experiment, the desired population of CD8 T cells represents 21% of the cells on day 0 after depletion of adhered cells, while the other major "contaminating" subpopulations include CD4 T cells (61%), B cells (7%) and NK cells (7%). Thus, the CD4 cells represent the largest contamination, and were previously shown to compete with CD8 T cells; these cells therefore had to be removed. Likewise, it was important to remove NK cells that are known to expend in IL-15 cultures. In contrast, B cells tend to die under these culture conditions. Thus, potential depletion with anti-CD4 and anti-CD56 magnetic beads was initially evaluated with and without depletion of CD19+ B cells.

In addition, since in PBMC of patients with B cell malignancies, the levels of CD8 T cells are lower compared to healthy donors, a parallel evaluation was carried out examining the possibility of omitting the enrichment of naïve CD8 T cells by positive selection of CD45RA+ cells, as it further decreases the number of recovered CD8 T cells.

Thus, on day −1 donor PBMC were first depleted from adherent cells by overnight incubation in greiner-bio-one CELLSTAR tissue culture plates (Greiner Bio-One Ltd., Stonehouse UK), specifically designed to remove adherent myeloid cells and on day 0 non-adherent cells were divided to four experimental groups, each subjected to a different magnetic sorting protocol. On days 0, 7, 10 and 14 of culture, cells were evaluated for cell composition and Tcm phenotype by FACS analysis and for expansion by counting live cells based on trypan blue exclusion.

As can be seen in FIG. 10, minimal magnetic cell sorting using only anti-CD4 and anti-CD56 beads, decreased the percentage of CD4 T and NK cells from 61% and 7% to 12% and 1%, respectively, resulting in enrichment of CD8 T cells from 23% to 60%. However, this procedure was associated with enhancement of B cell levels from 7% to 24%. Adding anti-CD19 to the depletion cocktail completely depleted the B cells, resulting in improved enrichment of CD8 T cells (90%). Adding a second step of positive enrichment of naïve cells with anti-CD45RA increased the percent of naïve cells (CD45RO−CD45RA+, gated on CD3+CD8+) from 53% before magnetic sorting to 91% in both groups. However, this step did not markedly affect the final level of CD8 T cells, which increased from 60% to 66% when using anti-CD4 and anti-CD56, or from 90% to 94% when the negative selection step also included anti-CD19.

After the magnetic cell sorting, all four groups were primed with allogeneic dendritic cells in the presence of IL-21 for 3 days, and thereafter, the cells were expanded in an antigen free environment until day 14, in the presence of IL-21, IL-7, and IL-15. As a control group for non-expanded cells, naïve CD8 T cells enriched by a depletion step using anti-CD4, anti-CD56, and anti-CD19, and a positive enrichment step using anti-CD45RA, were maintained in an antigen free environment in the presence of only IL-7 until day 14.

Interestingly, while on day 0, the groups treated or untreated with anti-CD19 exhibited markedly different levels of CD8 T cells, this difference was abolished as early as day 7 (FIG. 11), and also when tested on day 14 (FIG. 12), likely due to selective death of B cells in the culture. Similarly, the positive selection of CD45RA+ cells after the initial CD8 T cell purification only marginally contributed to the final enrichment of CD8+ T cells with a Tcm phenotype. Thus, all four groups showed similar levels of the desired cells with a minor advantage for the two groups also enriched for naïve cells by anti CD45RA.

This initial result shown above in a typical experiment was further analyzed by comparing average results attained in the control group exposed to optimal cell isolation reagents ("CD4− CD56− CD19−, CD45RA+") to the other groups in which an attempt to eliminate the use of anti-CD19 or anti CD45RA was done.

Thus, the average percent of CD8 T cells (FIG. 13A), and more importantly, the percent Tcm (FIG. 13B) in all the experimental groups when calculated as a percent of the level attained in the optimal control group were very similar.

In contrast, marked differences were found in the average expansion of each cell preparation when tested on day 10 of culture, ranging from 65.6±0.5% to 105.2±6.8% (FIG. 14A). However, the differences in expansion capacity were counteracted by the reduced yield associated with the second purification step (FIG. 14B).

As can be seen in FIG. 14C, showing the final calculated yield of Tcm at day 10, the addition of a second step of positive enrichment of naïve cells with anti-CD45RA only decreased the final yield of Tcm cells, from 141% to 123%, when using initial depletion with anti-CD4 and anti-CD56, or from 157% to 100%, when the negative selection step also included anti-CD19.

Collectively these results suggest that the protocol based on minimal use of reagents for the isolation of CD8 T cells, namely negative selection with anti-CD4 and anti-CD56, is satisfactory for clinical application in the autologous setting.

Example 2

Large Scale Preparation of Human Anti-3$^{rd}$ Party Tcm in Plastic Bags Using GMP Grade Reagents To simulate the conditions anticipated when using patients own PBMC for the generation of autologous Tcm, initially two large scale leukaphersis procedures were performed, from two normal donors, and a large number of mononuclear cells were cryopreserved (divided into several batches). Each batch was used for one large scale experiment. In the first experiment, several technical problems were encountered including difficulty in the generation of DCs from the frozen bags according to the Wurzburg protocol and sourcing of a new GMP grade IL-15 for which the biological activity was unclear. These problems, which resulted in a very poor CD8 T cell expansion (around 3 folds), were corrected in the subsequent experiments by using the presently described protocol for DCs (as described above) and by using the appropriate concentration of IL-15 (i.e. 300 U/ml).

As can be seen in FIG. 15, when PBMC of the same donor were generated in two large scale experiments against two different 3$^{rd}$ party DCs, similar CD8 T cell expansion was attained ranging from 26.8 to 31.0 folds at day 11. Considering that at this day the cells exhibited a linear growth it is likely that further expansion could be attained at later time points. However, this level of expansion is satisfactory as it allows potential administration of up to 3×10$^7$ cells per Kg body weight. Interestingly, while at day 0 it was found that the leukaphersis preparation was largely contaminated with CD14+ monocytes and CD20 B cells, these cells disappear upon cell culture and the final cell composition at day 12 comprised 94% and 98% CD8+CD3+ T cells, respectively (FIGS. 16A-16B).

Importantly, Tcm phenotype attained in the two cultures against different DCs were within the range of the small scale experiments although some variability occurred (FIGS. 17A-17B). Thus, while at day 5 in both experiments high level of Tcm phenotype (77% and 71%, respectively) was found, this level declined more significantly in the culture against the 2$^{nd}$ DC donor upon the 9th day (65% vs. 46%) and day 12 (62% vs. 35%). This variability which was not observed significantly in the small scale experiments could be explained in part by a relative difficulty to remove the DCs on day 5, as they are less likely to adhere to the plastic bag compared to their adhesion to the plates used in the small scale experiments. Thus, the longer presence and stimulation with the DCs could lead to a more pronounced transition from a Tcm to a Teff phenotype.

Example 3

GVL Potential of the Human Anti-3$^{rd}$ Party Tcm Against an Established Cell Line Considering that in the autologous setting the potential use of anti-3$^{rd}$ party Tcm is solely for eradicating residual tumor cells (in the allogeneic setting it also serves to enhance engraftment of the BM cells) it is important to develop a straightforward assay for cytotoxic capacity ex-vivo, which could be used for quality control prior to infusion of the Tcm to the patient. To that end, a TCR independent assay was used based on the demonstration by Lask et al. [Lask A et al., J Immunol. (2011) 187(4):2006-14] that a MHC mutated line not recognizable by TCR due to this mutation, can still be killed by anti-3$^{rd}$ party CTLs through their TCR independent killing mechanism. Clearly, if applicable also for human Tcm, such a killing modality could serve to distinguish the Tcm killing from that exhibited by NK cells.

To address this question, a mixed lymphocyte reaction (MLR) was carried out with anti-3$^{rd}$ party Tcm targeting B-cell lymphoma and plasma cell leukemia cell lines and the percent apoptotic cells was measured after 22 hours. As can be seen in FIG. 17C, representing a typical experiment, marked GVL reactivity was exhibited by the Tcm.

In a different experiment, CD8 T cells were first enriched by extensively depleting non CD8 T cells (i.e., CD4+ T cells, γ/δ T cells, B cells, NK cells, dendritic cells, monocytes, granulocytes, and erythroid cells) using magnetic bead sorting. As can be seen in FIG. 18, representing a typical experiment, the percent of contaminating NK and NKT cells was very low (below 0.1% for NK cells, and below 1.9% for NKT cells) for all four groups tested.

The highly purified CD8 T cells were then incubated with two types of cells: a) H.My C1R HLA-A2 K66A mutant cell line (K66A) to demonstrate TCR independent killing, and b) H.My C1R (Neo), a B-cell lymphoblastoid line lacking surface HLA A and B antigens and therefore insensitive to killing by Tcm via a mechanism which requires interaction between the CD8 molecule on the Tcm and the α3 domain on MHC of the target leukemia cells.

As shown in FIGS. 19A-19D, marked killing of the K66A mutated target cells compared to the MHC-I-deficient H.My C1R (Neo) cells was exhibited by anti-3$^{rd}$ party Tcm. Thus, human Tcm similarly to human anti-3$^{rd}$ party CTLs can kill B cell tumor cells through a TCR independent killing mechanism, which, in contrast to NK mediated killing that requires MHC expression on the target cells.

Most importantly, when further analyzed by comparing average results attained in the control group exposed to optimal cell isolation reagents ("CD4– CD56– CD19–, CD45RA+") to the other groups in which the use of anti-CD19 or anti CD45RA (FIGS. 19A-19D) was reduced, showed that the percent TCR independent killing of the H.My C1R HLA-A2 K66A mutant cell line in all the experimental groups (calculated as a percent of the level attained in the optimal control group) was very similar (FIG. 20) (P>0.05 when comparing all three test groups to the reference control group).

Collectively, these results suggest that the GVL reactivity exhibited by cells isolated with a minimal use of reagents for the isolation of CD8 T cells, is not inferior to that associated with more extensive isolation protocols.

The killing of autologous B-CLL tumor cells by Tcm in-vivo are done, using a Hu/SCID model previously employed for the demonstration of such B-CLL killing by anti-$3^{rd}$ party CTLs.

Example 4

Generation of Allogeneic Human Anti-$3^{rd}$ Party Tcm Cells

Initiation of a New GMP Grade Approach to Minimize Risk of GVHD when Using Allogeneic Human Anti-$3^{rd}$ Party Tcm As previously demonstrated in a mouse model, anti-$3^{rd}$ party Tcm could be very useful for tolerance induction in allogeneic BMT [Ophir E. et al. Blood. (2010) 115(10): 2095-104]. In this case, naïve CD8+ T cells originating from the allogeneic BM donor serve as responders, and $3^{rd}$ party donor dendritic cells (DC) are used as stimulators to enable the generation of host non-reactive Tcm cells. In order to avoid GVHD, the $3^{rd}$ party donor is selected so as to ensure that none of his HLA class I alleles are shared with the HLA class I alleles of the host.

Nonetheless, considering that human patients may be more prone to GVHD than inbred mice, clinical translation of this approach must be pursued with caution. Additional allo-depleting steps, such as photo-depletion or selection of activated cells at the end of the anti-third party allo-stimulation period, might be required in order to further reduce the risk of GVHD.

Modifications of the Autologous Human Protocol (for Allogeneic Protocol)

As shown in FIGS. 21-22, the protocol for generating Tcm for the allogeneic setting differs from the protocol for the autologous setting in two major steps:
  a) Selection of CD45RA+ cells following the isolation CD8 T cells. Memory T-cells have lower activation threshold than naïve T cells that can cause non-specific cytokine-driven expansion of the memory T-cell fraction. These cells may include clones that cross-react with host antigens, thus increasing the risk for GVHD induction. In order to minimize the effect caused by the difference in percentage of naïve T cells between different human donors, and to reduce the risk for GVHD, naïve CD8 T (CD45RA+CD8+) cells were used as the source for the generation of Tcm cells.
  b) Removal of potentially host reactive T cells at the end of the culture, by depletion of CD137+ activated CD8 T cells.

Extension of the IL-7 and IL-15 Deprivation Period

As described for the autologous cultures (hereinabove), the present inventors have observed that naïve CD8 T cells exposed to IL-7 and IL-15 proliferate in an antigen independent manner. On the other hand, naïve CD8 T cells exposed to IL-21 in the absence of allogeneic stimulation did not proliferate, and did not even survive beyond day 7 of culture. Therefore, delaying the addition of IL-7 and IL-15 from day 3 to day 7 could potentially lead to a selective depletion of anti-host clones not responsive to the $3^{rd}$ party stimulators.

In order to define the optimal timing for the addition of cytokine vis-à-vis alloreactivity depletion, naïve CD8 T cells were stimulated with irradiated allogeneic 3rd party DC at a ratio of 4:1 in the presence or absence of IL-21 for 7 days. Thereafter, the cells received no further activation and were expanded with IL-7 and IL-15 (FIG. 23B), IL-15 and IL-21 (FIG. 23C), or IL-15 alone (FIG. 23D) until day 13; the resulting cell populations were compared to the naïve CD8 T cells cultured according to the reference control group, expanded as described for the autologous setting (incubation on d (0-3) with IL21 and DC; on d(3-13), addition of IL7+IL15 (FIG. 23A).

Using the same sequence of cytokine addition as the reference control group but with different timing, namely, IL-21 addition was extended from 3 days to 7 days, and IL-7 and IL-15 were added on day 7 and not on day 3, hindered the expansion of the cells (FIG. 24A) (proliferation only to 54±7% of that exhibited by the reference control group). However, induction of central memory phenotype was similar (FIG. 24B) (99±14.8% of that exhibited by the reference control group).

As shown, removing IL-7 and extending the addition of IL-21 to the end of the culture, reduced expansion of the cells (FIG. 24A) (60±13% of the proliferation exhibited by the reference control group), as well as decreased central memory phenotype acquisition (82±6.8% of the Tcm level exhibited by the reference control group, FIG. 24B).

Priming of naïve CD8 T cells using 7 days cytokine deprivation, followed by addition of only IL-15 from day 7 drastically reduced the expansion potential of the cells (only 5±1.3% proliferation of that exhibited by the reference control group), and also decreased central memory phenotype acquisition (FIG. 24B) (68±26% of the Tcm level exhibited by the reference control group).

The most critical parameter, namely depletion of host reactive clones (tested with appropriate donors who are completely distinct in HLA Class I from the $3^{rd}$ party cells used for stimulation) are examined. Further experiments to optimize the cytokine deprivation period are also carried out.

A Two Stage Magnetic Sorting Approach for Depletion of Alloreactivity, Based on the CD137 Activation Marker An elegant way to deplete anti-host clones based on the $3^{rd}$ party concept may be achieved by a two stage magnetic sorting technique, comprising the following CD137 selection steps:
  a. Positive selection of anti-$3^{rd}$ party specific clones at the beginning of the culture.
  b. Depletion of anti-host specific clones near the end of the culture.

Recently, CD137 has been described to be a suitable marker for antigen-specific activation of human $CD8^+$ T cells, as CD137 is not expressed on resting $CD8^+$ T cells and its expression is reliably induced after 24 hours of stimulation.

In order to evaluate this approach, naïve CD8 T cells were stimulated with irradiated allogeneic 3rd party DC in the presence of IL-21. After 14 hours of activation, CD137+ cells were positively selected by magnetic sorting. CD137+ cells were then re-stimulated with irradiated allogeneic 3rd party DC in the presence of IL-21 until day 3. Thereafter, the cells were expanded with IL-7 and IL-15 until day 10 and, and were then activated with irradiated host PBMC in the presence of IL-7 and IL-15. After 24 hours of activation, CD137+ cells were depleted by magnetic sorting. The CD137 depleted cells were re-plated with IL-7 and IL-15 and cultured until day 14. On selected days, cells were evaluated for cell numbers by trypan blue exclusion and percentage of Tcm (CD62L+CD45RO+) within the CD8 T cell population using FACS analysis. Frequency of anti-3$^{rd}$ party and anti-host alloreactive cells was evaluated by CFSE assay against 3$^{rd}$ party or host irradiated PBMCs. These results were compared to those attained in the control group stimulated in the presence of IL-21 for 3 days and thereafter expanded with IL-7 and IL-15 ("reference control group").

Thus, as can be seen in FIG. 25, while immediately after enrichment for naïve CD8 T cells (day 0), only 0.7% of the total CD8 T cells expressed CD137+, upon activation against 3$^{rd}$ party DC in the presence of IL-21 for 14 h, the percentage of CD8 T cells expressing CD137+ from the total CD8 T cell compartment increased to 8.3% as opposed to 2.5% in the absence of DC stimulation. Magnetic sorting of this subpopulation of activated cells led to marked enrichment of CD137+ cells (85%, respectively) and the level of CD62L+CD8 T cells in the total CD8 T cell compartment drastically decreased from 84% to 14% (data not shown).

As shown in Table 5, below, this positive selection was associated with reduced cell recovery. Thus, on day 0, the yield from PBMC depleted of adherent cells after enrichment for naïve CD8 T cells was 7.6% and on day 1, after the positive selection for CD137+, the yield decreased to 0.25% (3.3% of 7.6%). When evaluated on day 7 of culture, the test group of CD8 T cells subjected to positive selection of CD137+ cells highly resembled the reference control group in the percent of Tcm cells (67% vs. 70%, respectively), and this similarity between the groups in percent Tcm was also maintained on day 10 of culture (54% vs. 52%, respectively) (FIG. 26).

TABLE 5

Comparison of proliferation and final cell number

| e | d | c | b | a | Group |
|---|---|---|---|---|---|
| (7.6) × (61) = 463% | 61 | | | 7.6% | Reference control |
| (0.25) × (72) = 18% | 72 | | (3.3% from 7.6%) = 0.25% | | Anti-3rd CD137+ and Anti host CD137− |

Naïve CD8 T cells were stimulated with irradiated allogeneic 3rd party DC at a ratio of 4:1 in the presence of IL-21 for 3 days. The cells received no further activation thereafter and were expanded with IL-7 and IL-15 until day 14 ("Reference control group"). Alternatively, naïve CD8 T cells were stimulated with irradiated allogeneic 3rd party DC at a ratio of 5.7:1 in the presence of IL-21. After 14 hours of activation, CD137+ cells were positively selected by magnetic sorting. CD137+ cells were then re-stimulated with irradiated allogeneic 3rd party DC in at a ratio of 4:1 in the presence of IL-21 until day 3. Thereafter, the cells were expanded with IL-7 and IL-15 until day 10. On day 10, were activated with irradiated host PBMC in the presence of IL-7 and IL-15 (at a ratio of 1 to 2). After 24 h, CD137+ cells were depleted by magnetic sorting. The CD137 depleted cells were re plated with IL-7 and IL-15 and cultured until day 14 ("Anti 3$^{rd}$ CD137+ and Anti host CD137−"). On the indicated days, cells were counted by trypan blue exclusion a=Yield after enrichment of naïve CD8 T cells (Represented as percent of starting number of PBMC-adhered cells).

b=Yield after activation with 3rd party DCs and enrichment of CD137+ CD8 T cells (Represented as percent of starting number of PBMC-adhered cells).

c=Fold expansion from day 0 at day 13.

d=Fold expansion from day 0 at day 14.

e=Final cell number=(Yield)×(Fold Expansion from day 0) (Represented as percent of starting number of PBMC-adhered cells).

Moreover, when cell composition (% CD8 T cells, % NK cells and % NKT cells) was evaluated on days 7 and 10 of culture, the test group of CD8 T cells subjected to positive selection of CD137+ cells, highly resembled the reference control group in its cell composition (Table 6, below).

TABLE 6

Enrichment of anti-3$^{rd}$ party specific CD8 T cells by positive selection of CD137+ cells does not drastically change cell composition

| (NKT 16+) CD3+ CD16+ | (NKT 56+) CD3+ CD56+ | (NK16+) CD3− CD16+ | (NK56+) CD3− CD56+ | (CD8 T cells) CD3+ CD8+ | Day 7 |
|---|---|---|---|---|---|
| 2.6 | 5.6 | 1.3 | 2 | 92.5 | Reference control group |
| 5.2 | 7.8 | 3.8 | 3.2 | 88 | anti-3rd party CD137+ |

| (NKT 16+) CD3+ CD16+ | (NKT 56+) CD3+ CD56+ | (NK16+) CD3− CD16+ | (NK56+) CD3− CD56+ | (CD8 T cells) CD3+ CD8+ | Day 10 |
|---|---|---|---|---|---|
| 2.8 | 8.3 | 3.2 | 2.1 | 91.8 | Reference control group |
| 3.6 | 6.3 | 4 | 4.1 | 87 | anti-3rd party CD137+ |

Naïve CD8 T cells were stimulated with irradiated allogeneic 3rd party DC at a ratio of 4:1 in the presence of IL-21 for 3 days. Thereafter, the cells received no further activation and were expanded with IL-7 and IL-15 until day 10 ("Reference control group"). Alternatively, naïve CD8 T cells were stimulated with irradiated allogeneic 3rd party DC at a ratio of 5.7:1 in the presence of IL-21. After 14 hours of activation, CD137+ cells were positively selected by magnetic sorting. CD137+ cells were then re-stimulated with irradiated allogeneic 3rd party DC at a ratio of 4:1 in the presence of IL-21 until day 3. Thereafter the cells were expanded with IL-7 and IL-15 until day 10. Cells were evaluated for cell composition by FACS analysis.

On the other hand, as shown in FIG. 27, the test group of CD8 T cells subjected to positive selection of CD137+ cells, exhibited superior expansion potential in comparison to the reference control group at both time points (35 vs. 7 fold expansion from day 0 on day 7, respectively, and 119 vs. 34 fold expansion from day 0 on day 10, respectively). On day 10, the group of CD8 T cells subjected to positive selection of CD137+ cells was divided into two test groups. In the first group, cells continued to be expanded with IL-7 and IL-15 until day 14 ("Anti 3$^{rd}$ CD137+"), while cells in the second test group were activated with irradiated host PBMC in the presence of IL-7 and IL-15. After 24 h of activation CD137+ cells were depleted by magnetic sorting. The CD137 depleted cells were then re plated with IL-7 and IL-15 and cultured until day 14 ("Anti 3$^{rd}$ CD137+ and Anti-host CD137−").

When evaluated on day 13, CD8 T cells from the test group subjected to positive selection of CD137+ continued to exhibited superior expansion potential in comparison to the reference control group at both time points (134 vs. 61 fold expansion, respectively). In contrast, CD8 T cells from the test group subjected to both anti-3rd party positive selection of CD137+ and depletion of anti-host CD137+ cells, exhibited lower expansion potential when evaluated on day 14 (72 fold expansion) (FIG. 27) indicating that cell expansion between days 11 to 14 could not compensate for the loss of cells caused by the depletion of CD137+ anti-host specific alloreactive T cells.

As shown in FIG. 28, when CD137 expression was evaluated on day 10, only 0.5% of the total CD8 T cells compartment in the CD8 T cells subjected to positive selection of CD137+ cells expressed CD137+. Thus, the CD8 T cells in this group down-regulated considerably the expression of CD137 (from 85% on day 1 to only 0.5 on day 10).

However, after 24 h of activation with irradiated host PBMC (at a 1 to 2 ratio, in favor of the host PBMC), the percent of CD8 T cells expressing CD137+ from the total CD8 T cell compartment increased to 16%. Depletion of these CD137+ cells by magnetic sorting decreased the percent of CD8 T cells expressing CD137 of the total CD8 T cell compartment, from 16% to 3%.

Final analysis of residual anti-host alloreactivity was performed on day 14, by comparing the level of CFSE retaining cells upon stimulation against host PBMC as opposed to 3$^{rd}$ party PBMC in the presence of IL-7.

As shown in FIG. 29, the number of cells specifically dividing after stimulation with 3$^{rd}$ party PBMC was approximately 3 times higher in the group subjected to the CD137 based positive and negative selection compared to the reference control group (2259 vs. 0.741 dividing cells, respectively). Most importantly, the removal of CD137+ cells towards the end of the culture, completely prevented proliferation in response to host PBMC, in contrast to the reference control group which exhibited detectable proliferation (134 dividing cells). Interestingly, the group undergoing positive selection of cells activated against 3$^{rd}$ party without removal of anti-host clones at the end of the culture, exhibited higher level of host reactive cells compared to the control group, indicating potential cross reactivity between the MHC allotypes of host and 3$^{rd}$ party stimulators (although deliberately mis-matched by HLA typing.) Thus, while the importance of anti-host depletion step at the end of the culture is clearly indicated, further studies are required to evaluate the potential role of the first positive selection of anti-3$^{rd}$ party activated cells.

However, as shown in Table 5, above, the successful depletion of anti-host specific clones by the two stage CD137 based magnetic sorting, affords on the whole lower cell recovery at the end of the culture (18% vs. 463%, represented as percent from input number of PBMC-adherent cells, respectively).

Collectively, this preliminary experiment indicates that depletion of alloreactivity by two-stage magnetic sorting, based on the CD137 activation marker, is feasible and might be incorporated into the present protocol for generating host non-reactive allogeneic Tcm cells. Encouraging attributes indicated are: 1) the high expression levels induced by the allogeneic activation upon positive selection were completely down-regulated on day 10, allowing for another allo-activation against host antigens. 2) Cell composition and percent of Tcm cells were not drastically affected by the magnetic sorting, based on the CD137 activation marker. 3) The removal of CD137+ cells towards the end of the culture, completely prevented proliferation in response to host PBMC, in contrast to the reference control group, which exhibited detectable proliferation (134 dividing cells). Current studies include: 1) the use of FcR blocking before the positive selection step. 2) Using Host DC instead of PBMC for more effective detection of host reactive cells at the end of the culture. 3) Adding more clinically available activation markers like CD25 or IFN gamma capture to the depletion step.

CONCLUSIONS

The use of CD137 depletion at the end of Tcm generation might afford a feasible approach to further deplete these cells of alloreactivity.

Attempts to continue refining the use of CD137 depletion in conjunction with CD25 depletion, both of which are available as GMP reagents, are explored.

In addition, experiments are carried out to minimize potential cross reactivity by using artificial APC bearing only one HLA-I allele.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of treating a subject in need of a cell or tissue transplantation, the method comprising:
   (i) generating an isolated population of cells comprising non-graft versus host (GVH) inducing anti-third party cells having a central memory T-lymphocyte (Tcm) phenotype, said cells being tolerance-inducing cells and/or endowed with anti-disease activity and capable of homing to the lymph nodes following transplantation, and wherein at least 50% of the isolated population of cells are CD3+CD8+ cells of which at least 50% comprises a CD3$^+$, CD8$^+$, CD62L$^+$, CD45RA$^-$, CD45RO$^+$ signature, by a method comprising:
      (a) treating peripheral blood mononuclear cells (PBMC) from a donor with an agent capable of depleting CD4$^+$ and CD56$^+$ cells so as to obtain CD8$^+$ T cells;
      (b) contacting said CD8+ T cells with a third party antigen or antigens in the presence of IL-21 so as to allow enrichment of antigen reactive cells, wherein said third party antigen or antigens comprise antigen presenting cells presenting said third party antigen or antigens, and wherein said contacting is effected for 12 hours to 5 days;

(c) adding IL-15 and IL-7 to said culture comprising said antigen reactive cells, said third party antigen or antigens and said IL-21 of step (b) and culturing for 12 hours to 3 days; and (d) culturing said cells resulting from step (c) in the presence of IL-21, IL-15 and IL-7 in an antigen free environment so as to allow proliferation of cells comprising said Tcm phenotype, wherein said culturing is effected for 5-20 days;

(ii) transplanting a cell or tissue transplant from a donor into the subject; and (iii) administering to the subject a therapeutically effective amount of said isolated population of cells comprising said non-GVH inducing anti-third party cells having said Tcm phenotype, wherein said cell or tissue transplant and said isolated population of cells are derived from the same donor, thereby treating the subject.

2. The method of claim 1, wherein said cell or tissue transplant comprises immature hematopoietic cells.

3. The method of claim 1, wherein said cell or tissue transplant is selected from the group consisting of a liver, a pancreas, a spleen, a kidney, a heart, a lung, a skin, an intestine and a lymphoid/hematopoietic tissue or organ.

4. The method of claim 1, wherein said cell or tissue transplant comprises a co-transplantation of several organs.

5. The method of claim 4, wherein said co-transplantation comprises transplantation of immature hematopoietic cells and a solid organ.

6. The method of claim 5, wherein said immature hematopoietic cells and said solid organ are obtained from the same donor.

7. The method of claim 5, wherein said immature hematopoietic cells are transplanted prior to, concomitantly with, or following said transplantation of said solid organ.

8. The method of claim 1, wherein said isolated population of cells are administered prior to, concomitantly with, or following said cell or tissue transplant.

9. The method of claim 1, further comprising:
depleting adherent cells from said PBMC prior to step (a); and/or
selecting CD45RA$^+$and/or CD45RO$^-$cells from said PBMC prior to step (a).

10. The method of claim 1, wherein said contacting in said presence of IL-21 according to step (b) is effected for 2-3 days.

11. The method of claim 1, further comprising:
selecting for activated cells following step (b) and prior to step (d); or
depleting alloreactive cells following step (d).

12. The method of claim 1, wherein said culturing in said presence of IL-21, IL-15 and IL-7 in said antigen free environment according to step (d) is effected for 7-11 days.

13. The method of claim 1, wherein said isolated population of cells are devoid of graft versus host (GVH) reactive cells.

14. The method of claim 1, wherein said antigen presenting cells comprise dendritic cells.

15. The method of claim 14, wherein said dendritic cells comprise said third party antigen or antigens pulsed dendritic cells.

16. The method of claim 1, wherein said culturing said antigen reactive cells with said third party antigen or antigens in the presence of IL-21, IL-15 and IL-7 according to step (c) is effected for 1-2 days.

17. A method of treating a subject in need of an immature hematopoietic cell transplantation, the method comprising:

(i) generating an isolated population of cells comprising non-graft versus host (GVH) inducing anti-third party cells having a central memory T-lymphocyte (Tcm) phenotype, said cells being tolerance-inducing cells and/or endowed with anti-disease activity and capable of homing to the lymph nodes following transplantation, wherein at least 50% of the isolated population of cells are CD3+CD8+cells of which at least 50% comprises a CD3$^+$, CD8$^+$, CD62L$^+$, CD45RA$^-$, CD45RO$^+$ signature, by a method comprising:

(a) treating peripheral blood mononuclear cells (PBMC) from a donor with an agent capable of depleting CD4$^+$and CD56$^+$cells so as to obtain CD8$^+$T cells;

(b) contacting said CD8+T cells with a third party antigen or antigens in the presence of IL-21 so as to allow enrichment of antigen reactive cells, wherein said third party antigen or antigens comprise antigen presenting cells presenting said third party antigen or antigens, and wherein said contacting is effected for 12 hours to 5 days;

(c) adding IL-15 and IL-7 to said culture comprising said antigen reactive cells, said third party antigen or antigens and said IL-21 of step (b) and culturing for 12 hours to 3 days; and (d) culturing said cells resulting from step (c) in the presence of IL-21, IL-15 and IL-7 in an antigen free environment so as to allow proliferation of cells comprising said Tcm phenotype, wherein said culturing is effected for 5-20 days;

(ii) transplanting immature hematopoietic cells from a donor into the subject; and (iii) administering to the subject a therapeutically effective amount of said isolated population of cells comprising said non-GVH inducing anti-third party cells having said Tcm phenotype, wherein said immature hematopoietic cells and said isolated population of cells are derived from the same donor, thereby treating the subject.

18. The method of claim 17, wherein said isolated population of cells are administered prior to, concomitantly with, or following said immature hematopoietic cells.

* * * * *